(12) United States Patent
Gold

(10) Patent No.: US 6,734,211 B1
(45) Date of Patent: May 11, 2004

(54) COMPOSITIONS AND METHODS FOR PROMOTING NERVE REGENERATION

(75) Inventor: Bruce G. Gold, West Linn, OR (US)

(73) Assignee: Oregon Health & Sciences University, Portland, OR (US)

( * ) Notice: Subject to any disclaimer, the term of this patent is extended or adjusted under 35 U.S.C. 154(b) by 16 days.

(21) Appl. No.: 10/030,904
(22) PCT Filed: Jul. 7, 2000
(86) PCT No.: PCT/US00/18539
§ 371 (c)(1), (2), (4) Date: Apr. 29, 2002
(87) PCT Pub. No.: WO01/03692
PCT Pub. Date: Jan. 18, 2001

Related U.S. Application Data
(60) Provisional application No. 60/143,180, filed on Jul. 9, 1999.

(51) Int. Cl.$^7$ ............................................. A61K 31/21
(52) U.S. Cl. ...................................................... 514/513
(58) Field of Search ......................................... 514/513

(56) References Cited

U.S. PATENT DOCUMENTS

| | | |
|---|---|---|
| 4,228,079 A | 10/1980 | Calton |
| 5,192,773 A | 3/1993 | Armistead et al. |
| 5,330,993 A | 7/1994 | Armistead et al. |
| 5,516,797 A | 5/1996 | Armistead et al. |
| 5,525,523 A | 6/1996 | Soldin |
| 5,543,423 A | 8/1996 | Zelle et al. |
| 5,612,350 A | 3/1997 | Or et al. |
| 5,614,547 A | 3/1997 | Hamilton et al. |
| 5,620,971 A | 4/1997 | Armistead et al. |
| 5,622,970 A | 4/1997 | Armistead et al. |
| 5,639,592 A | 6/1997 | Evans et al. |
| 5,650,430 A | 7/1997 | Sugimura et al. |
| 5,780,484 A | 7/1998 | Zelle et al. |
| 5,811,434 A | 9/1998 | Zelle et al. |
| 5,840,736 A | 11/1998 | Zelle et al. |
| 5,968,921 A | 10/1999 | Gold |
| 6,037,370 A | 3/2000 | Armistead |

FOREIGN PATENT DOCUMENTS

| | | |
|---|---|---|
| WO | WO 92/04370 | 3/1992 |
| WO | WO 92/19593 | 11/1992 |
| WO | WO 92/19745 | 11/1992 |
| WO | WO 92/21313 | 12/1992 |
| WO | WO 93/07269 | 4/1993 |
| WO | WO 93/23548 | 11/1993 |
| WO | WO 96/40140 | 12/1996 |
| WO | WO 96/40633 | 12/1996 |
| WO | WO 97/18828 | 5/1997 |
| WO | WO 98/20891 | 5/1998 |
| WO | WO 98/20892 | 5/1998 |
| WO | WO 98/20893 | 5/1998 |
| WO | WO9830900 | * 7/1998 |
| WO | WO 99/21552 | 5/1999 |
| WO | WO 01/03692 A1 | 1/2001 |

OTHER PUBLICATIONS

US 5,654,332, 8/1997, Armistead (withdrawn)

DiJulio DH et al., "Ryanodine Receptor Type III (Ry3R) Identification In Mouse Parotid Acini. Properties And Modulation Of [3H] Ryanodine–Binding Sites," *J. Biol Chem.*, 272:15687–96 (1997), Abstract only.

Sherwood DJ et al., "Differential Regulation Of MAP Kinase, p70(S6K), And Akt By Contraction And Insulin In Rat Skeletal Muscle," *Am J Physiol.*, 276:E870–8 (1999), Abstract only.

Itoh T et al., "A Protein Factor For Ras p21–Dependent Activation Of Mitogen–Activated Protein (MAP) Kinase Through MAP Kinase Kinase," *Proc Natl Acad Sci U.S.A.*, 90:975–9 (1993), Abstract only.

Chao TS et al., "Differential Raf Requirement For Activation Of Mitogen–Activated Protein Kinase By Growth Factors, Phorbol Esters, And Calcium," *J Biol Chem.*, 269:7337–41 (1994), Abstract only.

Bornfeldt KE et al., "Insulin–Like Growth Factor–I And Platelet–Derived Growth Factor–BB Induce Directed Migration Of Human Arterial Smooth Muscle Cell Via Signaling Pathways That Are District From Those Of Proliferation," *J Clin Invest.*, 93:1266–74 (1994), Abstract only.

Frodin M et al., "Glucose, Other Secretagogues, And Nerve Growth Factor Stimulate Mitogen–Activated Protein Kinase In The Insulin–Secreting Beta–Cell Line, INS–1," *J Biol Chem.*, 270:7882–9 (1995), Abstract only.

(List continued on next page.)

*Primary Examiner*—Vickie Kim
(74) *Attorney, Agent, or Firm*—Klarquist Sparkman, LLP

(57) ABSTRACT

Neurite outgrowth and nerve regeneration are promoted by disruption of the steroid receptor complex and stimulation of MAP kinase/kinase activity. This disruption can take the form of disruption of the physical assembly or function of the steroid receptor complex, such as the mature complex or a precursor of the mature complex that is required for assembly of the mature complex. Geldanamycin and its analogs, bastadin and members of the bastadin family, and radicicol and its analogs, as well as FKBP-52 antibody, are shown to disrupt the complex and promote nerve growth. Assays for finding neurotrophic compounds, as well as compounds found by these assays, pharmaceutical compositions into which they are incorporated, and methods of treating subjects having neuronal dysfunction caused by injury or disease are disclosed. Any of these compounds can be used in combination with a therapeutically effective amount of heat, such as heat applied locally to an area where nerve growth is desired, or systemically in an organism in which neurite growth is desired. Alternatively, these compounds can be used in association with a template, such as a tubular member that defines an anatomic pathway along which nerve regeneration is desired (particularly around a transected or partially transected nerve).

13 Claims, 12 Drawing Sheets

OTHER PUBLICATIONS

Schliess F et al., "Mitogen–Activated Protein Kinases Mediate The Stimulation Of Bile Acid Secretion By Tauroursodeoxycholate In Rat Liver," *Gastroenterology*, 113:1306–14 (1997), Abstract only.

Kato Y et al., "BMK1/ERK5 Regulates Serum–Induced Early Gene Expression Through Transcription Factor MEF2C," *EMBO J.*, 16:7054–66 (1997), Abstract only.

Chang NS, "Hyaluronidase Enhancement Of TNF–Mediated Cell Death Is Reversed By TGF–Beta 1," *Am J Physiol.*, 273:C1987–94 (1997), Abstract only.

Pahan K et al., "Sphingomyelinase And Ceramide Stimulate The Expression Of Inducible Nitric–Oxide Synthase In Rat Primary Astrocytes," *J. Biol Chem.*, 273:2591–600 (1998), Abstract only.

Kwon HJ et al., "Potent And Specific Inhibition Of p60v–src Protein Kinase Both In Vivo And In Vitro By Radicicol," *Cancer Res.*, 52:6926–30 (1992), Abstract only.

Shimada Y et al., "Induction Of Differentiation Of HL–60 Cells By The Anti–Fungal Antibiotic Radicicol," *J Antibiot (Tokyo)*, 48:824–30 (1995), Abstract only.

Tomono M et al., "Inhibitors Of Calcineurin Block Expression Of Cyclins A And E Induced By Fibroblast Growth Factor In Swiss 3T3 Fibroblasts," *Arch Biochem Biophys.*, 353:374–8 (1998), Abstract only.

Campbell V et al., "Biphasic Modulation Of Intracellular Ca2+Concentration By Interleukin–1beta In Cortical Synaptosomes: Involvement Of A Pertussis Toxin–Sensitive G–Protein And Mitogen–Activated Protein Kinase," *Neuroreport.*, 9:1923–7 (1998), Abstract only.

Kwon HJ et al., "Potent And Specific Inhibition Of p60v–src Protein Kinase Both In Vivo And In Vitro By Radicicol," *Cancer Res.*, 52:6926–30 (1992), Abstract only.

Samanta S et al., "Hydrogen Peroxide Enchances Signal–Responsive Arachidonic Acid Release From Neurons: Role of Mitogen–Activated Protein Kinase," *J Neurochem.*, 70:2082–90 (1998), Abstract only.

Weiss RH et al., "MEK Inhibition Augments Raf Activity, But Has Variable Effects On Mitogenesis, In Vascular Smooth Muscle Cells," *Am J Physiol.*, 274:C1521–9 (1998), Abstract only.

Tsuchiya T et al., "Expression Of Leptin Receptor In Lung: Leptin As A Growth Factor," *Eur J. Pharmacol.*, 365:273–9 (1999), Abstract only.

Pessah IN et al., "Bastadins Relate Ryanodine–Sensitive And –Insensitive Ca2+ Efflux Pathways In Skeletal SR And BC3H1 Cells," *Am J Physiol.*, 272:C601–14 (1997), Abstract only.

Kuhn RW et al., "Progesterone–Binding Components Of Chick Oviduct. Biochemical Characterization Of Purified Oviduct Progesterone Receptor B Subunit," *J. Biol. Chem.*, 252:308–317 (1977), Abstract only.

Edwards D P et al., "Heat Shock Alters The Composition Of Heteromeric Steroids Receptor Complexes And Enhances Receptor Activity In Vivo." *Biochem.*, 31:2482–91 (1992), Abstract only.

Smith D.F., "Dynamics Of Heat Shock Protein 90–Progesterone Receptor Binding And The Disactivation Loop Model For Steroid Receptor,", *Mol. Endocrinol.*, 7:1418–29 (1993), Abstract only.

Tumlin J.A. et al., "Aldosterone And Dexamethasone Stimulate Calcineurin Activity Through A Transcription–Independent Mechanism Involving Steroid Receptor–Associated Heat Shock Proteins," *J. Clin. Investigation*, 99:1217–23 (1997), Abstract only.

Armistead et al., "Design, Synthesis And Structure Of Non–Macrocyclic Inhibitors Of FKBP12, The Major Binding Protein For The Immunosuppressant FK506," *Acta Cryst* D51:522–528 (1995).

Bozzo et al., "Role Of Tyrosine Phosphorylation In Matrix–Induced Neurite Outgrowth In Human Neuroblastoma Cells," *Exp. Cell Res.*, 214:313–22 (1994).

Buttemeyer et al., "Peripheral Nerve Allotransplant Immunosuppressed With FK 506: Preliminary Results," *Transpl. Proc.*, 27:1877–1878 (1995).

Buttemeyer et al., "Peripheral Nerve Allograft Transplantation With FK 506: Functional, Histological, And Immunological Results Before And After Discontinuation of Immunosuppression," *Ann. Plast. Surg.*, 35:396–401 (1995).

Czar et al., "Geldanamycin, A Heat Shock Protein 90–Binding Benzoquinone Ansamycin, Inhibits Steroid–Dependent Translocation Of The Glucocorticoid Receptor From The Cytoplasm To The Nucleus," *Biochemistry*, 36:7776–7785 (1997).

David et al., "Anoxal Elongation Into Peripheral Nervious Systme "Bridges" After Central Nervous System Injury In Adult Rats," *Science*, 214:931–33 (1981).

Jackowski, "Neural Injury Repair: Hope For The Future As Barriers To Effective CNS Regeneration Become Clearer," *Brit. J. Neurosurg..*, 9:303–317 (1995).

Miller et al., "Increased Neurite Outgrowth Induced By Inhibition Of Protein Tyrosine Kinase Activity In PC12 Pheochromocytoma Cells," *J. Neurochem.*, 60:2134–44 (1993).

Owens–Grillo et al., "The Cyclosporin A–binding Immunophilin CyP–40 And The FK506–Binding Immunophilin hsp56 Bind To A Common Site On hsp90 And Exist In Independent Cytosolic Heterocomplexes With The Untransformed Glucocorticoid Receptor," *J. Biol. Chem.*, 270:20479–20484 (1995).

Ownes–Grillo et al., "Binding Of Immunophilins To The 90 kDa Heat Shock Protein (hsp90) Via A Tetratricopeptide Repeat Domain Is A Conserved Protein Interaction In Plants," *Biochemistry*, 35:15249–15255 (1996).

Pratt, W.B., "The Role Of The hsp90–Based Chaperone System In Signal Transduction By Nuclear Receptors And Receptors Signaling Via MAP Kinase," *Annu. Rev. Pharmacol. Toxicol.*, 37:297–326 (1997).

Pratt, W.B. and Toft, D.O., "Steroid Receptor Interactions With Heat Shock Protein And Immunophilin Chaperones," *Endocrine Reviews*, 18:306–360 (1997).

Preis et al., "Neuronal Cell Differentiation Of Human Neuroblastoma Cells By Retinoic Acid Plus Herbimycin A," *Cancer Res.*, 48:6530–34 (1988).

Ratajczak, T. and Carrello, A., "Cyclophilin 40 (CyP–40), Mapping Of Its hsp90 Binding Domain And Evidence That FKBP52 Competes With CyP–40 For hsp90 Binding," *J. Biol. Chem.*, 271:2961–2965 (1996).

Sanchez, E.R. and Ning, Y–M., "Immunophilins, Heat Shock Proteins, And Glucocorticoid Receptor Actions in Vivo," *Methods* 9:188–200 (1996).

Segnitz et al., "The Function Of Steroid Hormone Receptors Is Inhibited By The hsp90–Specific Compound Geldanamycin," *J. Biol. Chem.*, 272:18694–18701 (1997).

Smith et al., "Progesterone Receptor Structure And Function Altered By Geldanamycin, An hsp90–Binding Agent," *Molecular and Cellular Biology*, 15:6804–6812 (1995).

Smith, "Elements Of Molecular Neurobiology," $2^{nd}$ ed., John Wiley & Sons, pagers 141–142 (1996).

Stancato et al., "The hsp90–binding Antibiotic Geldanamycin Decreases Raf Levels And Epidermal Growth Factor Signaling Without Disrupting Formation Of Signaling Complexes Or Reducing The Specific Enzymatic Activity Of Raf Kinase," *J. Biol. Chem.*, 272:4013–4020 (1997).

Stebbins et al., "Crystal Structure Of An Hsp90–Geldanamycin Complex: Targeting Of A Protein Chaperone By An Antitumor Agent," *Cell*, 89:239–250 (1997).

Tanzer L. et al., "Gonadal Steroid Regulation Of Hamster Facial Nerve Regulation: Effects Of Dihydrotestosterone And Estradiol," *Exp. Neurol.*, 146:258–264 (1997).

Wells et al., "Gel Matrix Vehicles For Growth Factor Application In Nerve Gap Injuries Repaired With Tubes: A Comparison Of Biomatrix, Collagen, And Methylcellulose," *Exp. Neurol.*, 146:395–402 (1997).

Whitesell et al., "Benzoquinonoid Ansamycins Possess Selective Tumoricidal Activity Unrelated To src Kinase Inhibition," *Cancer Res.*, 52:1721–28 (1992).

Whitesell et al., "Inhibition Of Heat Shock Protein HSP90–pp60$^{v-src}$ Heteroprotein Complex Formation By Benzoquinone Ansamycins: Essential Role For Stress Proteins in Oncogenic Transformation," *Proc. Natl. Acad. Sci. USA*, 91:8324–8328 (1994).

Carney, et al., "A New Bastadin From The Sponge Psammaplysilla Purpurea," *J. of Natural Products*, 56:153–157 (1993).

Chen, et al., "Bastadin 10 Stabilized The Open Conformation Of The Ryanodine–Sesitive ca2+ Channel In An FKBP–12 Dependent Manner," *J. Biol. Chem.*, 274:32603–32612 (1999), Abstract only.

Franklin et al., "Bastadin 20 And Bastadin O–Sulfate Esters From Ianthella Basta: Novel Modulators Of The $Ry_1R$ FKBP12 Receptor Complex," *J. of Natural Products*, 59:1121–1127 (1996).

Gulavita et al., "Isolation And Structure Elucidation Of 34–Sulfatobastadin 13, An Inhibitor Of The Endothelin A Receptor, From A Marine Sponge Of The Gensus Ianthella," *J. of Natural Products*, 56:1613–1617 (1993).

Mack, et al., "Novel Modulators Of Skeletal Muscle FKBP12/Calcium Channel Complex From Ianthella Basta. Role Of FKBP12 In Channel Gating," *J. Biol. Chem.*, 269:23236–23249 (1994), Abstract only.

Miao, et al., "Cytotoxic Metabolites From The Sponge Ianthella Basta Collected In Papua New Guinea," *J. of Natural Products*, 33:1441–1446 (1990).

Ohtsuki et al., "Delayed Neuronal Death In Ischemic Hippocampus Involves Stimulation Of Protein Tyrosine Phosphorylation," *American J. of Physiology*, 271:C1085–C1097 (1996).

Pettit et al., "Antineoplastic Agents, 326. The Stereochemistry Of Bastadins 8, 10, and 12 From The Bismarck Archipelago Marine Sponge Iantehella Basta," *J. of Natural Products*, 58:680–688 (1995).

Sano, et al., "Radicicol Potentiates Neurotrophin–Mediated Neurite Outgrowth And Survival Of Cultured Sensory Neurons From Chick Embryo," *J. Neurochem.*, 72:2256–2263 (1999).

Schulte et al., "Antibiotic Radicicol Binds to the N–terminal Domain of Hsp90 and Shares Important Biologic Activities With Geldanamycin," *Cell Stress & Chaperones*, 3 (1996).

Sano, et al., "Radicicol Potentiates Neurotrophin–mediated Neurite Outgrowth and Survival of Cultured Sensory Neurons from Chick Embryo," *J. of Neurochemistry*, vol. 72, p. 2256–2263 (1999).

Ohtsuki, et al., "Delayed Neuronal Death in Ischemic Hippocampus Involves Stimulation of Protein Tyrosine Phosphorylation," *American J. of Physiology*, vol. 271(4), p. C1085–C1097 (1996).

Chen, et al., "Bastadin 10 Stabilized the Open Conformation of the Ryanodine–sesitive ca2+ Channel in an FKBP–12 Dependent Manner" abstract, *J. Biol. Chem*, vol. 274, p. 32603–32612 (1999).

Mack, et al., "Novel Modilators of Skeletal Muscle FKBP12/Calcium Channel Complex from Ianthella Basta. Role of FKBP12 in Channel Gating" abstract, *J. Biol. Chem.*, vol. 269, p. 23236–23249 (1994).

Miao, et al., "Cytotoxic Metabolites from the Sponge Ianthella Basta Collected in Papua New Guinea," *J. of Natural Products*, vol. 33, p. 1441–1446 (Nov.–Dec. 1990).

Carney, et al., "A New Bastadin from the Sponge Psammaplysilla Purpurea," *J. of Natural Products*, vol. 56, p. 153–157 (Jan. 1993).

Gulavita et al., "Isolation and Structure Elucidation of 34–Sulfatobastadin 13, An Inhibitor of the Endothelin a Receptor, from a Marine Sponge of the Genus Ianthella," *J. of Natural Products*, vol. 56, p. 1613–1617 (Sep. 1993).

Pettit et al., "Antineoplastic Agents, 326. The Stereochemistry of Bastadins 8, 10, and 12 from the Bismarck Archipelago Marine Sponge Iantehella Basta," *J. of Natural Products*, vol. 58, p. 680–688 (May 1995).

Franklin et al., "Bastadin 20 and Bastadin o–Sulfate Esters from Ianthella Basta: Novel Modulators of the $Ry_1R$ FKBP12 Receptor Complex," *J. of Natural Products*, vol. 59, p. 1121–1127 (1996).

Schulte et al., "Antibiotic Radicicol Binds to the N–terminal Domain of Hsp90 and Shares Important Biologic Activities With Geldanamycin," *Cell Stress & Chaperones*, vol. 3, p. (1996).

* cited by examiner

COMPOSITIONS AND METHODS FOR PROMOTING NERVE REGENERATION

This application is a §371 U.S. national stage of PCT US00/18539 filed Jul. 7, 2000, which was published in English under PCT Article 21(2), which in turn claims the benefit of U.S. Provisional Application No. 60/143,180 filed Jul. 9, 1999.

FIELD OF THE INVENTION

This invention concerns neurotrophic compounds and agents useful in the treatment of neurological injury and disease.

BACKGROUND OF THE INVENTION

Following traumatic or mechanically induced axonal degeneration in the peripheral nervous system, axonal regeneration often ensues, resulting in functional recovery. However, the rate of axonal elongation (3–4 mm/day) is slow, and sometimes does not result in recovery of full neurological function. If neurological function is restored, recovery usually occurs in weeks or months, depending upon the distance between the site of injury and the target tissue. Therapies that speed regeneration over long distances would be highly beneficial to patients and would significantly reduce health care costs.

Other neurological conditions result from dysfunction of neurons in the peripheral or central nervous systems that is caused by chronic disease or injury. Chronic disease processes can permanently and progressively damage the nervous system, and (particularly in the central nervous system) usually results in permanent loss of function. Such loss of neurological function is a major cause of physical incapacitation and death throughout the world.

The immunosuppressant drug FK506 (USAN tacrolimus; Prograf®) induces immunosuppression by binding the immunophilin FKBP-12. This binding prevents calcineurin from dephosphorylating the transcription factor NF/AT (nuclear factor of activated T-cells), which blocks translocation of calcineurin into the nucleus, and prevents a receptor-mediated increase in the synthesis and secretion of cytokines, such as interleukin-2 (IL-2), which are required for T-cell proliferation. FK506 has also been found to speed functional recovery and axonal regeneration in the rat in a dose-dependent manner following a sciatic nerve crush lesion.

U.S. Pat. No. 5,654,332 (Armistead et al.) discusses immunosuppressive FK506 analogs that bind FKBP-12, and are said to stimulate neurite outgrowth in the presence of NGF. The neurotrophic activity of these FKBP-12 binding compounds was said to be "directly related to their affinity for FKBP-12 and their ability to inhibit FKBP-12 rotamase activity" (id. at col. 7, lines 47–50). Rotamase activity measures peptidylisomerase cis-trans isomerization, and inhibition of this activity has been accepted as an indication of the immunosuppresant and neurotrophic activity of therapeutic agents. See U.S. Pat. No. 5,614,547 (Hamilton et al.).

Systemic administration of two synthetic FK506 analogs that bind FKBP-12 but that do not inhibit calcineurin activity (and which are not immunosuppressants) have been reported to increase the size of myelinated fibers (Gold et al., *Exp. Neurol.* 147:269–278, 1997; Steiner et al., *Nature Medicine* 3:1–8, 1997; Steiner et al., *Proc. Natl. Acad. Sci. USA* 94:2019–2024, 1997). It has also been reported that androgens and estrogens stimulate facial nerve regeneration in hamsters (e.g. Tanzer and Jones, *Exp. Neurol.* 146:258–264, 1997).

Many of the compounds previously shown to stimulate nerve regeneration have undesired side-effects, such as immunosuppression (FK506 and analogs that retain immunosuppressant activity) or androgenic or estrogenic stimulation. There is therefore a need to provide a class of nerve growth stimulating compounds that are well tolerated by subjects who take them.

SUMMARY OF THE INVENTION

The mechanism by which FK506 and other analogs induces nerve growth stimulation has previously been misunderstood, which has been an obstacle to the development of new drugs for this purpose.

The present invention takes advantage of the surprising discovery that nerve growth stimulation is promoted by disruption of the mature steroid receptor complex, and not by interaction with FKBP-12, as was previously thought. Disruption of the complex can include inhibition of physical assembly, promotion of disassembly, or functional interference with the steroid receptor complex, for example the mature steroid receptor complex, or a less mature form of the complex that is a predecessor to the mature complex. The participation of MAP kinase/kinase (MEK) in stimulating nerve growth, and the role heat plays in increasing neurite outgrowth when combined with nerve growth stimulating compounds, are additional parameters that can be exploited as part of this invention.

In view of the discovery of the biochemical mechanism by which neurite outgrowth is promoted, assays have been developed for selecting new compounds that may have activity in promoting nerve growth. Such assays may include determining if a test compound, other than a steroid ligand such as an androgen or an estrogen, disrupts assembly of the steroid receptor complex, and selecting a compound that disrupts assembly of the steroid receptor complex. Alternatively, the assay may include determining the ability of test compounds to stimulate MEK activity, and selecting compounds on this basis. Examples of specific classes of compounds that can be screened include geldanamycin and its structural analogs, rapamycin and its structural analogs, and FK506 and its structural analogs, radicicol and its analogs and bastadins and their analogs. Compounds selected by this assay for further investigation may be tested in additional assays to measure actual neurite outgrowth induced by the compound. In this way neurotrophic compounds have been identified by the assay for disruption of the steroid receptor complex or stimulation of MEK.

Methods have been designed for stimulating nerve cell growth in a subject by administering to the subject a compound (including a compound discovered by the assay) that disrupts assembly or function of the steroid receptor complex, for example of the mature steroid receptor complex, (for example by inhibiting association or promoting dissociation), or stimulates MEK activity, wherein the compound is other than a ligand for the steroid hormone binding portion of the steroid receptor complex (such as an androgen or an estrogen), and in some specific embodiments does not bind with high affinity to FKBP-12. A therapeutic amount of heat may be administered in combination with nerve growth stimulating compounds. In particular embodiments, the compound is administered to disrupt association of a p23 component of the steroid receptor complex with an hsp-90 component or disrupt association of FKBP-52 with hsp-90. In other embodiments, the compound is administered to competitively bind with ATP at an amino terminal ATP binding site of hsp-90, for example at a geldanamycin binding site of the steroid receptor complex. In yet other embodiments, the compound is administered to stimulate MEK activity. These methods include administration of a benzoquinone ansamycin, such as geldanamycin or a structural analog or mimetic thereof, an anti-FKBP-52 antibody, radicicol or a structural analog or mimetic thereof, or a bastadin or a structural analog or mimetic thereof. The method can also include administering a second neurotrophic factor, other than the compound that disrupts association of the steroid receptor complex.

The method is useful in the treatment of animals (including mammals such as humans) having a neurological condition associated with neuronal dysfunction caused by disease or injury to neurons in either the central or peripheral nervous systems. Compounds or compositions are administered, with or without heat, to the animal in a therapeutically effective neurotrophic amount to bind to the mature steroid receptor complex (for example at a geldanamycin binding site of hsp-90) to disrupt association of the mature steroid receptor complex or stimulate MEK activity, and promote neurite outgrowth from neurons. The method can also be used in association with procedures such as a surgical nerve graft, or other implantation of neurological tissue, to promote healing of the graft or implant, and promote incorporation of the graft or implant into adjacent tissue.

Certain pharmaceutical compounds that are not a ligand for the steroid hormone binding portion of the steroid receptor complex can disrupt assembly of a steroid receptor complex. These compounds can be geldanamycin and its structural analogs, rapamycin and its structural analogs, FK506 and its structural analogs, radicicol or a structural analog or mimetic thereof, or a bastadin or a structural analog or mimetic thereof, but more particular embodiments of the compound may have low rotamase inhibition activity, may be other than an FK506 or rapamycin analog, may not bind with high affinity to FKBP-12, or are not immunosuppressive. In particular embodiments, the compound specifically disrupts formation of the steroid receptor complex (for example the mature steroid receptor complex) either by inhibiting association or promoting dissociation of the steroid receptor complex, for example by disrupting association of a p23 component of the steroid receptor complex with an hsp-90 component, or disrupting association of FKBP-52 with hsp-90, or inhibiting interaction of p23, FKBP-52 or hsp-90 with the complex. Certain embodiments of the compound competitively bind with ATP at an amino terminal ATP binding site of hsp-90, which is also the binding site for geldanamycin binding to the steroid receptor complex. In particular embodiments the compound is radicicol or a radicicol analog that binds to a geldanamycin binding site of hsp-90. In other embodiments, the compound is an anti-FKBP-52 antibody, or another agent that specifically causes FKBP-52 to dissociate from hsp-90 of the steroid receptor complex.

The compound can be incorporated into a pharmaceutical composition, which can also include another neurotrophic factor, such as NGF, IGF-1, αFGF, βFGF, PDGF, BDNF, CNTF, GDNF, NT-3, NT 4/5, and mixtures thereof, or a steroid hormone that is a ligand of the steroid receptor complex (such as an estrogen, an androgen or a corticosteroid such as dexamethasone).

In a more specific aspect, the compound is a nerve growth stimulating amount of an agent that binds to a polypeptide of a steroid receptor complex other than a steroid hormone binding portion of the complex, the agent being selected from the group consisting of an FK506 analog having low binding affinity for FKBP-12 and low rotamase activity, for example a benzoquinone ansamycin and structural analogs thereof, a peptide comprising a sequence of a selected polypeptide component of the complex at a site of interaction between the selected component and another polypeptide component of the complex, an antibody, and combinations thereof, wherein the agent disrupts assembly or interferes with function of the steroid receptor complex by causing p23 or FKBP-52 dissociation from the complex, or inhibiting p23 or FKBP-52 association with the complex, or inhibiting interaction of p23, FkBP-52 or hsp-90 with the complex.

Compounds of the present invention need not have significant calcineurin inhibition or rotamase inhibition. The compounds may have an $IC_{50}$ for rotamase inhibition of greater than 1 nM, for example greater than 10 nM, 25 nM, or even 50–100 nM.

Nerve cell growth can be stimulated in a subject by administering to the subject a compound that stimulates nerve cell growth, wherein the compound is one or more of radicicol or its analogs; a bastadin or its analogs; or an agent that stimulates MAP kinaseikinase activity. In particular embodiments, the compound is a radicicol analog, or a bastadin such as bastadin 1, 2, 3, 4, 5, 6, 7, 8, 9, 10, 11, 12, 13, 14, 15, 16, 17, 18, 19, or 20, particularly bastadin 10, or an analog of a bastadin.

The method also includes administering radicicol or its analogs, or the bastadin or its analogs, in combination with a neurotrophic factor other than the compound that disrupts association of the mature steroid receptor complex or stimulates MAP kinase/kinase activity. The neurotrophic factor may be, for example, NGF, IGF-1, α-FGF, β-FGF, PDGF, BDNF, CNTF, GDNF, NT-3, NT 4/5, and mixtures thereof.

Another aspect is screening for agents that stimulate nerve cell growth, by detecting agents that stimulate MAP kinase/kinase activity, such as radicicol analogs, or platelet derived growth factor BB (PDGFBB) or analogs thereof.

The method also includes applying a sufficient amount of heat to an area where nerve cell growth is desired, for example along a normal anatomic pathway, or in an anatomic region, of a transected, partially transected or otherwise damaged nerve. Alternatively, the body temperature of a subject can be systemically elevated, for example by inducing a fever or placing the body in a heated environment. The invention can also include providing a template in an area where nerve growth is desired, for example a tubular member that defines an anatomical pathway along which nerve growth is desired. If desired, a therapeutically effective amount of the neurotrophic compound may be provided in association with the template to promote nerve growth. The template may be placed between opposing ends of a transected or partially transected nerve. Heat can be applied to the template in a therapeutically sufficient amount, effective to enhance nerve growth. Alternatively, the template along the desired anatomical path can be impregnated with the neurotrophic compound, or the impregnated template can be heated.

In some embodiments, the radicicol compound or its analogs are of the formula:

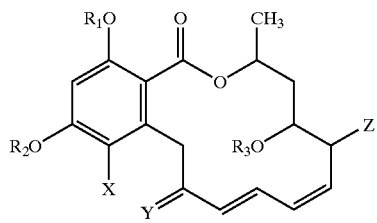

where X, Y, Z, R1, R2 and R3 are as defined in Example 14, and in particular embodiments is not radicicol.

In some embodiments, the neurotrophic compound is a complete bastadin or bastadin analog, such as,

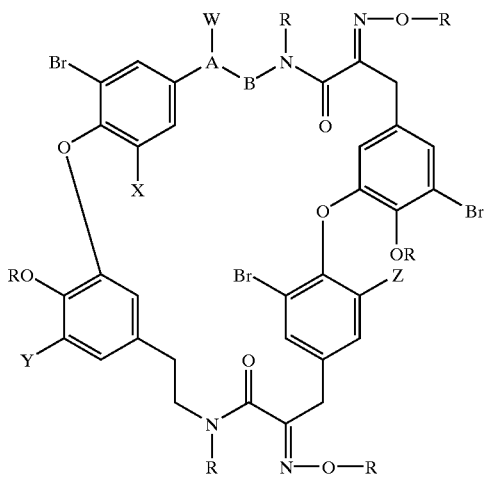

where each R is independently selected from the group consisting of H, C1–8 alkyl, or sulfato, W is selected from the group consisting of H, OH, or C1–8 alkoxy, X, Y, and Z are independently selected from the group consisting of hydrogen, halogen, hydroxyl, or C1–8 alkoxy, and A and B are carbon atoms that are joined by a single or a double bond. Specific complete bastadin structures (which also show the naturally occurring bastadin macrocylic ring structures) are found in Example 15.

Also included are hemibastadins and their analogs, of the formula

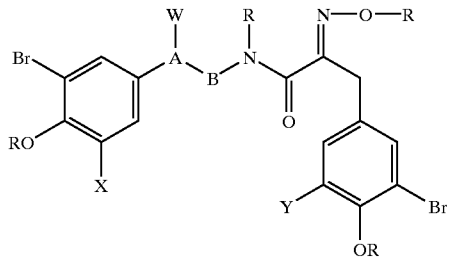

where A, B, R, W, X, and Y are defined as above for the complete bastadins. Specific hemibastadin structures are found in Example 15.

Also included are hemibastadinols and their analogs of the formula

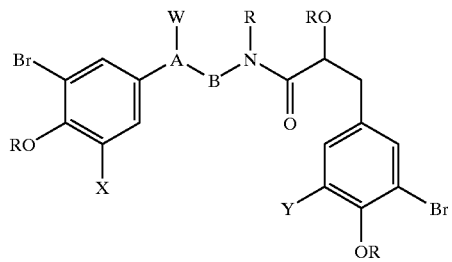

where A, B, R, W, X, and Y are defined as above for the complete bastadins. Specific hemibastadinol structures are found in Example 15.

In other embodiments, the compound is a bastadin subunit such as

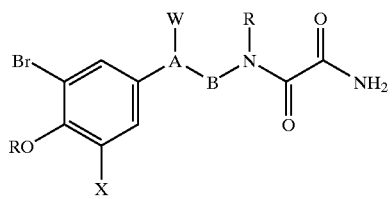

where A, B, R, W, and X are defined as above for the complete bastadins. A specific example of a bastadin subunit is shown in Example 15.

The foregoing and various features and advantages of the invention will become more apparent from the following detailed description and accompanying drawings.

DETAILED DESCRIPTION OF PARTICULAR EMBODIMENTS

Steroid receptors are part of a superfamily of molecules that regulate gene expression by direct interaction with the upstream region of specific structural genes. It is essential to hormone action that a receptor must be able to assume both an active and an inactive state. This regulation is accomplished by association of the receptor (the steroid ligand binding component) with a multimeric complex of chaperone proteins, such as heat shock proteins (hsp-90), p23 and FKBP-52, which form the steroid receptor complex (SRC). When the steroid receptor binds its ligand, the receptor is activated, the chaperone proteins of the SRC are dissociated, and a DNA binding domain of the receptor is exposed for interaction with gene regulatory sequences. Members of the steroid receptor family that are regulated in this fashion include mineralocorticoids (such as aldosterone), glucocorticoids (such as dexamethasone), progestins (such as progesterone), androgens (such as testosterone), and estrogens (including estrogen, β-estriol and β-estradiol).

Figure 1:
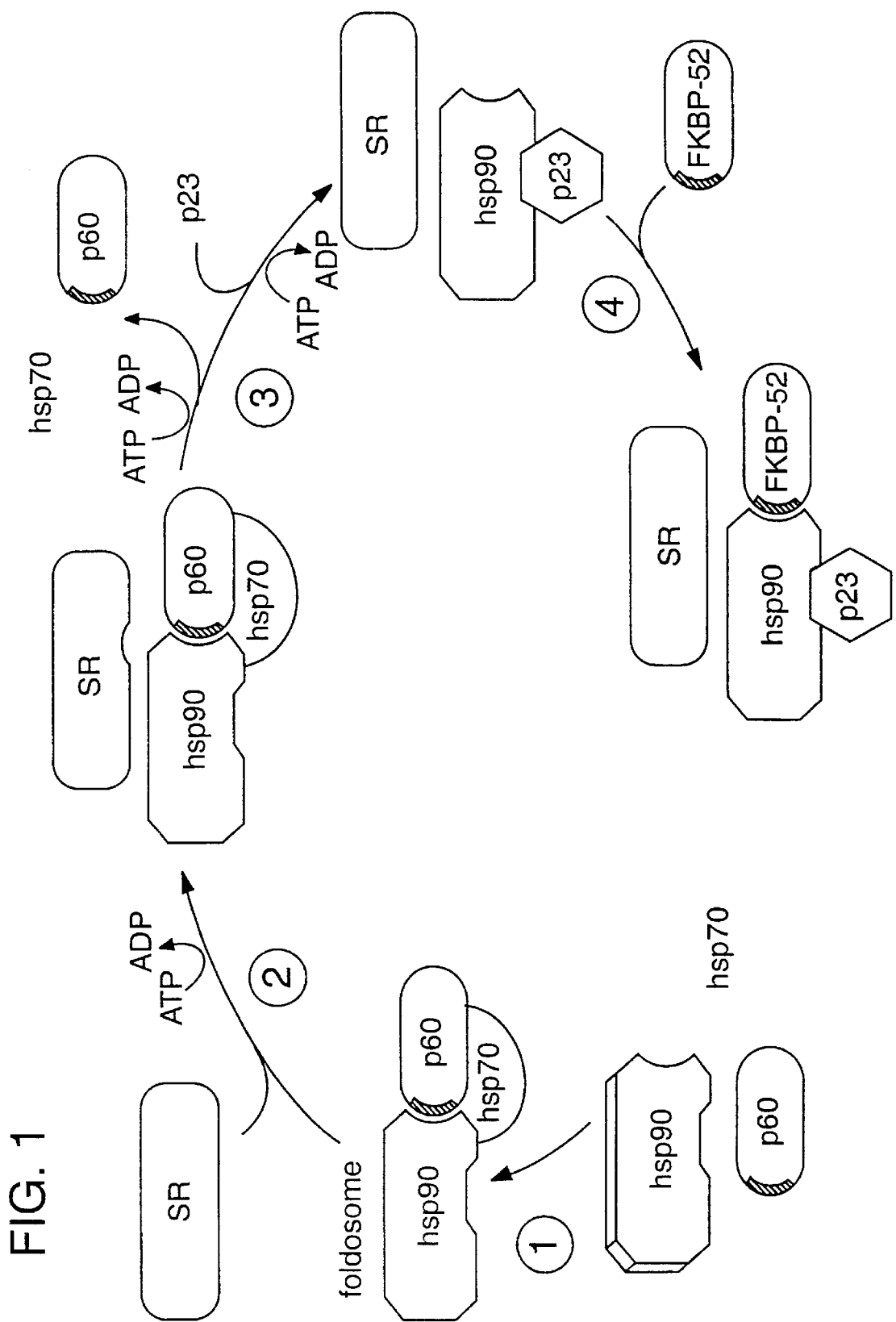
FIG. 1 is a schematic diagram illustrating receptor-hsp-90 heterocomplex assembly of the steroid receptor complex.

A model of steroid receptor complex assembly is shown in FIG. 1. ATP-dependent association of the steroid receptor SR with the hsp-90/p60/hsp-70 folding complex (foldosome) yields an intermediate (SR/hsp-90/p60/hsp-70) complex that is unstable in the absence of p23 or molybdate. Once p23 has associated with the complex, and hsp-90 binds tetratricopeptide repeat (TPR) domain proteins, such as the immunophilins (e.g. FKBP-52 and CyP40), the nearly mature, metastable SRC is formed (SR/hsp-90/p23/FKBP-52). In FIG. 1, the TPR domain is indicated by the solid black crescent to which FKBP-52 is bound. Assembly of the mature steroid receptor complex is the last step shown in FIG. 1, in which the complex of chaperone proteins hsp-90/p23/FKBP-52 is assembled with the steroid receptor SR.

The immunophilins are a highly conserved family of chaperone proteins that are known to be mediators of immunosuppressant drug activity. The best characterized immunophilin is FKBP-12, which interacts with the immunosuppressant drug FK-506 in T lymphocytes, to prevent calcineurin from dephosphorylating the nuclear factor of activated T-cells (NF/AT), thereby blocking synthesis and secretion of cytokines required for immune function. Immunophilins have peptidylisomerase (PPIase) activity, and inhibitors of this activity can be detected with a rotamase assay which measures inhibition of cis-trans isomerization of the peptidylprolyl. However, FKBP-12 immunosupression is not mediated by an ability to inhibit rotamase activity. Rotamase activity has nonetheless been accepted as an indication of immunosuppressant activity of immunophilins, even though it does not measure the dephosphorylation of calcineurin activity by which immunosuppression is actually mediated. Previous researchers had taken advantage of the rotamase assay to look for FKBP-12 binding drugs that would promote nerve regeneration (as FK506 had been found to do).

The present invention takes advantage of the surprising finding that disrupting assembly of the SRC, and not binding to FKBP-12, is what promotes nerve regeneration. Hence previous efforts to find FKBP-12 analogs that promote nerve regeneration by measuring rotamase or immunosuppressive activity was misdirected, and was likely to find drugs that had unwanted side effects (such as immunosuppression and cardiomyopathy). The present invention has taken advantage of the discovery of the actual biological mechanism by which nerve regeneration is promoted to provide a superior assay for finding new neurotrophic drugs that are superior to those in the prior art.

One such new compound is geldanamycin, a benzoquinone ansamycin antibiotic, which binds in a pharmacologically specific manner to hsp-90 (Whitesell et al., *Proc. Natl. Acad. Sci. USA* 91:8324–8328, 1994) and inhibits association of the p23 component of the heterocomplex assembly system with hsp-90 (Johnson and Toft, *Mol. Endocrinol.* 9:670–678, 1995). Geldanamycin and radicicol thereby promote dissociation of a steroid receptor complex, and block reassembly of the hormone-responsive form of the complex, preventing hormone activation and ultimately resulting in the degradation of the hormone receptor. Geldanamycin blocks assembly of the progesterone receptor (PR) complex (Smith et al., *Mol. Cell. Biol.* 15:6804–6812, 1995) and of the glucocorticoid receptor (GR) complex (Czar et al., *Biochem.* 36:7776–7785, 1997) at an intermediate stage of assembly where the hormone binding domain is not properly folded and therefore cannot bind steroid with high affinity (for example, does not bind steroid ligand that is present in concentrations of less than about 10 nM). Geldanamycin also is known to act on estrogen and androgen hormone receptors (Smith et al., *Mol. Cell. Biol.* 15:6804–6812, 1995; Nair et al., *Cell Stress and Chaperones* 1:237–250, 1996). Transformation of GR and PR as measured either by 9S to 4S conversion, or by acquisition of DNA-binding activity, is correlated with dissociation of steroid receptors from hsp-90 (see, e.g., Meshinchi et al., *J. Biol. Chem.* 265:4863–4870, 1990; Kost et al., *Mol. Cell. Biol.* 9:3829–3838, 1989).

Another class of neurotrophic agents that have been found in accordance with the invention are those that act at the FKBP-52 component of the SRC. It has surprisingly been found that the action of the neurotrophic immunosuppressant FKS506 is via an interaction with FKBP-52, which induces a conformational change in hsp-90, enabling dissociation of p23 from hsp-90, thereby interfering with assembly of the mature SRC. The present invention also includes bastadins that may disrupt the SRC by binding to FKBP-52. Mack et al. have shown that bastadin 5 stimulates [$^3$H] ryanodine binding to ryanodine receptors, but that such stimulation is antagonized by FK506. (Mack et al., *J. Biol. Chem.,* 269(37) pp. 23236–49, 1994). The model in FIG. 2 of the present application shows how FK506 binds to FKBP-52. By competing with bastadin 5 for this binding site or by inducing changes in the conformation of FKBP-52, FK506 may block the action of bastadin 5.

Figure 10:
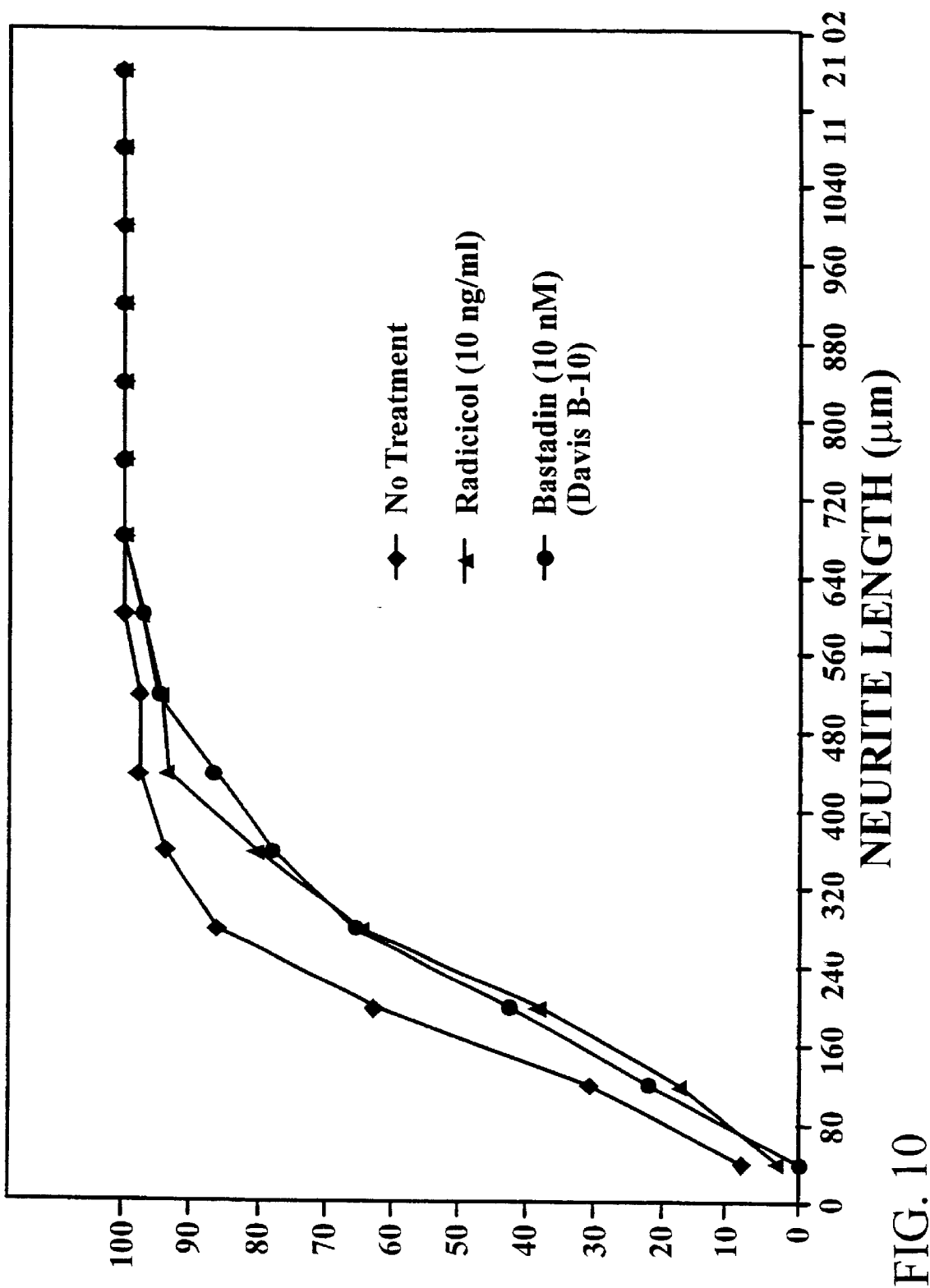
FIG. 10 is a cumulative histogram of neurite outgrowth lengths for hippocamapal cells after 72 hours when untreated and treated with either radicicol or a bastadin 10 analog.

As shown in FIG. 10, bastadin 10 stimulates neurite outgrowth.

An anti-FKBP-52 antibody also inhibits assembly of the mature SRC. Binding of FK506 to GR-associated FKBP-52 causes increased nuclear translocation of GR in response to dexamethasone and potentiation of GR-mediated gene expression (Sanchez and Ning, *METHODS: A Companion to Meth. Enzymol.* 9:188–200, 1996).]

FKBP-52 and CyP40 bind directly to hsp-90, and CyP40 competes for FKBP-52 binding to hsp-90 and vice versa.

CyP40 is an example of a protein targeted by cyclosporin A (CsA) and its analogs. These immunophilins bind hsp-90 in a mutually exclusive fashion, leading to the formation of separate CyP40-hsp90 and FKBP-52-hsp-90 complexes (Ratajczak and Carrello, *J. Biol. Chem.* 271:2961–2965, 1996). Immunophilins such as FKBP-52, CyP40 and PP5 and non-immunophilin proteins such as p60 and Mas70p, have one or more tetratricopeptide repeat (TPR) domains (Ratajczak et al., *J. Biol. Chem.* 268:13187–13192, 1993) that bind to the TPR-binding domain of hsp-90. An increased number of TPR domains in a protein appears to correlate with increased hsp-90-binding affinity. Hence peptides having one or more TPR domains would be expected to have increased hsp-90 binding affinity, and would interfere with FKBP-52 association with hsp-90, which is required for assembly of the mature steroid receptor complex.

For example, binding of both FKBP-52 and CyP40 to hsp-90 is competitively inhibited by a purified fragment of human CyP40 comprising its three TPR domains, and by a fragment of rat PP5 comprising its four TPR domains (reviewed in Pratt and Toft, *Endocrine Rev.* 18:306–360, 1997). Such purified fragments, or other peptides such as PP5, p60 and Mas70, containing one or more TPR domains (particularly two, three or more TPR domains) are therefore suitable for interfering with assembly or function of the steroid receptor complex, and are included within the scope of this invention.

The effects of radicicol, radicicol analogs, bastadins, bastadin analogs, geldanamycin and the other neurotrophic agents that do not bind directly to the steroid binding domain of the steroid receptor complex are believed to result from binding of these compounds to components of steroid receptor complexes, causing the dissociation of hsp-90 from the steroid receptor complex either directly (by binding to hsp-90 or interfering with the binding of hsp-90 to the steroid receptor) or indirectly (by binding to a polypeptide such as FKBP-52 that itself binds to hsp-90, or a polypeptide that binds to p23), or alternatively by preventing association of hsp-90 or p23 with the steroid receptor complex. Interference with the ability of hsp-90 to complex with and perform its chaperone function for other hsp-90 substrate proteins is believed to also be responsible for or contribute to the observed stimulation of nerve regeneration by FK506 and/or geldanamycin. Any agent that interferes with the function of the mature steroid receptor complex (including interference with a precursor of the mature complex, such as the nearly mature complex or foldosome) is also included in the scope of this invention. Also included in the scope of this invention are compounds that stimulate MAP kinase/kinase.

Specific embodiments of the neurotrophic compounds of this invention can be substantially free of calcineurin inhibition, and can have low rotamase inhibition, for example an $IC_{50}$ of greater than about 1 nM, or even 5 or 10 nM.

Identification of the role that MAP kinase/kinase (MEK) plays in stimulating neurite outgrowth also provides a basis for screening compounds that may stimulate nerve growth. Compounds which stimulate MEK activity are included in the scope of the invention.

Abbreviations and Definitions

AR: Androgen Receptor
ER: Estrogen receptor
GR: Glucocorticoid receptor
PR: Progesterone receptor SRC: Steroid receptor complex. A multiprotein complex associated with any steroid receptor, including, but not limited to, the progesterone receptor, glucocorticoid receptor, estrogen receptor, androgen receptor, and mineralocorticoid receptor.

TPR: Tetratricopeptide repeats are Domain III of FKBP-52; TPRs were first identified by Sikorski et al., Cell 60:307–317, 1990, as degenerate consensus sequences of 34 amino acids.

Mimetic: A biological compound (such as a peptide) that mimics the effect of a pharmaceutical, for example a peptide that mimics the effect of a benzoquinone ansamycin by binding to a geldanamycin binding site on hsp-90.

Ligand for the steroid hormone binding portion of the steroid receptor complex: An already recognized ligand for the receptor subtype. For example, dexamethasone for the GR, estrogen for the ER, testosterone for the AR, progesterone for the PR.

Immunophilins: A highly conserved family of chaperone proteins that have PPIase activity, producing cis-trans isomerization. The immunophilins are divided into low molecular weight (less than 40 kD) and high molecular weight (40–65 kD) immunophilins. The high molecular weight immunophilins (e.g., FKBP-52), in contrast to FKBP-12, contain three or more tetratricopeptide repeats (TPRs) which mediate binding to hsp-90. The immunophilins may be subdivided into two classes on the basis of their ability to bind either cyclosporin A (cyclophilins) or FK506 and rapamycin (the FK binding proteins, FKBPs). Members of the FKBP family of immunophilins include FKBP-12, FKBP-13, FKBP-25, FKBP-52 (also referred to as FKBP-59), and FKBP-65. PP5 is also considered a member of this family, because it binds FK506 weakly, as reported by Silverstein et al., *J. Biol. Chem.* 272:16224–16230, 1997.

NGPA: Nerve growth promoting agent. A "nerve growth promoting agent" or NGPA is defined as a substance that binds to a polypeptide component of a steroid receptor complex, such components including but not limited to hsp-90 and FKBP-52, and promotes nerve regeneration, without limitation to a particular mechanism of action. In particular embodiments, the NGPA does not bind FKBP-12 (or binds it with low affinity, with a Kd of greater than 1 $\mu$M), has low rotanase inhibitory activity (an apparent Ki of more than 2500 nM), binds with low affinity to calcineurin (requires concentrations greater than 30 $\mu$M to bind), or is non-immunosuppressive, as measured by the substantial absence of a drop in total blood lymphocyte counts in subjects to whom the agent is administered. NGPAs include, but are not limited to, non-FKBP12-binding ("non-binding") or low affinity FKBP-12 binding analogs of FK506; benzoquinone ansamycins, including geldanamycin, naturally occurring analogs of geldanamycin, including, but not limited to, herbimycin A and macbecin (DeBoer et al., *J. Antibiot.* (Tokyo) 23:442–447, 1970; Omura et al., *J. Antibiot.* (Tokyo) 32:255–261, 1979; Ono et al., *Gann.* 73:938–944, 1992), and structural analogs and derivatives thereof, such as geldampicin, tunicamycin, and dihydrogeldanamycin, as well as the compounds listed in Example 12; peptides, including an amino acid sequence of a particular polypeptide component of a steroid receptor complex at a site of interaction between that component and another component of the complex (such as the TPR domain), which interferes or competitively binds with the component of the SRC; and antibodies that bind specifically to polypeptide components of steroid receptor complexes, e.g., anti-hsp-90, anti-FKBP-52, etc.) that interfere with the interaction of the bound polypeptide with another polypeptide in the steroid receptor complex. The neurotrophic agents include compounds that either physically disrupt association of the mature SRC (either by inhibiting association or promoting dissociation of the SRC), or inhibit interaction of components (such as p23, FKBP-52 or hsp-90) of the SRC. Further, the neurotrophic agents include compounds which stimulate MAP kinase/konase (MEK) activity. Heat applied for physiologically tolerable periods to boost a mammal's body temperature to a physiologically tolerable temperature in combination with administering compounds which stimulate nerve growth is yet another neurothophic agent.

Neurotrophic: Promoting nerve growth.

Transformation: conversion of the 9S non-DNA-binding form of a steroid receptor complex to the 4S DNA-binding form. The term "activation" refers to the conversion of a steroid receptor from a form that does not bind steroid ligand to a steroid-ligand-binding form.

Rotamase Activity: Rotamase (PPIase) activity can be determined, for example, as in WO 92/04370, and can be expressed as a $K_i$. The cis-trans isomerization of the alanine-proline peptide bond in a model substrate, N-succinyl-Ala-Ala-Pro-Phe-4-nitroanalide, may be monitored spectrophotemetrically in a coupled assay with chymotrypsin, which releases 4-nitroanalide from the trans form of the substrate. The inhibitory effect upon the addition of different concentrations of inhibitor on the extent of the reaction is determined, and analysis of the change in the first order rate constant as a function of inhibitor concentration yields an estimate of the apparent $K_i$. In the assay of the present invention, rotamase activity has been found to be unrelated to the neurotrophic activity of the compounds, and need not be determined.

"Known" or "recognized" compounds (such as FKBP-12 binding compounds or FK506 analogs) are those that have previously been reported in patents or publications, or that otherwise qualify as prior art.

Analogs are structurally similar compounds that retain biological activity of the parent compound, such as stimulation of neurite outgrowth.

EXAMPLE 1

Assays for Identifying Nerve Growth Promoting Agents

There are a number of well-known methods for assaying compounds that bind to hsp-90, FKBP-52, and other polypeptide components of a steroid receptor complex that can be used as an initial screen for candidate compounds that stimulate nerve regeneration. Compounds can subsequently be tested in vitro or in vivo for activity in stimulating nerve regeneration.

Examples include assays for the binding of a test compound to a polypeptide that is a component of a steroid receptor complex. An assay for detecting binding to hsp-90 is described, for example, by Whitesell et al. (*Proc. Nail. Acad. Sci. USA* 91 :8324–8328, 1994). Commercial hsp-90 (StressGen Biotechnologies, Victoria, BC) dissolved in 20 µg/mL of TNESV buffer (50 mM Tris-HCl, pH 7.4/1% Nonidet P-40/2 mM EDTA/100 mM NaCl/1 mM orthovanadate/1 mM phenylmethylsulfonyl fluoride/20 µg leupeptin per mL/20 µg of aprotinin per ml) and the test compound are incubated for 45 min at 4° C. with geldanamycin immobilized on a conventional solid support, e.g., geldanamycin-coupled agarose beads (Whitesell et al., *Proc. Natl. Acad. Sci. USA* 91:8324–8328, 1994). The beads are then washed with TNESV buffer and bound hsp-90 is eluted by heating in reducing loading buffer, and can be analyzed by SDS/PAGE and silver staining (Bio-Rad). Alternatively, if the hsp-90 is labeled, the assay can be performed for the bound label instead of the free label. Test compounds that compete with geldanamycin for binding to hsp-90 inhibit the binding of solubilized hsp-90 to the beads.

Similar assays can be performed to identify compounds that bind other steroid receptor complex polypeptide components. Binding to FKBP-52 can be assayed using recombinant FKBP-52 (Peattie et al., *Proc. Natl. Acad. Sci. USA* 89:10974–10978, 1992). Binding to p23 can be assayed using recombinant human p23 (Johnson et al., *Mol. Cell. Biol.* 14:1956–1963, 1994) and immobilized hsp-90. Purified hsp70 and recombinant p60 (Dittmar et al., *J. Biol. Chem.* 271: 12833–12839, 1996) are also available for use in such binding assays.

Immunoassays can also be performed using conventional immunoassay methodologies and antibodies that are specific for steroid receptor complex components, e.g., antibodies against FKBP-52 (Tai et al., *Biochem.* 25:5269–5275, 1986), hsp-90 (Sanchez et al., *J. Biol. Chem.* 260:12398–12401, 1985; Catelli et al., *EMBO J.* 4:3131–3135, 1985; Schuh et al., *J. Biol. Chem.* 260:14292–14296, 1985), hsp70 (a serum that also recognizes hsp-90)(Erhart et al., *Oncogene* 3:595–603, 1988), and p23 (Johnson et al., *Mol. Cell. Biol.* 14:1956–1963, 1994).

A well-accepted qualitative assay for receptor transformation, which involves dissociation of hsp-90 from the receptor complex, is conversion of a receptor complex to a state that binds polyanions such as phosphocellulose (Kalimi et al., *J. Biol. Chem.* 250:1080–1086, 1975; Atger and Milgrom, *Biochem.* 15:4298–4304, 1976), ATP-Sepharose (Toft et al., *J. Steroid Biochem.* 7:1053–1059, 1976; Miller and Toft, *Biochem.* 17:173–177, 1978), and carboxymethol-Sephadex (Milgrom et al., *Biochem.* 12:5198–5205, 1973; Parchman and Litwack, *Arch. Biochem. Biophys.* 183:374–382, 1977).

An in vitro assay for nerve cell growth (neurite outgrowth) is provided in Example 2, and in Gold et al., *Exp. Neurol.* 147:269–278, 1997. In vivo assays for nerve regeneration are discussed in, for example, Gold et al., *Restor. Neurol. Neurosci.* 6:287–296, 1994; Gold et al., *J. Neurosci.* 15:7505–7516, 1995; Wang et al., *J. Pharmacol. Exp. Therapeutics* 282:1084–1093, 1997; Gold et al., *Exp. Neurol.* 147:269–278, 1997 and Gold et al., *Soc. Neurosci. Abst.* 23:1131, 1997, which examine the effects of systemic administration of a test compound on nerve regeneration and functional recovery following a crush injury to the rat sciatic nerve. The sciatic nerves of anaesthetized rats are exposed, and the nerves crushed using forceps at the level of the hip. Following the sciatic nerve crush, the test compound is administered to the rats, e.g., by subcutaneous injection or oral administration. Functional recovery is assessed by determining the number of days following nerve crush until the animal demonstrates onset of an ability to right its foot and move its toes, and the number of days until the animal demonstrates an ability to walk on its hind feet and toes.

Nerve regeneration is also assessed by sampling tissues from the sciatic nerve at known (0.5 cm) distances from the crush site and counting the number of myelinated fibers by light microscopy. The size of axons is calculated by electron microscopy. Axonal areas of both myelinated and unmyelinated fibers are determined by tracing the axolemma using a digitizing tablet connected to a computer with appropriate software. Cumulative histograms are constructed from these data and mean values and standard errors are calculated to assess the effect of administration of the test compound on axonal areas.

EXAMPLE 2

FK506 and Geldanamycin Promote Nerve Regeneration by a Common Mechanism

This Example illustrates that FK506 and geldanamycin promote nerve regeneration by a common mechanism. SH-SY5Y human neuroblastoma cells were maintained in DMEM medium (GIBCO) supplemented with 10% fetal calf serum (SIGMA), 50 IU/mL penicillin, and 50 mg/mL streptomycin (GIBCO) at 37° C. in 7% $CO_2$. Cells were plated in six-well plates at $1 \times 10^6$ cells/well and treated with 0.4 mM aphidicolin (SIGMA). At five days, cells were washed, treated with nerve growth factor (NGF) (Boehringer Mannheim, Indianapolis, Ind.) at 10 ng/mL (to induce process outgrowth) in the presence or absence of FK506 (1 and 10 nM) (Calbiochem-Novabiochem Int'l., La Jolla, Calif.) and/or geldanamycin (0.1, 1, and 10 nM) (Calbiochem-Novabiochem, La Jolla, Calif.) dissolved in the DMEM medium. Media was changed at 96 hours and replaced with fresh media containing the compounds (NGF plus FK506 and/or geldanamycin) for an additional 72 hours (total time, 168 hours). The top 50% of axonal lengths were selected for statistical analysis. All experiments were run in duplicate wells and repeated at least twice for reproducibility.

For analysis of neurite process length of cells, 20 fields per well were randomly photographed at 72 and 168 hours. Neurite lengths were measured on photographic prints using a Houston Instrument HI-PAD digitizing tablet connected to an IBM XT computer with appropriate software (Bioquant IV, R&M Biometrics, Nashville, Tenn.); only those processes greater than two times the cell body length were measured. Data from identically treated wells were not different and were therefore combined. Mean values and histograms were constructed from these data. Histograms were compared using a Mann-Whitney U test, which makes no assumptions about the shape of the distribution.

The mean lengths of neuritic processes of untreated and treated cells are shown in Table 1:

TABLE 1

Mean Length of Top 50% of Neuritic Processes 168 Hours After Treatment with Geldanamycin in the Presence of NGF

| Treatment | Mean Length ($\mu$M) | S.E.M. |
| --- | --- | --- |
| Untreated | 83.22 | 2.50 |
| NGF (10 ng/mL) | 107.98 | 4.52 |
| Geldanamycin (1 nM) + NGF (10 ng/mL) | 128.00 | 4.72 |
| Geldanamycin (10 nM) + NGF (10 ng/mL) | 109.62 | 4.20 |
| FK506 (10 nM) + NGF (10 ng/mL) | 155.64 | 5.40 |
| Geldanamycin (1 nM) + FK506 (10 nM) + NGF (10 ng/mL) | 145.26 | 4.02 |
| Geldanamycin (10 nM) + FK506 (10 nM) + NGF (10 ng/mL) | 134.82 | 3.34 |

Geldanamycin and FK506 each stimulate neurite outgrowth in a concentration dependent manner. The similar neurotrophic effects of geldanamycin and FK506, their additive effects at very low concentrations (e.g. 0.1 nM; data not shown), and their inhibitory effects at high concentrations (like high concentrations of either compound alone) demonstrate that the two compounds act on nerve cells to promote nerve outgrowth by a common mechanism. As the following examples will illustrate, that mechanism has now been found to involve an interaction of both compounds with components of the steroid receptor complex. FKBP12 does not appear to have a role in the stimulation of neurite outgrowth by either geldanamycin or FK506.

Cell lines other than the SH-SY5Y human neuroblastoma cells can be used in the nerve growth assays. Examples of suitable other cell lines include PC-12 (rat pheochromocytoma), LA-N-5 cells (human neuroblastoma cells less differentiated than SY5Y cells), and Neuro-2a and NS20Y cells (mouse neuroblastoma).

EXAMPLE 3

FKBP-12 Knockout Mice Demonstrate FKBP-12 Not Involved in Neurotrophic Activity

FKBP-12 knockout mice (Shou, et al., *Nature* 391:489, 1998) were used to test whether FKBP-12 is necessary for FK506's ability to increase nerve elongation. Such mice usually die from severe cardiomyopathy between embryonic day 14.5 (E14.5) and birth, consistent with the known association between FKBP-12 and calcium release channels. No gross pathology has been noted in brains of these mice. Primary neuronal hippocampal cultures were prepared from E18.5 homozygote FKBP-12 knockout and wild-type mice. No difference was found in FK506's regenerative-promoting response of neurons in FKBP-12 knockout and wild-type mice. Mean axonal lengths of hippocampal neurons were not significantly different between FKBP-12 knockout and wild-type mice in drug-free cell cultures (203±9.5 and 219±8.0, respectively; mean±S.E.M.) [two-way ANOVA and Scheffe's test of least significant differences; p=0.68, df=230)] or FK506-treated cultures (264±18.2 and 276±11.1, respectively) [two-way ANOVA and Scheffe's test of least significant differences; p=0.94, df=112)].

FK506 elicited a similarly significant increase over non-treated values in cells from FKBP-12 knockout [two-way ANOVA and Scheffe's test of least significant differences; p<0.006, df=144] and wild-type mice [two-way ANOVA and Scheffe's test of least significant differences; p<0.002, df=198]; i.e., 30% and 26%, respectively. Thus, neuronal cells from FKBP-12 knockout mice retain their responsiveness to the neurite outgrowth-promoting property of FK506. FKBP-12 is therefore not required for FK506 to promote neurite outgrowth in vitro.

EXAMPLE 4

FKBP-52 Blocks FK506 Neurotrophic Activity

Neuroblastoma SH-SY5Y cells were used to examine human neurite outgrowth in vitro and to explore which neuroimmunophilin mediates the effect. SH-SY5Y cells do not extend processes in the absence of exogenous nerve growth factor (NGF), with optimal neurotrophic activity at 10 ng/ml NGF. Initial studies showed that FK506 increases neurite outgrowth in SH-SY5Y cells in a concentration-dependent manner. Cumulative histograms of neurite lengths show that 10 pM–10 nM FK506 significantly [Mann-Whitney U test ($\alpha$=0.05)] increases neurite outgrowth. However, 100 nM was less effective and, at 1000 nM or greater concentrations, neurite outgrowth was inhibited.

The involvement of FKBP-52 was demonstrated using a mouse monoclonal antibody, FKBP-52 Ab (StressGen Biotechnologies Corp., British Columbia, Canada) that does not interact with FKBP-12. To get the antibody into the cells, SH-SY5Y cells were permeabilized with saponin (30 μg/μl) for 10 min in the presence of the antibody; preliminary experiments showed that saponin treatment did not alter the response of the cells to NGF alone. The FKBP-52 antibody significantly [Mann-Whitney U test ($\alpha=0.05$)] blocked the ability of FK506 (1 and 10 nM) to promote neurite outgrowth from SH-SY5Y cells in a concentration-dependent manner between 50 and 100 nM. Cumulative histograms of neurite lengths show that 100 nM FKBP-52 antibody completely blocks the action of FK506 at these concentrations. Surprisingly, the antibody blocked not only the effect of FK506 but also NGF's effect, suggesting a convergence of their signal transduction pathways perhaps involving the MAP kinase pathway (ERK2). Regardless of the underlying mechanism involved, FK506's neurite outgrowth-promoting property is totally dependent on its interaction with the immunophilin FKBP-52.

EXAMPLE 5

FKBP-52 Antibody Promotes Neurite Outgrowth

The FKBP-52 antibody (FKBP-52 Ab) itself possesses agonistic properties on neurite outgrowth. Cumulative histograms of neurite lengths show that FKBP-52 Ab significantly [Mann-Whitney U test ($\alpha=0.05$)] shifted the distribution of neurite lengths to the right in a concentration-dependent manner, indicating longer processes. In fact, the FKBP-52 Ab elicited even longer neurites per unit time than those maximally observed with FK506 (10 nM), producing some of the fastest growing neurites found to date (maximal length, 880 μm). These findings demonstrate that it is possible to develop compounds which can distinguish between FKBP-52 and FKBP-12 (i.e., do not substantially bind to both immunophilins) while maintaining the ability to increase neurite outgrowth. This finding enables the development of a new class of neuroimmunophilin ligands: neuroimmunophilin compounds, having low or absent FKBP-12 binding affinity, which specifically bind to components of the SRC, and increase nerve regeneration by interacting selectively with FKBP-52 (or other components of the SRC, such as p23 or hsp-90)

The synthetic glucocorticoid dexamethasone and β-estradiol both significantly increased neurite outgrowth in SH-SY5Y cells in a concentration-dependent manner. β-Estradiol (50 nM) produced a significantly [Mann-Whitney U test ($\alpha=0.05$)] greater positive effect on neurite outgrowth than dexamethasone (50 nM), suggesting a greater involvement of the estrogen receptor complex in SH-SY5Y cells. This is supported by the data also showing that the combination of β-estradiol and FK506 did not produce a further significant [Mann-Whitney U test ($\alpha=0.05$)] increase in neurite outgrowth, indicating that these compounds act at the same steroid receptor sub-type. In contrast, the combination of dexamethasone and FK506 produced neurites (maximal length, 960 μm) that grew at least as, if not more, rapidly than those under FKBP-52 antibody modulation, indicating that dexamethasone and FK506 act at different steroid receptor sub-types. Taken together, the finding that maximal neurite outgrowth elicited by FK506 and β-estradiol is not additive suggests the estrogen receptor complex plays a greater role than the glucocorticoid receptor complex in human SH-SY5Y neurite outgrowth promotion by FK506.

EXAMPLE 6

Geldanamycin Promotes Neurite Outgrowth by Disruption of Steroid Receptor Complex SH-SY5Y cells were treated with geldanamycin, a benzoquinone antibiotic that blocks the reassociation of the mature steroid complex (containing FKBP-52 and p23), thereby preventing nuclear translocation and activation of steroid response elements. Geldanamycin (0.1–10 nM) alone significantly [Mann-Whitney U test ($\alpha=0.05$)] increased neurite outgrowth in a concentration-dependent fashion. Thus, disruption of the steroid receptor complex is sufficient to increase neurite outgrowth. Since geldanamycin and steroid hormones have opposite effects on the translocation of the steroid receptor ligand component to the nucleus, these results demonstrate that the promotional effect of these compounds on neurite outgrowth is mediated by a mechanism other than nuclear translocation of the steroid receptor ligand-binding component and activation of steroid response elements. Using this information, it is now possible to exploit the structure of geldanamycin to develop a new class of hsp-90-binding compounds for use in nerve regeneration.

Assays for determining disruption of the steroid receptor complex are set forth in Example 10.

EXAMPLE 7

Neurotrophic Effect of Geldanamycin Combined with Other Compounds

To explore the interaction of other neurotrophic substances with geldanamycin, SH-SY5Y cells were co-treated with 1 nM (not shown) or 10 nM geldanamycin and various other compounds. On the one hand, geldanamycin (10 nM) significantly [Mann-Whimey U test ($\alpha=0.05$)] inhibited neurite outgrowth promotion by FK506 , dexamethasone or β-estradiol; at 0.1 nM, geldanamycin was less effective in inhibiting the neurite outgrowth-promoting effect of all these compounds. On the other hand, geldanamycin (10 nM) significantly [Mann-Whitney U test ($\alpha=0.05$)] enhanced the neurite outgrowth-promoting effect of the FKBP-52 antibody. The combined effect of FKBP-52 antibody and geldanamycin is consistent with their different binding sites on hsp-90; geldanamycin binds to the N-terminus and FKBP-52 to the C-terminus portions of hsp-90 (Scheigel et al., *J. Bio. Chem.* 272:8007, 1997). This finding shows an interaction at the steroid level complex for all tested compounds, yet reveals that the antibody acts somewhat differently.

Figure 2:
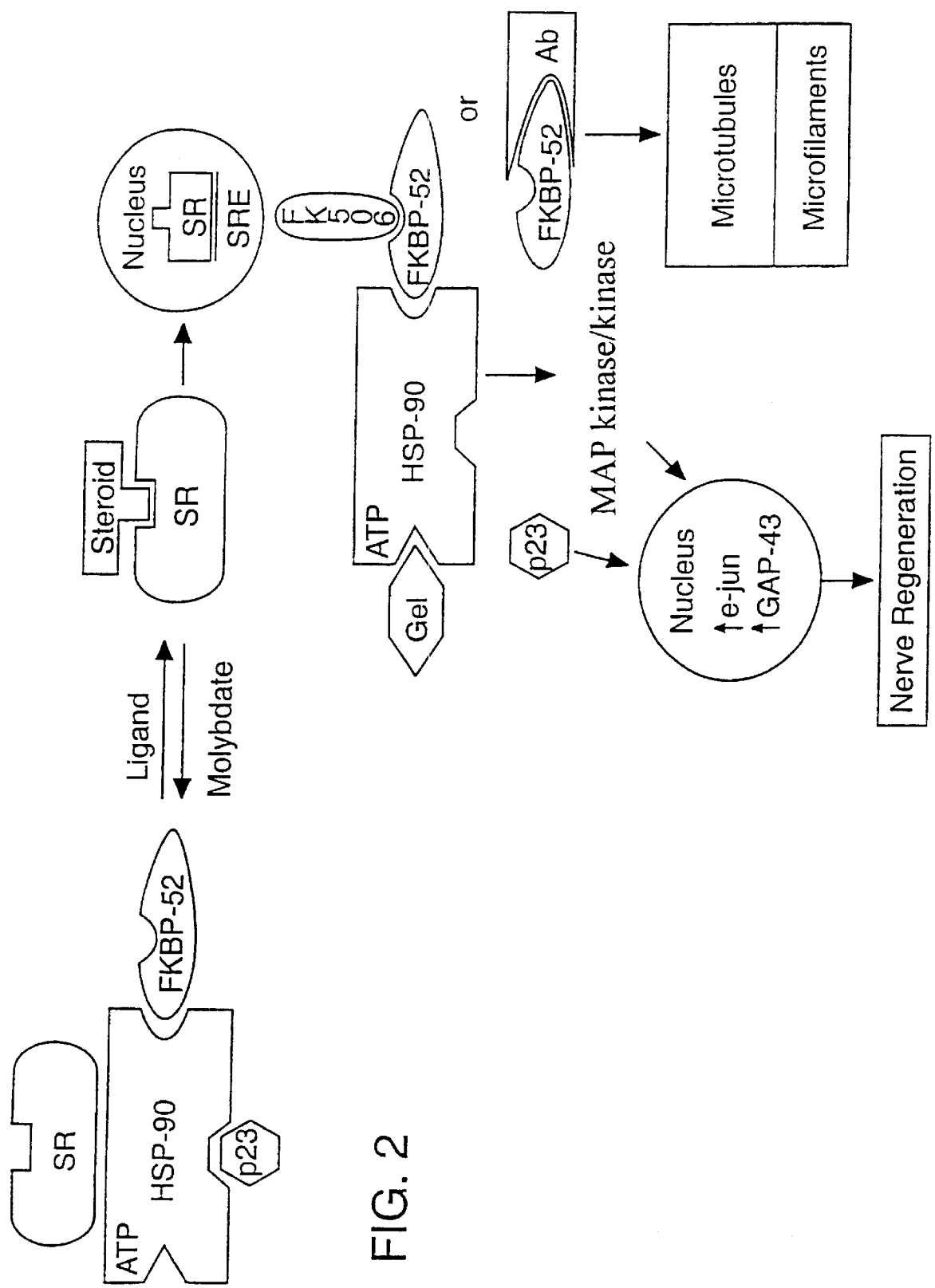
FIG. 2 is a schematic diagram illustrating the mature steroid receptor complex, and the binding sites of some of the agents of the present invention that promote nerve growth.

These findings can be explained by the model shown in FIG. 2 in which geldanamycin produces a conformational change (not dissociation) in hsp-90 which, via its adenosine triphosphatase activity, leads to an activation (adenosine diphosphate) state in which p23 dissociates from the complex. In contrast, this conformational change may be blocked, thereby preventing release of p23, when FKBP-52 is bound to FK506, because FK506 does not dissociate FKBP-52 from the complex; a similar interaction may occur in the presence of steroid hormones to prevent the conformational change in hsp-90. This model indicates that the FKBP-52 antibody dissociates FKBP-52 from the complex, perhaps by altering its degree of phosphorylation and thereby reducing its binding to hsp-90, and leads to a conformational change in hsp-90 that results in release of p23. Thus, the combination of geldanamycin and the FKBP-52 antibody are additive (not inhibitory) because dissociation of FKBP-52 from hsp-90 would not prevent the geldanamycin-induced conformational change that releases p23.

In addition, the association of FKBP-52 with microtubules (Czar et al., *Mol. Endocrinol* 8:1731, 1994) and perhaps microfilaments such as actin (Tai et al., *Biochem.* 32:8842, 1993) following its dissociation from hsp-90, would promote the greater neurite outgrowth seen with FKBP-52 antibody than with FK506. The microtubules are involved with neurite outgrowth and axonal elongation, hence association of FKBP-52 with those elements (after dissociation from the SRC) is a particularly effective mechanism of promoting neurite growth.

EXAMPLE 8

Stabilization of Steroid Receptor Complex Inhibits Neurite Outgrowth

This Example shows that prevention of the dissociation of the steroid receptor complex inhibits neurite outgrowth, as predicted by the model shown in FIG. 2. SH-SY5Y cells were treated with sodium molybdate, a transition metal oxyanion, that at a concentration of 20 mM prevents dissociation of the complex in intact cells. Surprisingly, molybdate (20 mM) itself exhibited a modest but significant [Maim-Whitney U test ($\alpha$=0.05)] agonist effect on neurite outgrowth. As predicted, molybdate (20 mM) reduced the neurite outgrowth promotion elicited by FK506, the distribution of neurite lengths produced by FK506 in the presence of molybdate being not significantly [Mann-Whitney U test ($\alpha$=0.05)] different from that with molybdate alone. Furthermore, molybdate (20 mM) significantly [Mann-Whitney U test ($\alpha$=0.05)] inhibited the neurite outgrowth-promoting effects of FKBP-52 antibody.

The neurite outgrowth-promoting effect of molybdate (20 mM) in the presence of dexamethasone was significantly [Mann-Whitney U test ($\alpha$=0.05)] reduced compared to molybdate alone. Furthermore, molybdate (20 mM) completely [Mann-Whitney U test ($\alpha$=0.05)] inhibited the neurite outgrowth-promoting effect of $\beta$-estradiol and geldanamycin; the larger degree of interaction between molybdate and $\beta$-estradiol compared to molybdate and dexamethasone is consistent with a greater involvement of the estrogen receptor complex in human SH-SY5Y neurite outgrowth. Molybdate produced similar but less marked effects at a lower (2 mM) concentration (not shown).

While it is unclear how molybdate alone increases outgrowth, the data (showing that molybdate inhibits the activity of all agents, including FKBP-52 antibody) indicate that dissociation of the receptor complex is an essential step for activation of the neurite development pathway. Prevention of this dissociation by molybdate inhibits the neurotrophic activity of geldanamycin and other neurotrophic agents that act by disrupting association of the complex. Hence inhibition of neurotrophic activity by adding molybdate to an assay can constitute a test for determining whether a neurotrophic agent is structurally or functionally disrupting the SRC.

EXAMPLE 9

Determination of Rotamase Inhibition Activity

Some embodiments of the present invention have low or absent inhibition of peptidyl-prolyl isomerase (rotamase) activity. Inhibition of this activity can be evaluated by techniques known in the art, such as that described in U.S. Pat. No. 5,614,547. Inhibition is expressed as an apparent Ki for cis-trans isomerization of an alanine-proline bond in a model substrate, N-succinyl-Ala-Ala-Pro-Phe-p-nitroanilide, which is monitored spectrophometrically in a chymotrypsin-coupled assay, which releases para-nitroanilide from the trans form of the substrate. The inhibition of this reaction caused by the addition of different concentrations of inhibitor is determined, and the data is analyzed as a change in the first-order rate constant as a function of inhibitor concentration to yield the apparent Ki values.

In a plastic cuvette are added 950 ml of ice cold assay buffer (25 mM HEPES, pH 7.8, 100 nM NaCl), 10 ml of FKBP (2.5 mM in 10 mM Tris-Cl pH j7.5, 100 mM NaCl, 1 mM dithiothreitol), 25 ml of chymotrypsin (50 mg/ml in 1 mM HCl) and 10 ml of test compound at various concentrations in dimethyl sulfoxide. The reaction is initiated by the addition of 5 ml of substrate (succinyl-Ala-Phe-Pro-Phe-para-nitroanilide, 5 mg/ml in 2.35 mM LiCl in trifluroethanol).

Absorbance at 390 nm versus time is monitored for 90 seconds using a spectrophotometer and the rate constants are determined from the absorbance versus time data files. Inhibitors that have an apparent Ki of 2500 or greater, for example greater than 5000 or even 10,000, are considered to have "low" rotamase inhibition.

EXAMPLE 10

Assays for Determining if Agent Binds to and Disrupts SRC Function

Assays for detecting binding to components of the SRC are given in Example 1. Detection of disruption of the SRC can be assessed by additional assays.

Disruption of the SRC by release of p23 can be assessed by the techniques disclosed in Whitesell and Cook, 1996, where benzoquinone ansamycin binding to hsp-90 was shown to result in complete loss of p23 protein from glucocorticoid receptor immunoprecipitates, which was associated with a rapid, noncompetitive loss of dexamethasone binding activity, and a slower (2–8 hours) marked decline in the cellular level of glucocorticoid receptor protein. Using this approach, drug treatment did not disrupt coprecipitation of hsp-90 with glucocorticoid receptor, and a complete loss of detectable p23 from glucocorticoid receptor precipitates.

Whitesell and Cook performed affinity precipitation by lysing cells in TNESV buffer (50 mM Tris-HCl, pH 7.4%/

1% Nonidet P-40/2 mM EDTA/100 mM NaCl/1 mM orthovanadate/1 mM phenylmethysulfonyl fluoride/20 µg/ml leupeptin/20 µg/ml aprotinin) and lysates (0.75 mg of total protein per precipitation) incubated with geldanamycin-coupled beads. Bound proteins are eluted by heating in reduced loading buffer and analyzed by SDS-PAGE followed by Coomassie blue staining. Immnoprecipitation from cell lysates is performed using a specific monoclonal antibody BuGR-2, and protein G Sepharose beads (Pharmacia). For experiments involving coprecipitation of GR with heteroprotein complex components, cells are lysed in detergent-free hypotonic buffer with 10 mM sodium molbydate. Immunoblot detection of proteins in total cells lysates, geldanamycin affinity precipitates, and glucocorticoid receptor immunoprecipitates are performed after SDS-PAGE and electrophoretic transfer of proteins to nitrocellulose. BuGR-2 hybridoma supernatant (1:40) is used for detection of rodent derived GR while a peptide-derived rabbit polyclonal antibody (1:250; PA1-512, Affinity Bioreagents; Golden, Colo.) is used for the human GR. Hsp-90 and hsp-70 are detected with antibodies AC88 and N27F3-4 respectively (1:5000; StressGen; Victoria, BC, Canada). Ascites containing antibody JJ3 (1:1000) is used to blot for p23. Polyclonal rabbit anti-ubiquitin antiserum (1:500; Sigma Chemical Co.) is used to detect ubiquitinated proteins after blots are autoclaved for 20 minutes to fully denature ubiquitinated proteins and enhance their detection. Detection is achieved using appropriate peroxidase-conjugated secondary antibodies (1:20,000) and chemiluminescent substrate (Kierkegaard and Perry Laboratories, Gaithersburg, Md.).

Loss of dexamethasone binding activity can be determined with a binding assay in which HeLa cells ($2 \times 10^5$/well, 24-well plate) are treated with various concentrations of geldanamycin for varying periods of time in complete medium at 37 degrees C. At the end of the treatment interval, medium is aspirated and monolayers washed twice with ice-cold PBS containing 1% BSA and 0.1% sodium azide (binding buffer). Monolayers are then incubated for 60 minutes on ice with 1.0 µCi/well (48 nM) [$^3$H] dexamethasone (Amersham, 82 Ci/mmol) in binding buffer with or without 5 mM non-radioactive dexamethasone. After this binding interval, wells are washed four times with cold binding buffer and then extracted with 0.5 ml ethanol for 30 minutes. The ethanol solution is transferred to scintillation vials and evaporated to dryness before standard liquid scintillation counting. Specific binding is calculated as the counts per minute bound in the absence of excess nonradioactive dexamethasone less the counts per minute bound in its presence. Similar measurements can be made with estrogen and other steroid receptors, to detect disruption in ligand binding, by substituting those steroids for dexamethasone.

A loss of detectable p23 (disappearance of the p23 band) from receptor immunoprecipitates can indicate loss of p23 in association with disruption of the SRC.

EXAMPLE 11

Preparation of Antibodies

The present invention also contemplates the preparation of antibodies against components of the SRC. The components of the SRC can be purified by techniques known in the art, such as immnoprecipitation. Monoclonal or polyclonal antibodies may be produced to either the SRC component proteins, peptide fragments, or mutant forms of these proteins. Optimally, antibodies raised against the protein will specifically detect the protein. That is, antibodies raised against the protein would recognize and bind the protein and would not substantially recognize or bind to other proteins found in human cells. The determination that an antibody specifically detects a protein is made by any one of a number of standard immunoassay methods; for instance, the Western blotting technique (Sambrook et al., 1989).

To determine that a given antibody preparation specifically detects the protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase.

Antibodies which specifically detect the protein will, by this technique, be shown to bind to the protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific protein binding.

Antibodies that specifically bind to a protein component of the SRC belong to a class of molecules that are referred to herein as "specific binding agents." Specific binding agents that are capable of specifically binding to the SRC protein may include polyclonal antibodies, monoclonal antibodies (including humanized monoclonal antibodies) and fragments of monoclonal antibodies such as Fab, F(ab')2 and Fv fragments, as well as any other agent capable of specifically binding to a protein component of the SRC.

Monoclonal antibody to epitopes of the SRC protein components identified and isolated as described can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988). In addition, protocols for producing humanized forms of monoclonal antibodies (for therapeutic applications) and fragments of monoclonal antibodies are known in the art.

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971).

Booster injections can be given at regular intervals, and antiserum harvested when antibody titer thereof, as determined semi-qanitatively, for example, by double immunodiffusion in agar against known concentrations of the antigen, begins to fall. See, for example, Ouchterlony et al. (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher (1980).

A third approach to raising antibodies against the SRC proteins is to use synthetic peptides synthesized on a commercially available peptide synthesizer based upon the predicted amino acid sequence of the protein components of the SRC.

EXAMPLE 12

Geldanamycin Analogs and Derivatives

The term "geldanamycm derivative" refers to compounds that are structurally analogous to geldanamycin in their ability to stimulate neurite outgrowth. Geldanamycin consists of a closed ansa ring with a planar benzoquinone embedded in it.

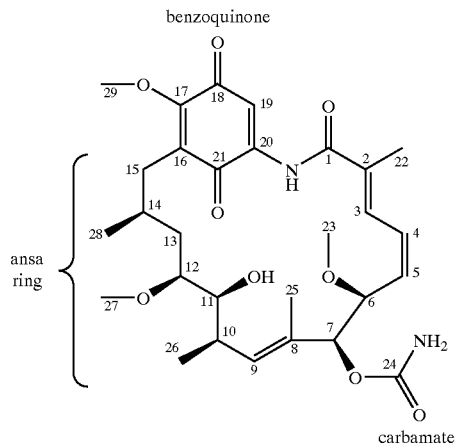

The ansa ring is sterically hindered because its backbone includes a planar amide and three carbon-carbon double bonds (two of them arranged in a 1,3-diene), and nine of its sixteen backbone atoms carry nonhydrogen substitutents such as a carbonyl, a carbamate (—OC(O)NH$_2$), a hydroxyl, two methoxy and four methyl groups. The crystal structure of geldanamycin has been set forth, and the structure/activity relationships of the benzoquinone ansamycins have been described in Stebbins et al., Cell 89:239–250, 1997; Schnur et al., J. Med. Chem. 38:3813–3820, 1995; and Schnur et al., J. Med. Chem. 38:3806–3812, 1995. Geldanamycin derivatives may have the carbamate group and ansa ring of geldanamycin (Schur et al., J. Med. Chem. 38:3806–3812, 1995), and/or have modifications at functional groups such as the C23 methoxy and C22 methyl groups (Stebbins et al., Cell 89:239–250, 1997). Geldanamycin derivatives are also discussed in U.S. Pat. Nos. 5,3877,584, 4,261,989, and 3,987,035, and in Japanese Patent Applications 88041885, 56100766, and 89002593, for example.

The structures of some of the benzoquinone ansamycins that are structural analogs of geldanamycin are set forth in Table 2.

TABLE 2

Some Structural Analogs of Geldanamycin

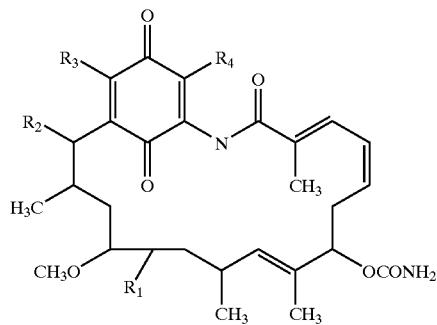

| | R$_1$ | R$_2$ | R$_3$ | R$_4$ |
|---|---|---|---|---|
| GA | —OH | —H | —OCH$_3$ | —H |
| HA | —OCH$_3$ | —OCH$_3$ | —H | —H |
| HD | —OH | —H | —NHC$_6$H$_{12}$NH$_2$ | —H |
| GM | —OH | —H | —OCH$_3$ | —CHN—N N—CH$_3$ |

Additional benzoquinone ansamycin analogs of geldanamycin are shown in Tables 3 and 4. Table 3 illustrates several synthesis schemes for gledanamycin derivatives, while Table 4 sets forth substitutions for the derivatives, as described more fully in Schnur, et al., J. Med. Chem. 38:3813–3820, 1995.

TABLE 3
Synthesis Scheme for Geldanamycin Derivatives With Ansa-Ring Modifications
Scheme 1
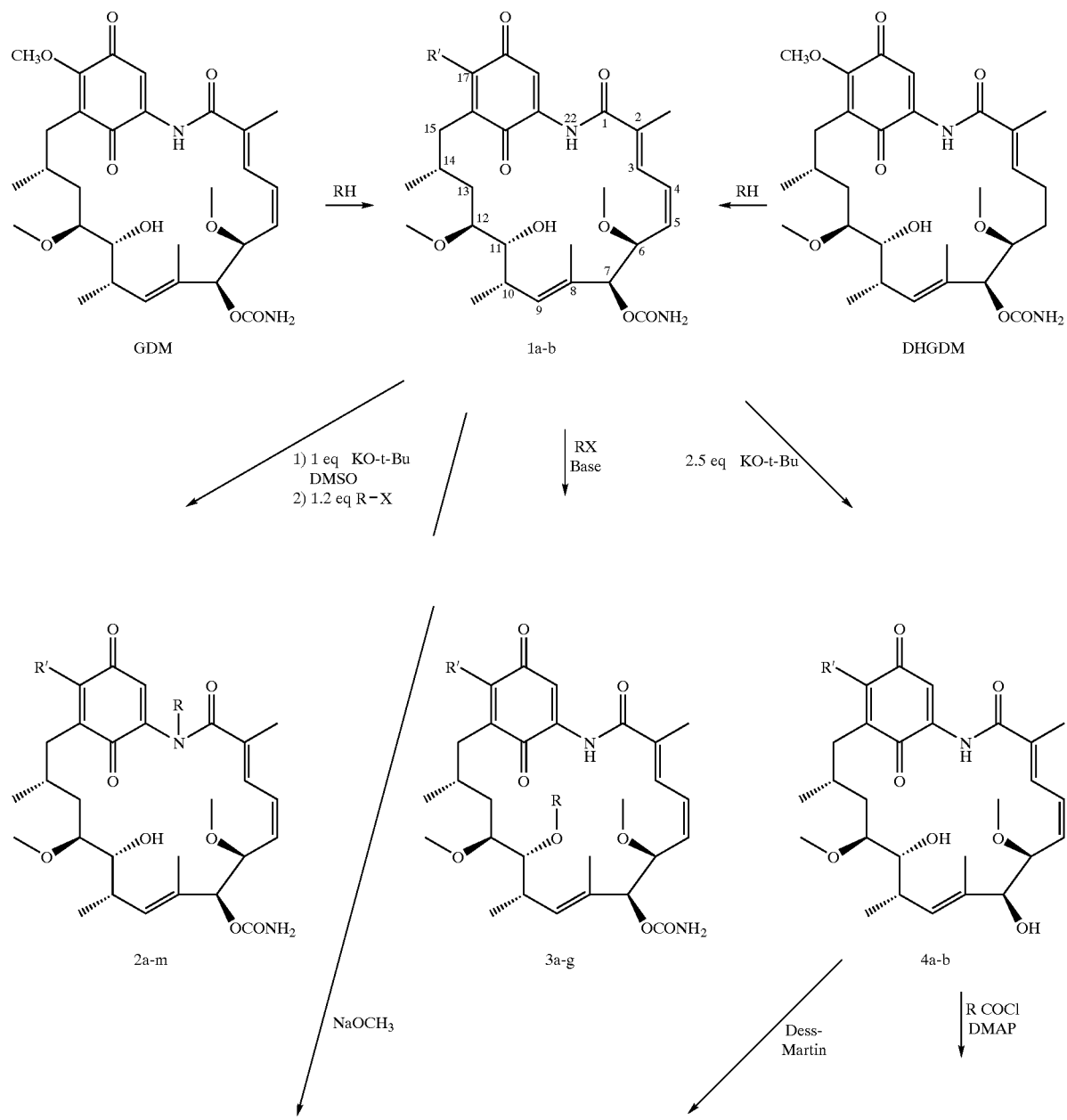

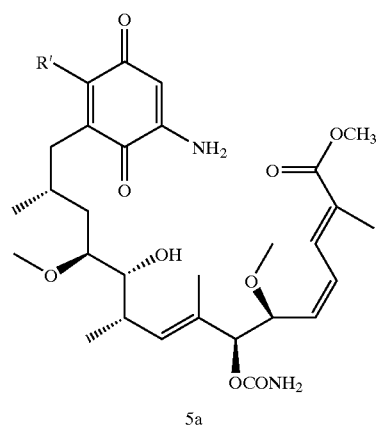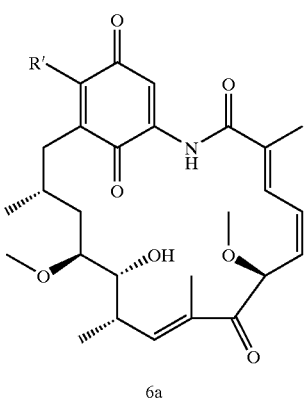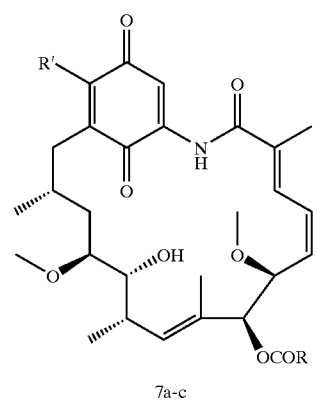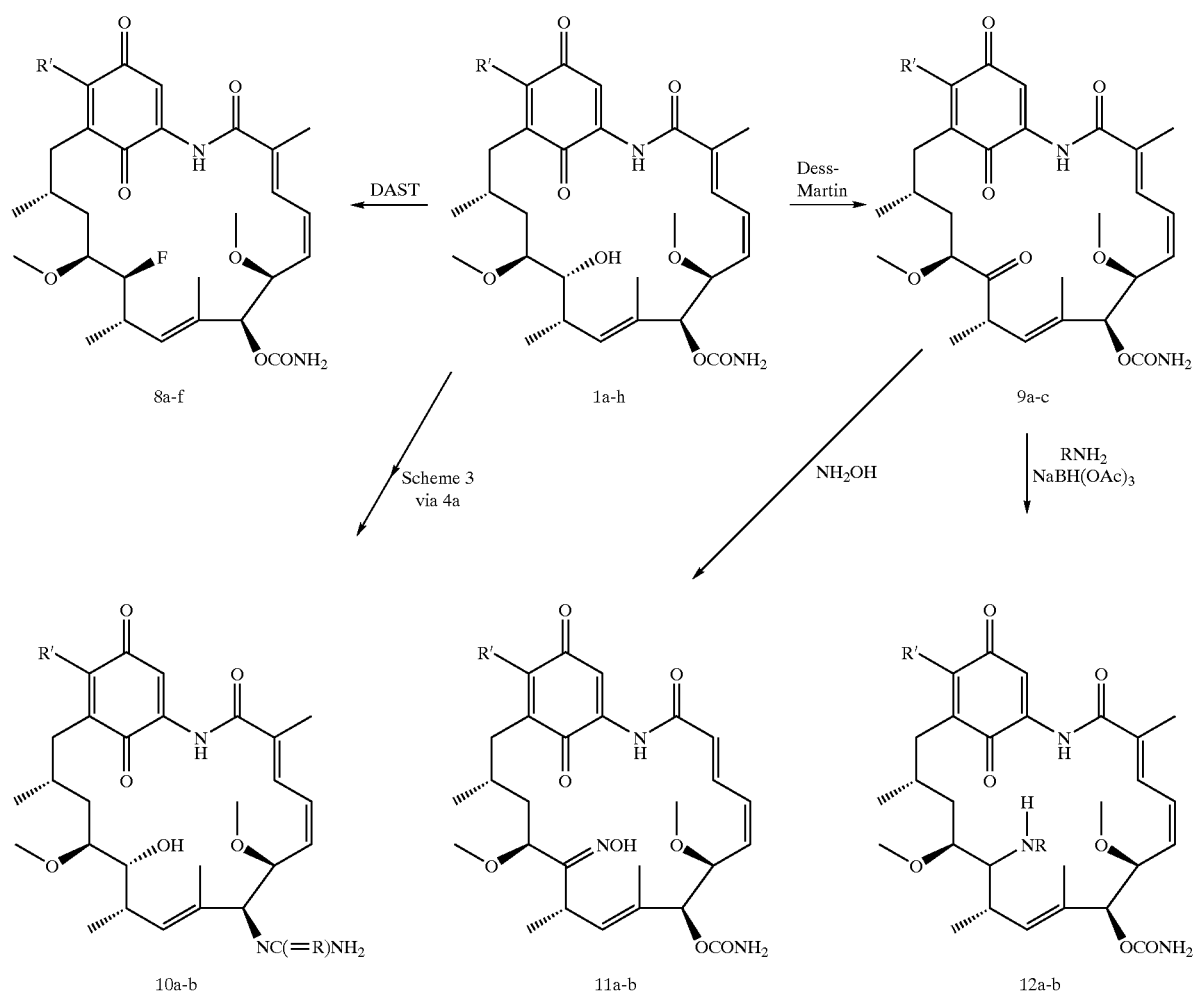

TABLE 4

Substitutions for Compounds Shown in Table 3

| compd[a] | R | R' |
|---|---|---|
| HBM A | | |
| GDM | | $OCH_3$ |
| DHGDM | | $OCH_3$ |
| 1a | | $-N(CH_2)_3-$ |
| 1b | | $NH_2$ |
| 1c | | $NHCH_2CH=CH_2$ |
| 1d | | $NHCH(CH_3)_2$ |
| 1e | | $NHCH_2$ |
| 1f* | | $-N(CH_2)_3-$ |
| 1g* | | $NH_2$ |
| 1h* | | $NHCH_2CH=CH_2$ |
| 2a | phenacyl | $NH_2$ |
| 2b | 3',4'-dichlorophenacyl | $NH_2$ |
| 2c | 3'-iodo-4'-azidophenacyl | $NH_2$ |
| 2d | 2'-methoxyphenacyl | $NH_2$ |
| 2e* | 2'-methoxyphenacyl | $NH_2$ |
| 2f | 4'-methoxyphenacyl | $NH_2$ |
| 2g | 4'-nitrophenacyl | $NH_2$ |
| 2h | 1'-napthacyl | $NH_2$ |
| 2i | 2'-napthacyl | $NH_2$ |
| 2j | 4'-azidophenacyl | $NH_2$ |
| 2k | 4'-azidophenacyl | $-N(CH_2)_3-$ |
| 2l | 2'-oxopropyl | $NH_2$ |
| 2m | 2'-pyridylmethyl | $NH_2$ |
| 3a | $COCH_8$ | $-N(CH_2)_3-$ |
| 3b | $CONHSO_2NHCH(CH_3)_2$ | $-N(CH_2)_3-$ |
| 3c | $CONHSO_2N[(CH_2)_2]_2NCH_3$ | $-N(CH_2)_3-$ |
| 3d | $CONH_2$ | $-N(CH_2)_3-$ |
| 3e | $CONHSO_2N(CH_2)_3$ | $NHCH_2CH=CH_2$ |
| 3f | $CONHSO_2NHCH(CH_3)_2$ | $NHCH_2CH=CH_2$ |
| 3g | $CONHSO_2N(CH_2)_2NCH_3$ | $NHCH_2CH=CH_2$ |
| 4a | | $-N(CH_2)_3-$ |
| 4b | | $NH_2$ |
| 5a | | $-N(CH_2)_3-$ |
| 6a | | $NHCH(CH_2)_3$ |
| 7a | $COCO_2H$ | $-N(CH_2)_3-$ |
| 7b | $CONHCH_2CH_3$ | $NHCH_2CH=CH_2$ |
| 7c | $COCH_2NH_2$ | $NHCH_2CH=CH_2$ |
| 8a | | $-N(CH_2)_3-$ |
| 8b* | | $-N(CH_2)_3-$ |
| 8c | | $NHCH_2CH=CH_2$ |
| 8d* | | $NHCH_2CH=CH_2$ |
| 8e | | $NH_2$ |
| 8f | | $NHCH(CH_2)_2$ |
| 9a | | $NHCH_2CH=CH_2$ |
| 9b | | $-N(CH_2)_3-$ |
| 9c | | $NHCH_3$ |
| 10a | S | $-N(CH_2)_3-$ |
| 10b | O | $-N(CH_2)_3-$ |
| 11a | | $-N(CH_2)_3-$ |
| 11b | | $NHCH(CH_3)_2$ |
| 12a | $CH_2CH=CH_2$ | $NHCH_3$ |
| 12b | $CH_2C_6H_5$ | $NHCH_3$ |

TABLE 5
Several Synthesis Schemes for Aminogeldanamycin Derivatives (Scheme 1), and Geldanamycin with Quinone Modifications (Scheme 2)

Scheme 1

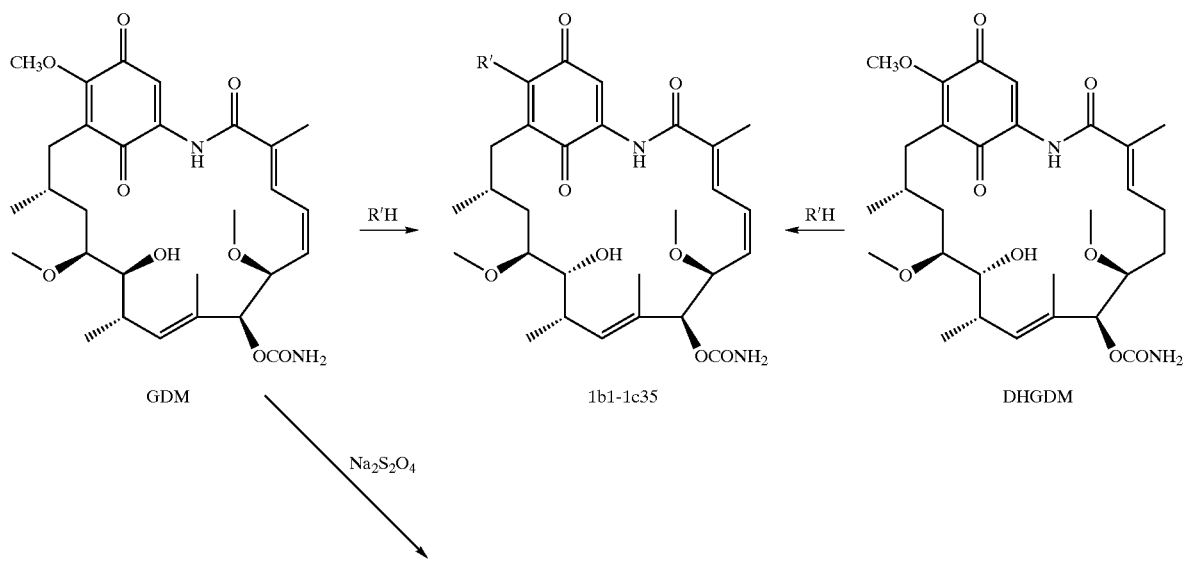

-continued
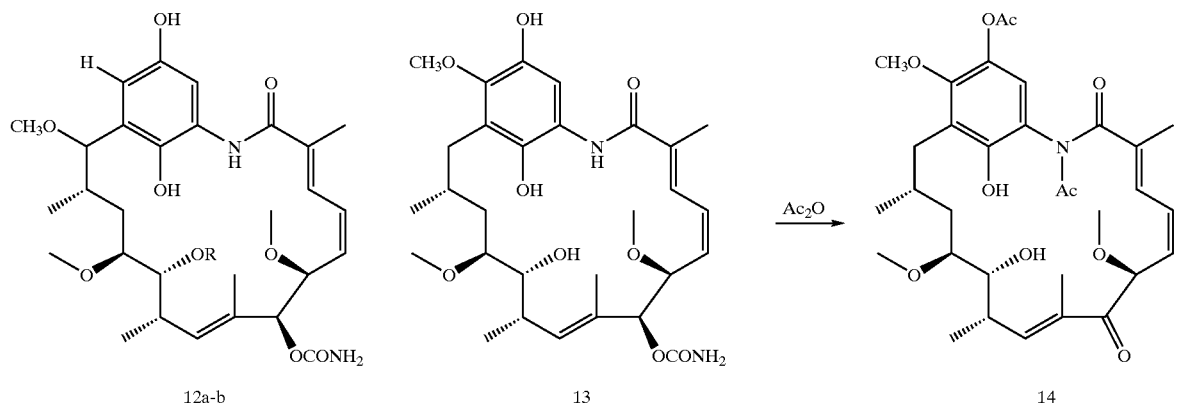
12a-b    13    14
Scheme 2. Geldanamycin Quinone Modification
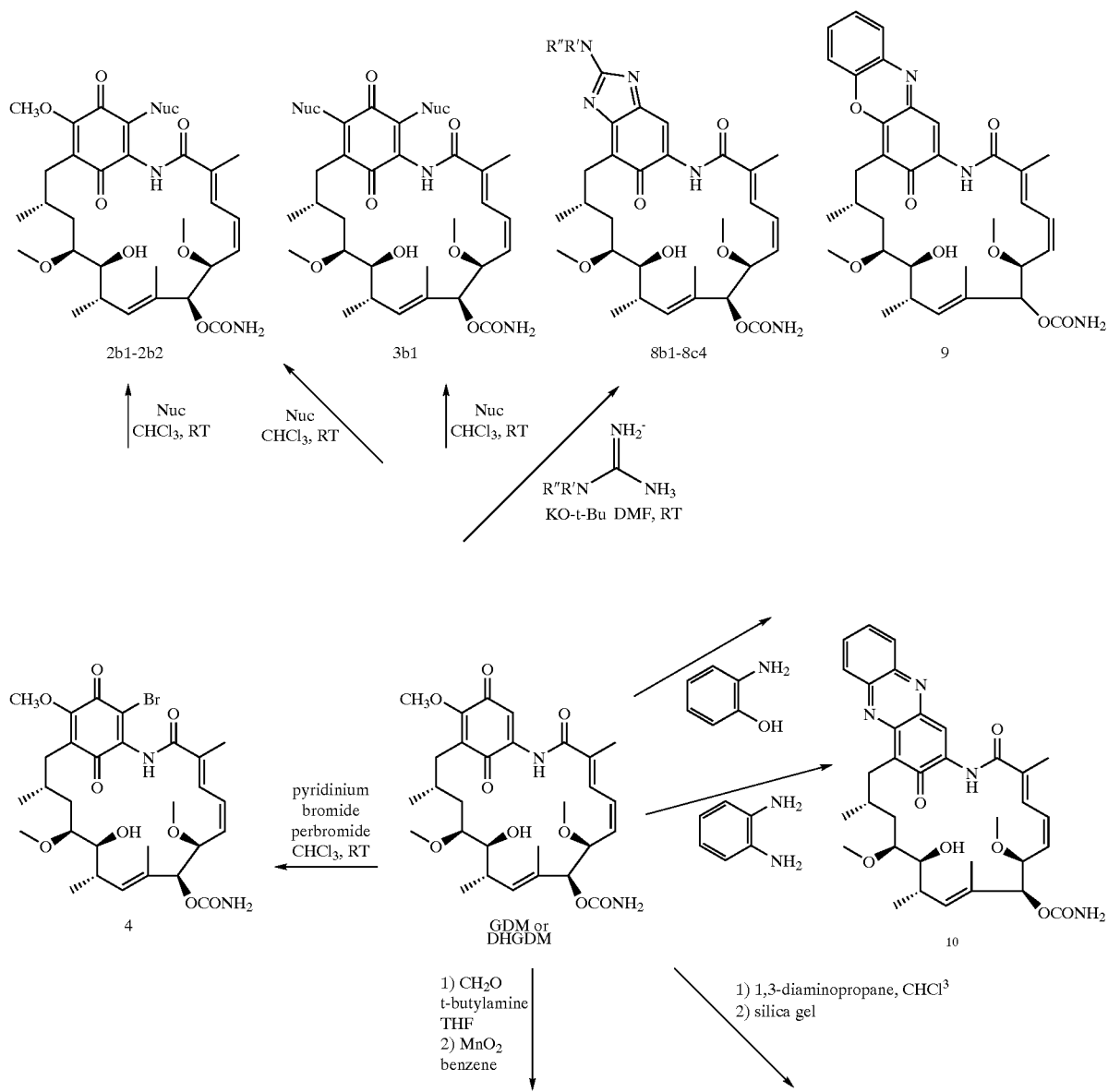

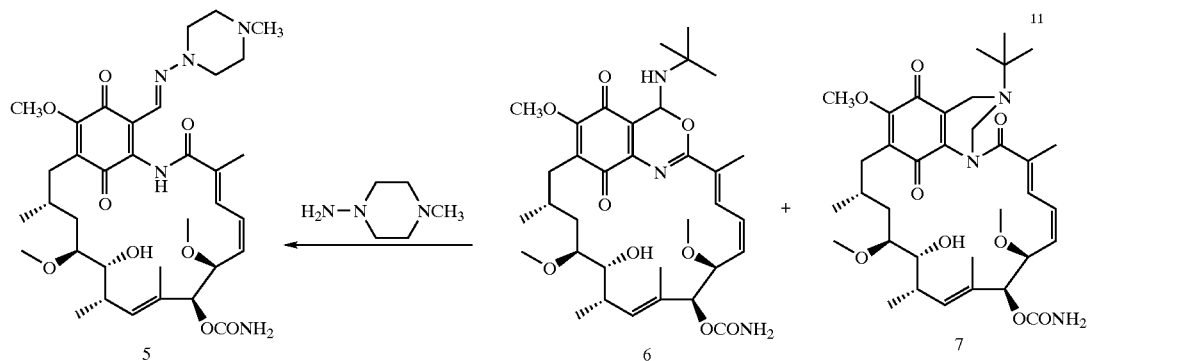

Some substitution patterns for the derivitives in Table 5 are shown in Table 6.

TABLE 6

Some Substitutions for Compounds Shown in Table 5

| compd[a] | R | R' |
|---|---|---|
| HBM A | | |
| GDM | | OCH$_3$ |
| DHGDM | | OCH$_3$ |
| 1a | | —N(CH$_2$)$_3$— |
| 1b | | NH$_2$ |
| 1c | | NHCH$_2$CH=CH$_2$ |
| 1d | | NHCH(CH$_3$)$_2$ |
| 1e | | NHCH$_2$ |
| 1f* | | —N(CH$_2$)$_3$— |
| 1g* | | NH$_2$ |
| 1h* | | NHCH$_2$CH=CH$_2$ |
| 2a | phenacyl | NH$_2$ |
| 2b | 3',4'-dichlorophenacyl | NH$_2$ |
| 2c | 3'-iodo-4'-azidophenacyl | NH$_2$ |
| 2d | 2'-methoxyphenacyl | NH$_2$ |
| 2e* | 2'-methoxyphenacyl | NH$_2$ |
| 2f | 4'-methoxyphenacyl | NH$_2$ |
| 2g | 4'-nitrophenacyl | NH$_2$ |
| 2h | 1'-napthacyl | NH$_2$ |
| 2i | 2'-napthacyl | NH$_2$ |
| 2j | 4'-azidophenacyl | NH$_2$ |
| 2k | 4'-azidophenacyl | —N(CH$_2$)$_3$— |
| 2l | 2'-oxopropyl | NH$_2$ |
| 2m | 2'-pyridylmethyl | NH$_2$ |
| 3a | COCH$_8$ | —N(CH$_2$)$_3$— |
| 3b | CONHSO$_2$NHCH(CH$_3$)$_2$ | —N(CH$_2$)$_3$— |
| 3c | CONHSO$_2$N[(CH$_2$)$_2$]$_2$NCH$_3$ | —N(CH$_2$)$_3$— |
| 3d | CONH$_2$ | —N(CH$_2$)$_3$— |
| 3e | CONHSO$_2$N(CH$_2$)$_3$ | NHCH$_2$CH=CH$_2$ |
| 3f | CONHSO$_2$NHCH(CH$_3$)$_2$ | NHCH$_2$CH=CH$_2$ |
| 3g | CONHSO$_2$N(CH$_2$)$_2$NCH$_3$ | NHCH$_2$CH=CH$_2$ |
| 4a | | —N(CH$_2$)$_3$— |
| 4b | | NH$_2$ |
| 5a | | —N(CH$_2$)$_3$— |
| 6a | | NHCH(CH$_2$)$_3$ |
| 7a | COCO$_2$H | —N(CH$_2$)$_3$— |
| 7b | CONHCH$_2$CH$_3$ | NHCH$_2$CH=CH$_2$ |

TABLE 6-continued

Some Substitutions for Compounds Shown in Table 5

| compd[a] | R | R' |
|---|---|---|
| 7c | COCH$_2$NH$_2$ | NHCH$_2$CH=CH$_2$ |
| 8a | | —N(CH$_2$)$_3$— |
| 8b* | | —N(CH$_2$)$_3$— |
| 8c | | NHCH$_2$CH=CH$_2$ |
| 8d* | | NHCH$_2$CH=CH$_2$ |
| 8e | | NH$_2$ |
| 8f | | NHCH(CH$_2$)$_2$ |
| 9a | | NHCH$_2$CH=CH$_2$ |
| 9b | | —N(CH$_2$)$_3$— |
| 9c | | NHCH$_3$ |
| 10a | S | —N(CH$_2$)$_3$— |
| 10b | O | —N(CH$_2$)$_3$— |
| 11a | | —N(CH$_2$)$_3$— |
| 11b | | NHCH(CH$_3$)$_2$ |
| 12a | CH$_2$CH=CH$_2$ | NHCH$_3$ |
| 12b | CH$_2$C$_6$H$_5$ | NHCH$_3$ |

Analogs can also be modified by appending appropriate functionalities by well-known methods to enhance selected biological properties, including increasing penetration of the analogs into a given cellular compartment (e.g., blood, lymphatic system, central nervous system, etc.), increase oral availability, increase solubility to permit administration by injection, alter metabolism, and alter rate of excretion.

In some particular embodiments, analogs have a molecular weight below about 750 atomic mass units (a.m.u.) (as the parent compound, although the salts of such compounds can have higher molecular weights).

EXAMPLE 13

FK506 and Rapamycin Analogs

The term "FK506 analogs" refers to compounds that are structurally analogous to FK506 in their ability to stimulate neuritic outgrowth. Some FK506 analogs, such as V-10,367, retain the FKBP12 binding domain but lack the structural components of the effector domain that interacts with calcineurin. The FK506 analogs may bind FKBP12 with low or high affinity. V-10,367, for example, binds FKBP12 with high affinity ($K_d$<1 nM) (Armistead et al., *Acta Crystallogr.* 51:522–528, 1995).

There has been an intense effort to design compounds that are structurally related to FK506 and that share the ability of FK506 to inhibit FKBP12 and thereby cause immunosuppression. See, for example: Bierer et al., *Science* 250:556–559, 1990; Van Duyne et al., *Science* 252:839–842, 1991; Van Duyne et al., *J. Mol. Biol.* 229:105–124, 1993; Hauske et al., *J. Med. Chem.* 35:4284–4296, 1992; Holt et al., *J. Am. Chem. Soc.* 115:9925–9938, 1993; Holt et al., *Bioorg. Med. Chem. Lett.* 3:1977–1980, 1993; Teague and Stocks, *Bioorg. Med. Chem. Lett.* 3:1947–1950, 1993; Wang et al., *Bioorg. Med. Chem. Lett.* 4:1161–1166, 1994; Yamashita et al., *Bioorg. Med. Chem. Lett.* 4:325–328, 1994; Stocks et al., *Bioorg. Med. Chem. Lett.* 4:1457–1460, 1994; Goulet et al., *Perspect. Drug Disc. Design* 2:145–162, 1994; Wilson et al., *Acta Cryst.* D51:511–521, 1995; Armistead et al., *Acta Cryst.* D51:522–528, 1995; U.S. Pat. Nos. 5,192,773, 5,330,993, 5,516,797, 5,612,350, 5,614,547, 5,622,970, 5,654,332; and published international patent applications WO 92/00278, WO 92/04370, WO 92/19593, WO 92/21313, WO 94/07858, and WO 96/40633. These references set forth the structure of FK506 and some of its known analogs, such as V-10,367, which lacks the effector domain (shown in brackets) that inhibits calcineurin. A "known" or "recognized" compound is a compound (such as an FK506 analog) that has previously been reported in patents or publications that qualify as prior art.

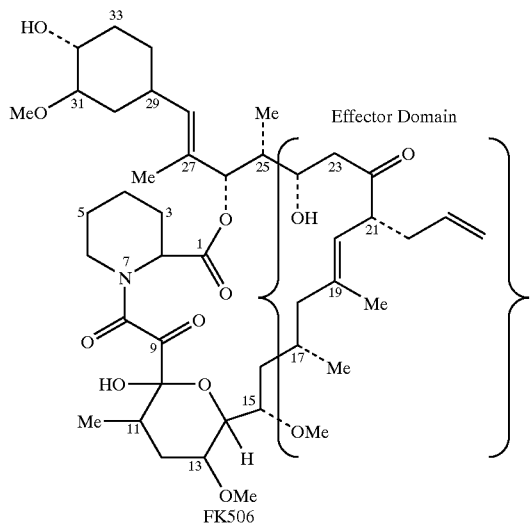

FK506

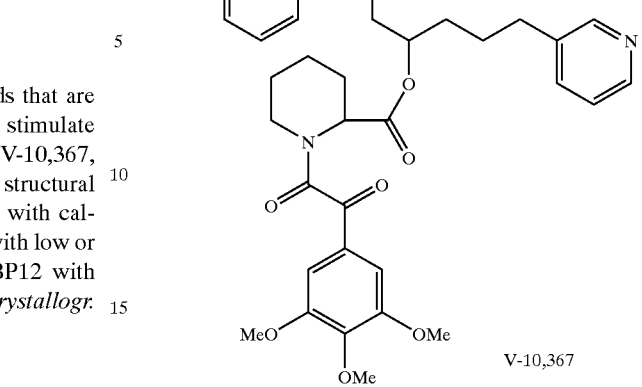

V-10,367

FK506 analogs have a wide range of binding affinities for FKBP-12. The mechanism for neurotrophic activity of FK506 presented herein indicates that the effectiveness of FK506 and FK506 analogs in stimulating nerve cell growth is unrelated to their ability to bind FKBP-12. Instead, their effectiveness in stimulating nerve cell growth relates to ability of such compounds to physically or functionally disrupt the steroid receptor complex, for example by interfering with the interaction of FKBP-52 and hsp-90 in a steroid receptor complex, or by promoting dissociation of p23 from the complex.

A "non-binding FK506 analog" is defined as an FK506 analog that does not substantially bind to FKBP-12. An FK506 analog with low affinity for binding FKBP-12 refers to an analog that binds FKBP12 with an apparent $K_d$ of greater than 10 μM as measured using well-known assays, and preferably greater than 30 μM, and more preferably greater than 100 μM. Values for the apparent $K_d$ can be determined, for example, by a competitive LH-20 binding assay performed as described, for example, in Harding et al., *Nature* 341:758–760, 1989 (using 32-[1-$^{14}$C]-benzoyl FK506 as a reporting ligand; Siekierka et al., *Nature* 341:755–757, 1989, using [$^3$H]dihydro-FK506 as a reporting ligand); and U.S. Pat. No. 5,654,332.

Alternatively or additionally, the analog may be one that does not significantly inhibit FKBP-12 rotamase activity when administered to a patient at dosage levels of about 0.01 to about 100 mg/kg body weight/day. Assays for inhibition of FKBP12 rotamase activity are described in Example 9.

Non-binding FK506 analogs are non-immunosuppressive, as can be demonstrated by well-known assays, e.g., as discussed in U.S. Pat. No. 5,516,797, WO 92/21313, WO 92/19593, and WO 92/04370.

"Rapamycin analogs" include compounds structurally similar to rapamycin, for example WAY-124,466 shown in Ocain et al., *Biochem. Biophys. Res. Commun.* 192-1340–1346, 1993. This analog is identical to rapamycin, except that it has been modified in the triene region, and has a Ki for PPIase activity of 12.5 nM, as determined by the methods shown in that reference. It is also non-immunosuppressive, as determined in that reference by an inability to inhibit the proliferation of murine thymocytes. Other rapamycin analogs include other macrocyclic trienes, mono- and diacylated derivatives esterified at the 31 and 42 positions (U.S. Pat. No. 4,313,885) and water soluble prodrugs of rapamycin (U.S. Pat. No. 4,650,803); hydrogenated derivatives in which one, two, or three of the double bonds at the 1-, 3-, or 5-positions have been reduced to the corresponding alkane, or a pharmaceutically acceptable salt thereof (U.S. Pat. No. 5,023,262); oxidized derivatives wherein a hydroxyl group (such as the group at the 42-position) has been oxidized to the corresponding ketone (for example 42-oxorapamycin or a pharmaceutically acceptable salt, as described in U.S. Pat. No. 5,023,263); 7,29-bisdesmethyl rapamycin (U.S. Pat. No. 5,093,338); and rapamycin cleaved between the C-31 and C-32 carbons due to base degradation by a reverse aldol reaction (U.S. Pat. No. 5,138,051).

EXAMPLE 14

Radicicol and Its Analogs

"Radicicol analogs" refers to compounds structurally similar to radicicol, for example those shown in U.S. Pat. Nos. 5,731,343, 5,650,430, 4,228,079, and published international patent applications WO96/33989 and WO98/18780 which are all incorporated by reference. Particular examples of such compounds are those shown in the following structural formula:

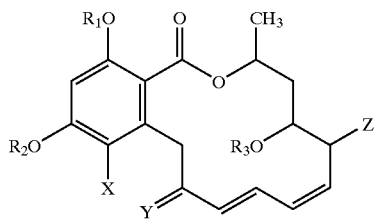

where $R_1$, $R_2$, and $R_3$ are independently selected from the group consisting of H, C1–C8 alkyl or $COR_5$. $R_5$ is chosen from the group consisting of hydrogen, substituted alkyl, alkoxy, alkenyl, substituted alkenyl, alkenyloxy, alkynyl, substituted alkynyl, aryl with 6 to 14 ring atoms, arlyoxy with 6 to 14 ring atoms, heterocyclic groups with 5 or 6 ring atoms, heterocyclic groups with 5 or 6 ring atoms fused to an aryl group, cycloalkyl, cycloalkenyl, and cycloalkyl fused to an aryl group. Specific examples of $COR_5$ are given in Table 7; any of the groups appearing in Table 7 can be used for $R_1$, $R_2$, and $R_3$. X is halogen. Y is chosen from the group consisting of O, and N—O—$R_4$, wherein $R_4$ is chosen from the group consisting of hydrogen and C1–8 alkyl. Z is halogen. Alternatively, Z can be combined with $R_3$ to form an epoxide ring.

TABLE 7

| Cpd. No. | $R^1$ | $R^2$ |
|---|---|---|
| 1 | $CH_3CH_2CO$— | $CH_3CH_2CO$— |
| 2 | $CH_3CH_2CO$— | H |
| 3 | H | $CH_3CH_2CO$— |
| 4 | $CH_3CH_2CH_2CO$— | $CH_3CH_2CH_2CO$— |
| 5 | $CH_3(CH_2)_3CO$— | $CH_3(CH_2)_3CO$— |
| 6 | $CH_3(CH_2)_4CO$— | $CH_3(CH_2)_4CO$— |
| 7 | $CH_3(CH_2)_5CO$— | $CH_3(CH_2)_5CO$— |
| 8 | H | $CH_3(CH_2)_5CO$— |
| 9 | $CH_3(CH_2)_6CO$— | $CH_3(CH_2)_6CO$— |
| 10 | H | $CH_3(CH_2)_6CO$— |
| 11 | $CH_3(CH_2)_7CO$— | $CH_3(CH_2)_7CO$— |
| 12 | H | $CH_3(CH_2)_7CO$— |
| 13 | $CH_3(CH_2)_8CO$— | $CH_3(CH_2)_8CO$— |
| 14 | H | $CH_3(CH_2)_8CO$— |
| 15 | $CH_3(CH_2)_9CO$— | $CH_3(CH_2)_9CO$— |
| 16 | H | $CH_3(CH_2)_9CO$— |
| 17 | $CH_3(CH_2)_{10}CO$— | $CH_3(CH_2)_{10}CO$— |
| 18 | H | $CH_3(CH_2)_{10}CO$— |
| 19 | $CH_3(CH_2)_{11}CO$— | $CH_3(CH_2)_{11}CO$— |
| 20 | H | $CH_3(CH_2)_{11}CO$— |
| 21 | $CH_3(CH_2)_{12}CO$— | $CH_3(CH_2)_{12}CO$— |
| 22 | H | $CH_3(CH_2)_{12}CO$— |
| 23 | $CH_3(CH_2)_{13}CO$— | $CH_3(CH_2)_{13}CO$— |
| 24 | H | $CH_3(CH_2)_{13}CO$— |
| 25 | $CH_3(CH_2)_{14}CO$— | $CH_3(CH_2)_{14}CO$— |
| 26 | $CH_3(CH_2)_{14}CO$— | H |
| 27 | H | $CH_3(CH_2)_{14}CO$— |
| 28 | $CH_3(CH_2)_{15}CO$— | $CH_3(CH_2)_{15}CO$— |
| 29 | $CH_3(CH_2)_{15}CO$— | H |
| 30 | H | $CH_3(CH_2)_{15}CO$— |
| 31 | $CH_3(CH_2)_{16}CO$— | $CH_3(CH_2)_{16}CO$— |
| 32 | $CH_3(CH_2)_{16}CO$— | H |
| 33 | H | $CH_3(CH_2)_{16}CO$— |
| 34 | $CH_3(CH_2)_{17}CO$— | $CH_3(CH_2)_{17}CO$— |
| 35 | H | $CH_3(CH_2)_{17}CO$— |
| 36 | $CH_3(CH_2)_{18}CO$— | $CH_3(CH_2)_{18}CO$— |
| 37 | H | $CH_3(CH_2)_{18}CO$— |
| 38 | $CH_3(CH_2)_{19}CO$— | $CH_3(CH_2)_{19}CO$— |
| 39 | H | $CH_3(CH_2)_{19}CO$— |
| 40 | $CH_3(CH_2)_{20}CO$— | $CH_3(CH_2)_{20}CO$— |
| 41 | H | $CH_3(CH_2)_{20}CO$— |

TABLE 7-continued

| Cpd. No. | R¹ | R² |
| --- | --- | --- |
| 42 | $(CH_3)_2CHCH_2CO-$ | $(CH_3)_2CHCH_2CO-$ |
| 43 | H | $(CH_3)_2CHCH_2CO-$ |
| 44 | $(CH_3)_3CCO-$ | $(CH_3)_3CCO-$ |
| 45 | H | $(CH_3)_3CCO-$ |
| 46 | $CH_2=CHCH_2CO-$ | $CH_2=CHCH_2CO-$ |
| 47 | H | $CH_2=CHCH_2CO-$ |
| 48 | $CH_3CH=CHCO-$ | $CH_3CH=CHCO-$ |
| 49 | H | $CH_3CH=CHCO-$ |
| 50 | $(CH_3)_2=CHCO-$ | $(CH_2)_2=CHCO-$ |
| 51 | H | $(CH_3)_2=CHCO-$ |
| 52 | $EtCH=CHCO-$ | $EtCH=CHCO-$ |
| 53 | H | $EtCH=CHCO-$ |
| 54 | $H_2C=CHCH_2CH_2CO-$ | $H_2C=CHCH_2CH_2CO-$ |
| 55 | H | $H_2C=CHCH_2CH_2CO-$ |
| 56 | $PrCH=CHCO-$ | $PrCH=CHCO-$ |
| 57 | H | $PrCH=CHCO-$ |
| 58 | $EtCH=CHCH_2CO-$ | $EtCH=CHCH_2CO-$ |
| 59 | H | $EtCH=CHCH_2CO-$ |
| 60 | $PnCH=CHCO-$ | $PnCH=CHCO-$ |
| 61 | H | $PnCH=CHCO-$ |
| 62 | $HxCH=CHCO-$ | $HxCH=CHCO-$ |
| 63 | H | $HxCH=CHCO-$ |
| 64 | $H_2C=CH(CH_2)_7CO-$ | $H_2C=CH(CH_2)_7CO-$ |
| 65 | H | $H_2C=CH(CH_2)_7CO-$ |
| 66 | $H_2C=CH(CH_2)_8CO-$ | $H_2C=CH(CH_2)_8CO-$ |
| 67 | H | $H_2C=CH(CH_2)_8CO-$ |
| 68 | $BuCH=CH(CH_2)_7CO-$ | $BuCH=CH(CH_2)_7CO-$ |
| 69 | H | $BuCH=CH(CH_2)_7CO-$ |
| 70 | $HxCH=CH(CH_2)_7CO-$ | $HxCH=CH(CH_2)_7CO-$ |
| 71 | H | $HxCH=CH(CH_2)_7CO-$ |
| 72 | $OcCH=CH(CH_2)_7CO-$ | $OcCH=CH(CH_2)_7CO-$ |
| 73 | H | $OcCH=CH(CH_2)_7CO-$ |
| 74 | $Bu(CH_2CH=CH)_2(CH_2)_7CO-$ | $Bu(CH_2CH=CH)_2(CH_2)_7CO-$ |
| 75 | H | $Bu(CH_2CH=CH)_2(CH_2)_7CO-$ |
| 76 | $Me(CH_2CH=CH)_3(CH_2)_7CO-$ | $Me(CH_2CH=CH)_3(CH_2)_7CO-$ |
| 77 | H | $Me(CH_2CH=CH)_3(CH_2)_7CO-$ |
| 78 | $Bu(CH_3CH=CH)_3(CH_2)_4CO-$ | $Bu(CH_3CH=CH)_3(CH_2)_4CO-$ |
| 79 | $Pn(CH=CHCH_2)_4(CH_2)_2CO-$ | $Pn(CH=CHCH_2)_4(CH_2)_2CO-$ |
| 80 | $Me(CH_2CH=CH)_6(CH_2)_2CO-$ | $Me(CH_2CH=CH)_6(CH_2)_2CO-$ |
| 81 | H | $Pn(CH=CHCH_2)_4(CH_2)_2CO-$ |
| 82 | $HxC(OH)H-CH_2CH=CHCO-$ | $HxC(OH)H-CH_2CH=CHCO-$ |
| 83 | H | $HxC(OH)H-CH_2CH=CHCO-$ |
| 84 | $HOCH_2(CH_2)_{14}CO-$ | $HOCH_2(CH_2)_{14}CO-$ |
| 85 | H | $HOCH_2(CH_2)_{14}CO-$ |
| 86 | $(4-MeOPh)_2PhC-OCH_2(CH_2)_{14}CO-$ | $(4-MeOPh)_2PhC-OCH_2(CH_2)_{14}CO-$ |
| 87 | H | $(4-MeOPh)_2PhC-OCH_2(CH_2)_{14}CO-$ |
| 88 | HC C.CO | HC C.CO |
| 89 | H | HC C.CO |
| 90 | MeC C.CO | MeC C.CO |
| 91 | H | MeC C.CO |
| 92 | PnC C.CO | PnC C.CO |
| 93 | H | PnC C.CO |
| 94 | $MeOCH_2CO$ | $MeOCH_2CO$ |
| 95 | $MeOCH_2CO$ | H |
| 96 | H | $MeOCH_2CO$ |
| 97 | $DdcOCH_2CH_2CO$ | $DdcOCH_2CH_2CO$ |
| 98 | H | $DdcOCH_2CH_2CO$ |
| 99 | $Meo(CH_2)_9CO$ | $Meo(CH_2)_9CO$ |
| 100 | $MeO(CH_2)_{11}CO$ | $MeO(CH_2)_{11}CO$ |
| 101 | $MeO(CH_2)_{13}CO$ | $MeO(CH_2)_{13}CO$ |
| 102 | $MeO(CH_2)_{15}CO$ | $MeO(CH_2)_{15}CO$ |
| 103 | H | $MeO(CH_2)_{13}CO$ |
| 104 | $PhOCH_2CO$ | $PhOCH_2CO$ |
| 105 | H | $PhOCH_2CO$ |
| 106 | Bz.CO | Bz.CO |
| 107 | H | Bz.CO |
| 108 | 2-PhPrn | 2-PhPrn |
| 109 | H | 2-PhPrn |
| 110 | 3-PhPrn | 3-PhPrn |
| 111 | H | 3-PhPrn |
| 112 | 6-PhHxo | 6-PhHxo |
| 113 | PhCH=CH.CO | PhCH=CH.CO |
| 114 | H | PhCH=CH.CO |
| 115 | $-Np.CH_2CO$ | $-Np.CH_2CO$ |
| 116 | H | $-Np.CH_2CO$ |
| 117 | Boz | Boz |

TABLE 7-continued

| Cpd. No. | R¹ | R² |
|---|---|---|
| 118 | H | Boz |
| 119 | 2-Fur.CO | 2-Fur.CO |
| 120 | H | 2-Fur.CO |
| 121 | 2-Fur.CH=CH.CO | 2-Fur.CH=CH.CO |
| 122 | 3-Thi.CO | 3-Thi.CO |
| 123 | H | 3-Thi.CO |
| 124 | 2-Thi.CH=CH.CO | 2-Thi.CH=CH.CO |
| 125 | 3-Thi.CO | H |
| 126 | 2-Thi.CO | 2-Thi.CO |
| 127 | H | 2-Thi.CO |
| 128 | 2-ThiCH$_2$CO | 2-ThiCH$_2$CO |
| 129 | H | 2-ThiCH$_2$CO |
| 130 | 2-NH$_2$-4-Thiz.CH$_2$CO | 2-NH$_2$-4-Thiz.CH$_2$CO |
| 131 | H | 2-NH$_2$-4-Thiz.CH$_2$CO |
| 132 | 5-oxo-2-Pyrd.CO | 5-oxo-2-Pyrd.CO |
| 133 | H | 5-oxo-2-Pyrd.CO |
| 134 | 3-Isox.CO | 3-Isox.CO |
| 135 | H | 3-Isox.CO |
| 136 | 4-Isox.CO | 4-Isox.CO |
| 137 | H | 4-Isox.CO |
| 138 | 6-oxo-2-Pip.CO | 6-oxo-2-Pip.CO |
| 139 | H | 6-oxo-2-Pip.CO |
| 140 | 3NH$_2$Prn | 3NH$_2$Prn |
| 141 | H | 3NH$_2$Prn |
| 142 | 6-NH$_2$Hxo | 6-NH$_2$Hxo |
| 143 | H | 6-NH$_2$Hxo |
| 144 | H$_2$N(CH$_2$)$_{11}$CO | H$_2$N(CH$_2$)$_{11}$CO |
| 145 | H$_2$N(CH$_2$)$_{11}$CO | H |
| 146 | H$_2$N(CH$_2$)$_{15}$CO | H$_2$N(CH$_2$)$_{15}$CO |
| 147 | H$_2$N(CH$_2$)$_{15}$CO | H |
| 148 | TrocNH(CH$_2$)$_2$CO | TrocNH(CH$_2$)$_2$CO |
| 149 | TrocNH(CH$_2$)$_2$CO | H |
| 150 | TrocNH(CH$_2$)$_5$CO | TrocNH(CH$_2$)$_5$CO |
| 151 | TrocNH(CH$_2$)$_5$CO | H |
| 152 | TrocNH(CH$_2$)$_{11}$CO | TrocNH(CH$_2$)$_{11}$CO |
| 153 | H | TrocNH(CH$_2$)$_{11}$CO |
| 154 | TrocNH(CH$_2$)$_{15}$CO | TrocNH(CH$_2$)$_{15}$CO |
| 155 | H | TrocNH(CH$_2$)$_{15}$CO |
| 156 | AocNH(CH$_2$)$_2$CO | AocNH(CH$_2$)$_2$CO |
| 157 | H | AocNH(CH$_2$)$_2$CO |
| 158 | AocNH(CH$_2$)$_5$CO | AocNH(CH$_2$)$_5$CO |
| 159 | AocNH(CH$_2$)$_5$CO | H |
| 160 | AocNH(CH$_2$)$_{11}$CO | AocNH(CH$_2$)$_{11}$CO |
| 161 | H | AocNH(CH$_2$)$_{11}$CO |
| 162 | AocNH(CH$_2$)$_{15}$CO | AocNH(CH$_2$)$_{15}$CO |
| 163 | H | AocNH(CH$_2$)$_{15}$CO |
| 164 | FmocNH(CH$_2$)$_{11}$CO | FmocNH(CH$_2$)$_{11}$CO |
| 165 | Ph$_3$C.S.NH(CH$_2$)$_{11}$CO | Ph$_3$C.S.NH(CH$_2$)$_{11}$CO |
| 166 | ClCH$_2$CO | ClCH$_2$CO |
| 167 | H | ClCH$_2$CO |
| 168 | FCH$_2$CO | FCH$_2$CO |
| 169 | H | FCH$_2$CO |
| 170 | BrCH$_2$CO | BrCH$_2$CO |
| 171 | H | BrCH$_2$CO |
| 172 | BrCH$_2$CO | H |
| 173 | ICH$_2$CO | ICH$_2$CO |
| 174 | ICH$_2$CO | H |
| 175 | H | ICH$_2$CO |
| 176 | MeSCH$_2$CO | MeSCH$_2$CO |
| 177 | H | MeSCH$_2$CO |
| 178 | MeS(CH$_2$)$_2$CO | MeS(CH$_2$)$_2$CO |
| 179 | MeS(CH$_2$)$_9$CO | MeS(CH$_2$)$_9$CO |
| 180 | MeS(CH$_2$)$_{11}$CO | MeS(CH$_2$)$_{11}$CO |
| 181 | MeS(CH$_2$)$_{15}$CO | MeS(CH$_2$)$_{15}$CO |
| 182 | MeSO$_2$CH$_2$CO | MeSO$_2$CH$_2$CO |
| 183 | H | MeSO$_2$CH$_2$CO |
| 184 | MeSO$_2$(CH$_2$)$_9$CO | MeSO$_2$(CH$_2$)$_9$CO |
| 185 | MeSO$_2$(CH$_2$)$_{12}$CO | MeSO$_2$(CH$_2$)$_{12}$CO |
| 186 | MeSO$_2$(CH$_2$)$_{15}$CO | MeSO$_2$(CH$_2$)$_{15}$CO |
| 187 | MeSO.CH$_2$CO | MeSO.CH$_2$CO |
| 188 | H | MeSO.CH$_2$CO |
| 189 | MeSO(CH$_2$)$_9$CO | MeSO(CH$_2$)$_9$CO |
| 190 | MeSO(CH$_2$)$_{11}$CO | MeSO(CH$_2$)$_{11}$CO |
| 191 | MeSO$_2$(CH$_2$)$_{15}$CO | MeSO$_2$(CH$_2$)$_{15}$CO |
| 192 | HXS.CH$_2$CO | HXS.CH$_2$CO |
| 193 | H | HXS.CH$_2$CO |

TABLE 7-continued

| Cpd. No. | R¹ | R² |
|---|---|---|
| 194 | DdcS.CH$_2$CO | DdcS.CH$_2$CO |
| 195 | H | DdcS.CH$_2$CO |
| 196 | PhS.CH$_2$CO | PhS.CH$_2$CO |
| 197 | H | PhS.CH$_2$CO |
| 198 | PhS(CH$_2$)$_9$CO | PhS(CH$_2$)$_9$CO |
| 199 | PhS(CH$_2$)$_{11}$CO | PhS(CH$_2$)$_{11}$CO |
| 200 | PhS(CH$_2$)$_{15}$CO | PhS(CH$_2$)$_{15}$CO |
| 201 | 2-PhEt.S.CH$_2$CO | 2-PhEt.S.CH$_2$CO |
| 202 | H | 2-PhEt.S.CH$_2$CO |
| 203 | Bz.SS.CH$_2$CO | Bz.SS.CH$_2$CO |
| 204 | H | Bz.SS.CH$_2$CO |
| 205 | Bz.SS.(CH$_2$)$_9$CO | Bz.SS.(CH$_2$)$_9$CO |
| 206 | Bz.SS.(CH$_2$)$_{11}$CO | Bz.SS.(CH$_2$)$_{11}$CO |
| 207 | Bz.SS.(CH$_2$)$_{15}$CO | Bz.SS.(CH$_2$)$_{15}$CO |
| 208 | Et$_2$NCH$_2$CO | Et$_2$NCH$_2$CO |
| 209 | Et$_2$NCH$_2$CO | H |
| 210 | Et$_2$N(CH$_2$)$_9$CO | Et$_2$N(CH$_2$)$_9$CO |
| 211 | Et$_2$N(CH$_2$)$_{11}$CO | Et$_2$N(CH$_2$)$_{11}$CO |
| 212 | Et$_2$N(CH$_2$)$_{15}$CO | Et$_2$N(CH$_2$)$_{15}$CO |
| 213 | 1-Me-4-Piz.CH$_2$CO | 1-Me-4-Piz.CH$_2$CO |
| 214 | H | 1-Me-4-Piz.CH$_2$CO |
| 215 | 1-Me-4-Piz.(CH$_2$)$_{15}$CO | 1-Me-4-Piz.(CH$_2$)$_{15}$CO |
| 216 | Me$_2$N(CH$_2$)$_9$CO | Me$_2$N(CH$_2$)$_9$CO |
| 217 | Me$_2$N(CH$_2$)$_{11}$CO | Me$_2$N(CH$_2$)$_{11}$CO |
| 218 | Me$_2$N(CH$_2$)$_{15}$CO | Me$_2$N(CH$_2$)$_{15}$CO |
| 219 | 4-Mor.CH$_2$CO | 4-Mor.CH$_2$CO |
| 220 | 4-Mor.CH$_2$CO | H |
| 221 | 4-Mor.(CH$_2$)$_{15}$CO | 4-Mor.(CH$_2$)$_{15}$CO |
| 222 | 4-Mor.(CH$_2$)$_{15}$CO | H |
| 223 | 1-Pyrd.CH$_2$CO | 1-Pyrd.CH$_2$CO |
| 224 | H | 1-Pyrd.CH$_2$CO |
| 225 | 1-Pyrd.(CH$_2$)$_{15}$CO | 1-Pyrd.(CH$_2$)$_{15}$CO |
| 226 | H | 1-Pyrd.(CH$_2$)$_{15}$CO |
| 227 | Etc(CH$_2$)$_{12}$CO | Etc(CH$_2$)$_{12}$CO |
| 228 | H | Etc(CH$_2$)$_{12}$CO |
| 229 | Mec(CH$_2$)$_{10}$CO | Mec(CH$_2$)$_{10}$CO |
| 230 | Car(CH$_2$)$_{12}$CO | Car(CH$_2$)$_{12}$CO |
| 231 | H | Car(CH$_2$)$_{12}$CO |
| 232 | Car(CH$_2$)$_{10}$CO | Car(CH$_2$)$_{10}$CO |
| 233 | Car(CH$_2$)$_{14}$CO | Car(CH$_2$)$_{14}$CO |
| 234 | HOOC(CH$_2$)$_{12}$CO | HOOC(CH$_2$)$_{12}$CO |
| 235 | HOOC(CH$_2$)$_{12}$CO | H |
| 236 | NC(CH$_2$)$_{10}$CO | NC(CH$_2$)$_{10}$CO |
| 237 | NC(CH$_2$)$_{15}$CO | NC(CH$_2$)$_{15}$CO |
| 238 | HO(CH$_2$)$_2$CO | HO(CH$_2$)$_2$CO |
| 239 | H | HO(CH$_2$)$_2$CO |
| 240 | HO(CH$_2$)$_5$CO | HO(CH$_2$)$_5$CO |
| 241 | H | HO(CH$_2$)$_5$CO |
| 242 | HO(CH$_2$)$_9$CO | HO(CH$_2$)$_9$CO |
| 243 | H | HO(CH$_2$)$_9$CO |
| 244 | HO(CH$_2$)$_{11}$CO | HO(CH$_2$)$_{11}$CO |
| 245 | H | HO(CH$_2$)$_{11}$CO |
| 246 | HO(CH$_2$)$_{15}$CO | HO(CH$_2$)$_{15}$CO |
| 247 | H | HO(CH$_2$)$_{15}$CO |
| 248 | MemO(CH$_2$)$_9$CO | MemO(CH$_2$)$_9$CO |
| 249 | MemO(CH$_2$)$_{11}$CO | MemO(CH$_2$)$_{11}$CO |
| 250 | MemO(CH$_2$)$_{15}$CO | MemO(CH$_2$)$_{15}$CO |
| 251 | MomO(CH$_2$)$_9$CO | MomO(CH$_2$)$_9$CO |
| 252 | MomO(CH$_2$)$_{11}$CO | MomO(CH$_2$)$_{11}$CO |
| 253 | MomO(CH$_2$)$_{15}$CO | MomO(CH$_2$)$_{15}$CO |
| 254 | HS(CH$_2$)$_2$CO | HS(CH$_2$)$_2$CO |
| 255 | HS(CH$_2$)$_2$CO | H |
| 256 | HS(CH$_2$)$_5$CO | HS(CH$_2$)$_5$CO |
| 257 | HS(CH$_2$)$_5$CO | H |
| 258 | HS(CH$_2$)$_{11}$CO | HS(CH$_2$)$_{11}$CO |
| 259 | HS(CH$_2$)$_{11}$CO | H |
| 260 | HS(CH$_2$)$_{15}$CO | HS(CH$_2$)$_{15}$CO |
| 261 | HS(CH$_2$)$_{15}$CO | H |
| 262 | Ac.S(CH$_2$)$_9$CO | Ac.S(CH$_2$)$_9$CO |
| 263 | Ac.S(CH$_2$)$_{11}$CO | Ac.S(CH$_2$)$_{11}$CO |
| 264 | Ac.S(CH$_2$)$_{15}$CO | Ac.S(CH$_2$)$_{15}$CO |
| 265 | 4-PrBoz | 4-PrBoz |
| 266 | H | 4-PrBoz |
| 267 | 4-PhByr | 4-PhByr |
| 268 | 4-PhByr | H |
| 269 | 6-PhHxo | 6-PhHxo |

TABLE 7-continued

| Cpd. No. | R¹ | R² |
|---|---|---|
| 270 | 6-PhHxo | H |
| 271 | MecCH(NHAc).(CH$_2$)$_{10}$CO | MecCH(NHAc).(CH$_2$)$_{10}$CO |
| 272 | MecCH(NHAc).(CH$_2$)$_{12}$CO | MecCH(NHAc).(CH$_2$)$_{12}$CO |
| 273 | MecCH(NHAc).(CH$_2$)$_{16}$CO | MecCH(NHAc).(CH$_2$)$_{16}$CO |
| 274 | 1-Ind.CO | 1-Ind.CO |
| 275 | 1-Ind.CO | H |
| 276 | 1-(4H-cOc)CO | 1-(4H-cOc)CO |
| 277 | 1-(4H-cOc)CO | H |
| 278 | 2-PhOPrn | 2-PhOPrn |
| 279 | 2-PhOPrn | H |
| 280 | 3-Pyr.CH=CHCO | 3-Pyr.CH=CHCO |
| 281 | 3-Pyr.CH=CHCO | H |
| 282 | 2-Pyr.CH$_2$CO | 2-Pyr.CH$_2$CO |
| 283 | 2-Pyr.CH$_2$CO | H |
| 284 | 2-HXDco | 2-HXDco |
| 285 | H | 2-HXDco |
| 286 | 2-PnHpo | 2-PnHpo |
| 287 | H | 2-PnHpo |
| 288 | Me(CH$_2$)$_{14}$CO | Me(CH$_2$)$_{16}$CO |
| 289 | Me(CH$_2$)$_{16}$CO | Me(CH$_2$)$_{14}$CO |
| 290 | Me(CH$_2$)$_{16}$CO | OcCH=CH(CH$_2$)$_7$CO |
| 291 | Me(CH$_2$)$_{16}$CO | Me(CH$_2$)$_{12}$CO |
| 292 | Me(CH$_2$)$_{16}$CO | CH$_2$=CH(CH$_2$)$_8$CO |
| 293 | cPrCO | cPrCO |
| 294 | H | cPrCO |
| 295 | cBuCO | cBuCO |
| 296 | H | cBuCO |
| 297 | cPnCO | cPnCO |
| 298 | H | cPnCO |
| 299 | cPnCO | H |
| 300 | cHxCO | cHxCO |
| 301 | H | cHxCO |
| 302 | cHxCO | H |
| 303 | cHpCO | cHpCO |
| 304 | H | cHpCO |
| 305 | cOcCO | H |
| 306 | cOcCO | cOcCO |
| 307 | H | cOcCO |
| 308 | 1-cPenCO | 1-cPenCO |
| 309 | H | 1-cPenCO |
| 310 | 3-cHexCO | 3-cHexCO |
| 311 | H | 3-cHexCO |
| 312 | 3-cHexCO | H |
| 313 | 4-cHexCO | 4-cHexCO |
| 314 | 1-cHexCO | 1-cHexCO |
| 315 | 2-HOcPnCO | 2-HOcPnCO |
| 316 | 2-HOcPnCO | H |
| 317 | 4-NH$_2$cHxCO | 4-NH$_2$cHxCO |
| 318 | 4-NH$_2$cHxCO | H |
| 319 | 2-ClcHxCO | 2-ClcHxCO |
| 320 | Retio | Retio |
| 321 | H | Retio |
| 322 | Retio | H |
| 323 | Me(CH$_2$)$_{14}$CO | OcCH=CH(CH$_2$)$_7$CO |
| 324 | Me(CH$_2$)$_{14}$CO | Me(CH$_2$)$_{12}$CO |
| 325 | Me(CH$_2$)$_{14}$CO | CH$_2$=CH(CH$_2$)$_8$CO |
| 326 | Me$_3$SiCH$_2$CH$_2$OCH$_2$O(CH$_2$)$_{15}$CO | Me$_3$SiCH$_2$CH$_2$OCH$_2$O(CH$_2$)$_{15}$CO |
| 327 | MeSCH$_2$O(CH$_2$)$_9$CO | MeSCH$_2$O(CH$_2$)$_9$CO |
| 328 | MeSCH$_2$O(CH$_2$)$_{11}$CO | MeSCH$_2$O(CH$_2$)$_{11}$CO |
| 329 | MeSCH$_2$O(CH$_2$)$_{15}$CO | MeSCH$_2$O(CH$_2$)$_{15}$CO |

EXAMPLE 15

Bastadins and Their Analogs

"Bastadins" refer to any bastadin presently known, or discovered in the future. A compound from the bastadin family refers to subunits of the bastadins, such as halogenated tyrosines, including bromotyrosines and the 3-bromotyramine amide of oxalic acid amide. A bastadin also includes the hemibastadins, which represent bromotyrosine dimers. The hemibastadins include hemibastadins 1, 2, and 3 as well as hemibastadinols 1.2, and 3.

The methods of the present invention, for improving neurite outgrowth, include the use of any bastadin or any member of the bastadin family, or their analogs in any aspect of the invention (including their use in assays to search for other neurotrophic compounds).

Particular examples of bastadins and other members of the bastadin family include those shown in Pettit et al., *J. Nat. Prod.*, 59(10): 927–34, 1996; Franklin et al., *J. Nat. Prod.*, 59(12): 1121–7, 1996; Pettit et al., *J. Nat. Prod.*, 58(5): 680–8, 1995; Mack et al., *J. Biol. Chem.*, 269(37): 23236–49, 1994; Gulavita et al., *J. Nat. Prod.*, 56(9): 1613–7, 1993: Carney and Scheuer, *J. Nat. Prod.*, 56(1):

153–7, 1993; and Miao and Andersen, *J. Nat. Prod.*, 53(6), 1990, which are incorporated by reference.

Particular examples of bastadins and their analogs include bastadins of the formula where the identity and substitution patterns of some particular bastadins and bastadin analogs are given in Table 8 below.

TABLE 8

Substitution Patterns for Some Bastadins and Bastadin Analogs

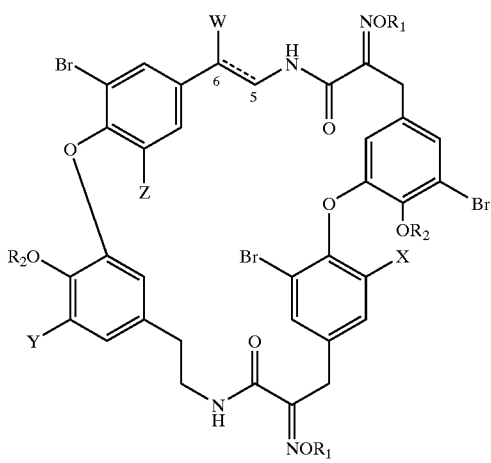

| compound | R$_1$ | R$_2$ | W | X | Y | Z | C5, 6 |
|---|---|---|---|---|---|---|---|
| Basdadin 4 | H | H | H | Br | Br | H | Δ |
| Bastadin 4 tetra-O—Me | Me | Me | H | Br | Br | H | Δ |
| Bastadin 5 | H | H | H | Br | Br | H | — |
| Bastadin 5 di-O—Me | Me | H | H | Br | Br | H | — |
| Bastadin 5 tetra-O—Me | Me | Me | H | Br | Br | H | — |
| Bastadin 6 | H | H | H | Br | Br | Br | — |
| Bastadin 6 tetra-O—Me | Me | Me | H | Br | Br | Br | — |
| Bastadin 7 | H | H | H | H | Br | H | Δ |
| 15,34-disulfatobastadin 7 | H | SO$_3$Na | H | H | Br | H | Δ |
| Bastadin 8 | H | H | OH | Br | Br | H | — |
| Bastadin 8 tetra-O—Me | Me | Me | OH | Br | Br | H | — |
| Bastadin 9 | H | H | OH | H | Br | Br | — |
| Bastadin 9 tetra-O—Me | Me | Me | OH | H | Br | Br | — |
| Bastadin 10 | H | H | OH | H | Br | H | — |
| Bastadin 11 | H | H | H | Br | H | H | Δ |
| Bastadin 12 | H | H | OH | H | Br | Br | — |
| Bastadin 14 | H | H | H | H | Br | Br | Δ |
| Bastadin 14 tetra-O—Me | Me | Me | H | H | Br | Br | Δ |
| Bastadin 15 | H | H | H | H | Br | Br | — |
| Bastadin 15 di-O—Me | Me | H | H | H | Br | Br | — |
| Bastadin 15 tetra-O—Me | Me | Me | H | H | Br | Br | — |
| Bastadin 18 | H | H | H | H | Br | Br | — |

Other particular examples of bastadins include compounds of the structure, where the identity and substitution patterns of some particular bastadins and bastadin analogs are given in Table 9 below.

TABLE 9

Substitution Patterns for Some Bastadins and Bastadin Analogs

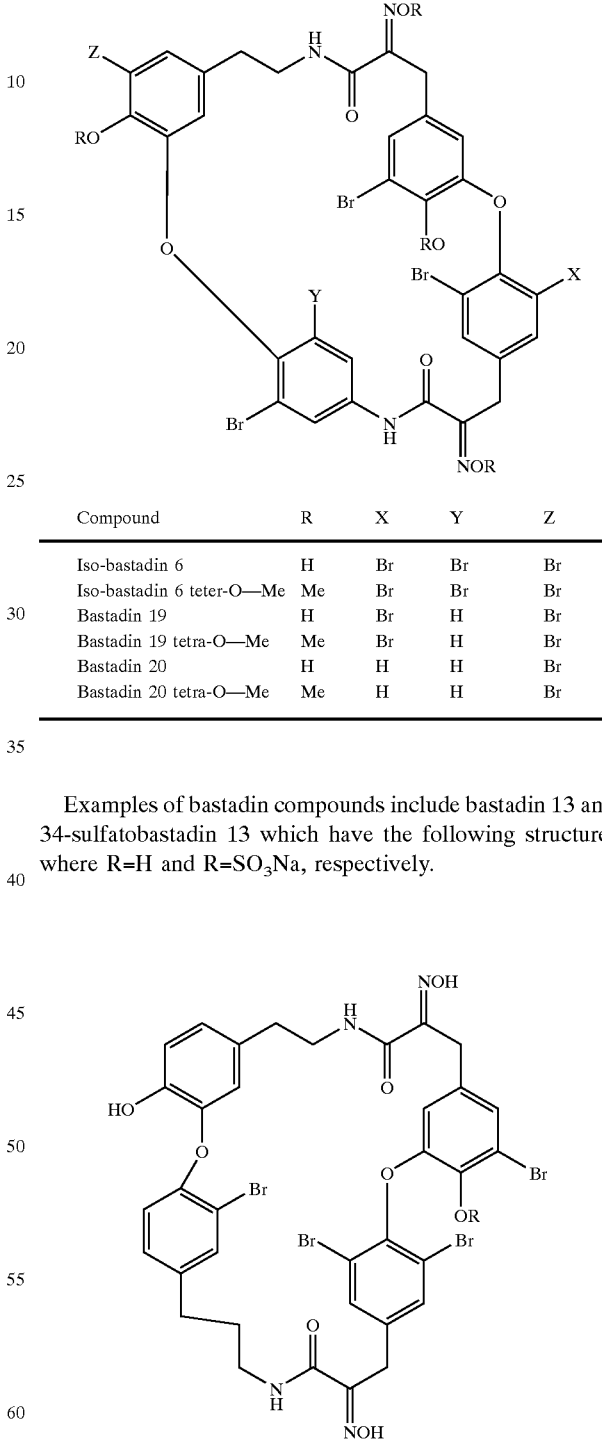

| Compound | R | X | Y | Z |
|---|---|---|---|---|
| Iso-bastadin 6 | H | Br | Br | Br |
| Iso-bastadin 6 teter-O—Me | Me | Br | Br | Br |
| Bastadin 19 | H | Br | H | Br |
| Bastadin 19 tetra-O—Me | Me | Br | H | Br |
| Bastadin 20 | H | H | H | Br |
| Bastadin 20 tetra-O—Me | Me | H | H | Br |

Examples of bastadin compounds include bastadin 13 and 34-sulfatobastadin 13 which have the following structure, where R=H and R=SO$_3$Na, respectively.

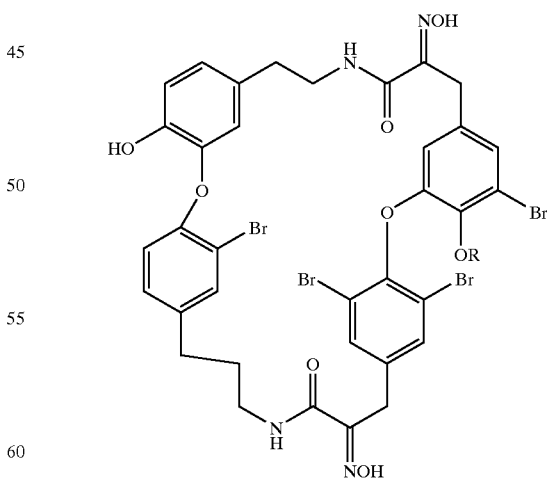

Particular examples of bastadins that are of an open-ring structure exist and include bastadins 1 and 2 which have the following structure, where X=H and X=Br respectively.

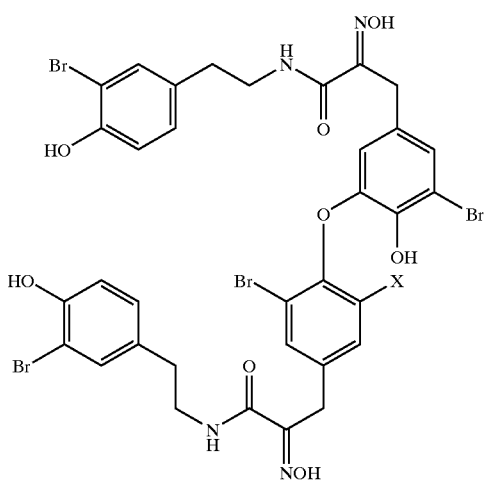

Bastadin 3 and 10-sulfatobastadin 3 also possess an open-ring structure. They have the following formulae, where R=H for bastadin 3 and R=SO₃Na for 10-sulfatobastadin 3.

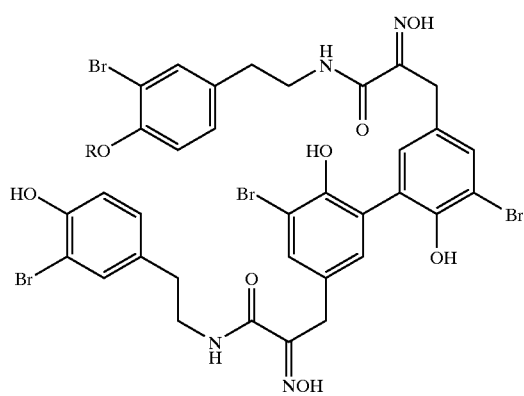

Another example of a compound in the bastadin family is the 3-bromotyramine amide of oxalic acid amid which has the following structure, where R can for example be H or COCH₃.

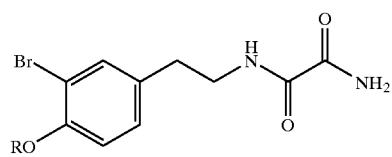

The bastadins also include the hemibastadins, some of which can be described by the following structure, where the identities and substitution patterns are defined in Table 10.

TABLE 10

Substitution Patterns for Some Hemibastadins and Analogs Thereof

| Compound | X | Y | R₁ | R₂ |
|---|---|---|---|---|
| Hemibastadin 1 | H | H | H | H |
| Hemibastadin 2 | H | Br | H | H |
| Hemibastadin 3 | Br | H | H | H |
| Analog 1 | H | Br | Me | Me |
| Analog 2 | H | H | Me | Me |
| Analog 3 | Br | H | Me | Me |
| Analog 4 | H | H | Me | H |
| Analog 5 | H | Br | Me | H |

The bastadins also include the hemibastadinols, some of which have the following structure. The identity and substitution patterns of several examples are given below in Table 11.

TABLE 11

Substitution Patterns for Some Hemibastadinols and Their Analogs

| compound | X | Y | R₁ | R₂ |
|---|---|---|---|---|
| Hemibastadinaol 1 | H | H | H | H |
| Analog 1 | H | H | Me | H |
| Hemibastadinol 2 | H | Br | H | H |
| Hemibastadinol 3 | Br | H | H | H |
| Analog 2 | H | Br | Me | H |
| Analog 3 | Br | H | Me | H |

EXAMPLE 16

Effect of Radicicol on Neurite Outgrowth

Figure 3:
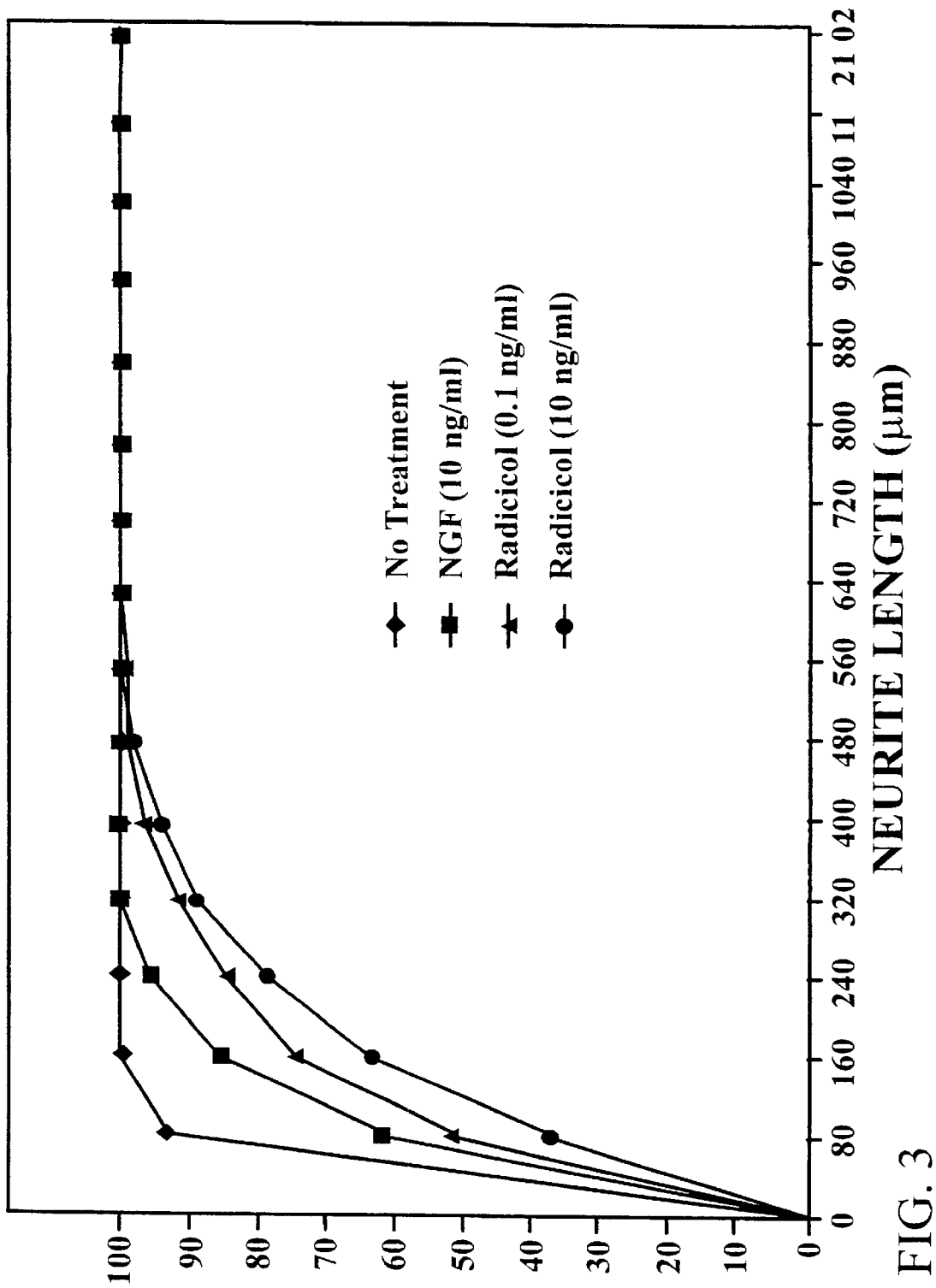
FIG. 3 is a cumulative histogram showing neurite outgrowth lengths after72 hours for untreated hippocamapal cells and for hippocampal cells treated with either NGF or radicicol at the concentrations indicated.

Utilizing the in vitro assay described in Example 2, the effect of radicicol on neurite outgrowth was investigated. Hippocampal cells were treated with radicicol at a concentration of 0.1 ng/mL and at a concentration of 10 ng/mL. The neurite outgrowth for radicicol treated cells was compared to the outgrowth for untreated cells and for cells treated with 10 ng/mL of NGF. The results are shown in FIG. 3. A shift of the histogram to the right indicates increased stimulation of neurite outgrowth and it can be seen that radicicol alone (at both concentrations) is more effective than NGF alone in stimulating outgrowth.

EXAMPLE 17

Effect of Heat on Neurite Outgrowth

Figure 4:
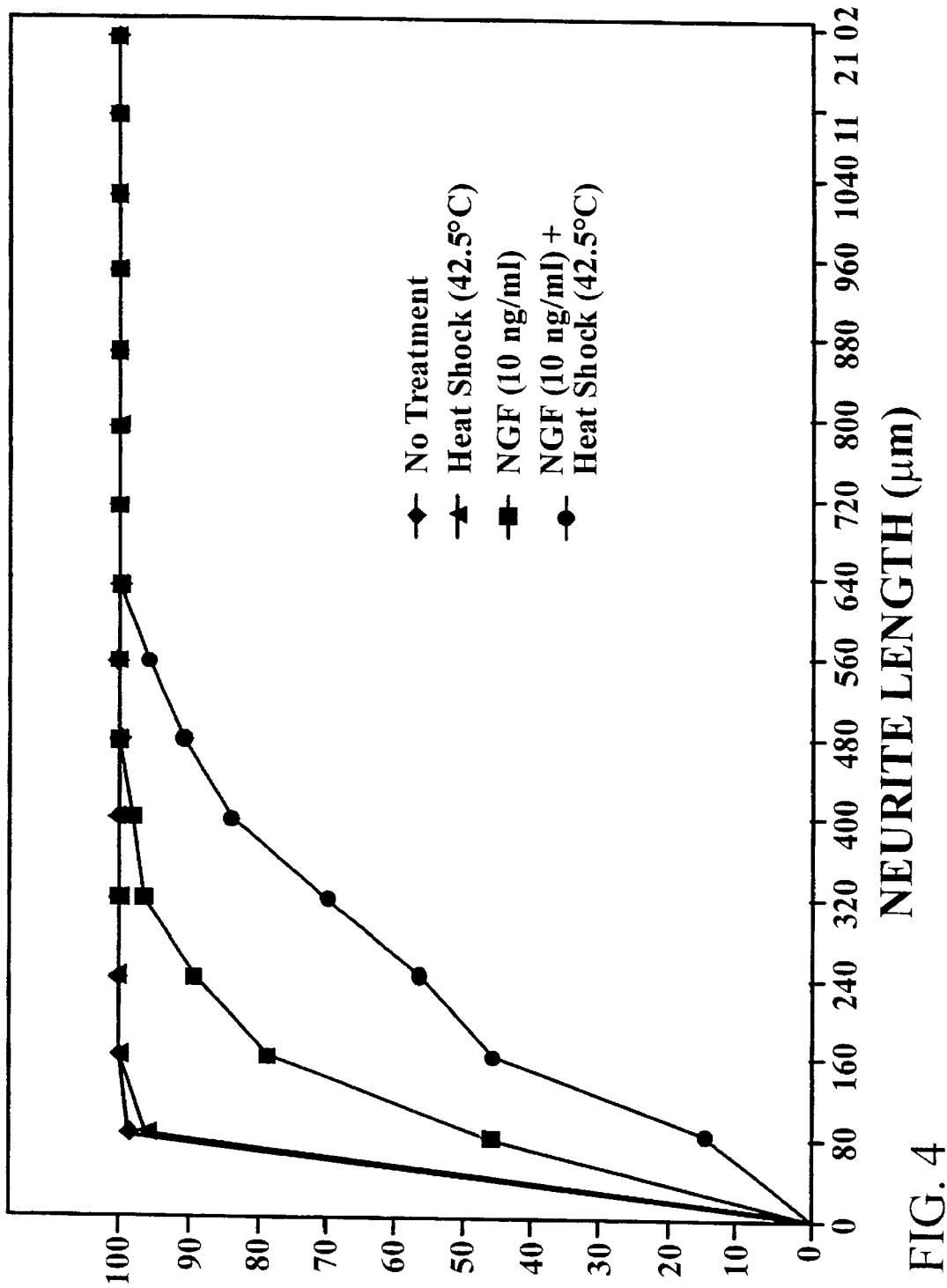
FIG. 4 is a cumulative histogram showing neurite outgrowth lengths after 72 hours for untreated hippocampal cells and for hippocampal cells treated with heat, NGF, or a combination of heat and NGF.
Figure 5:
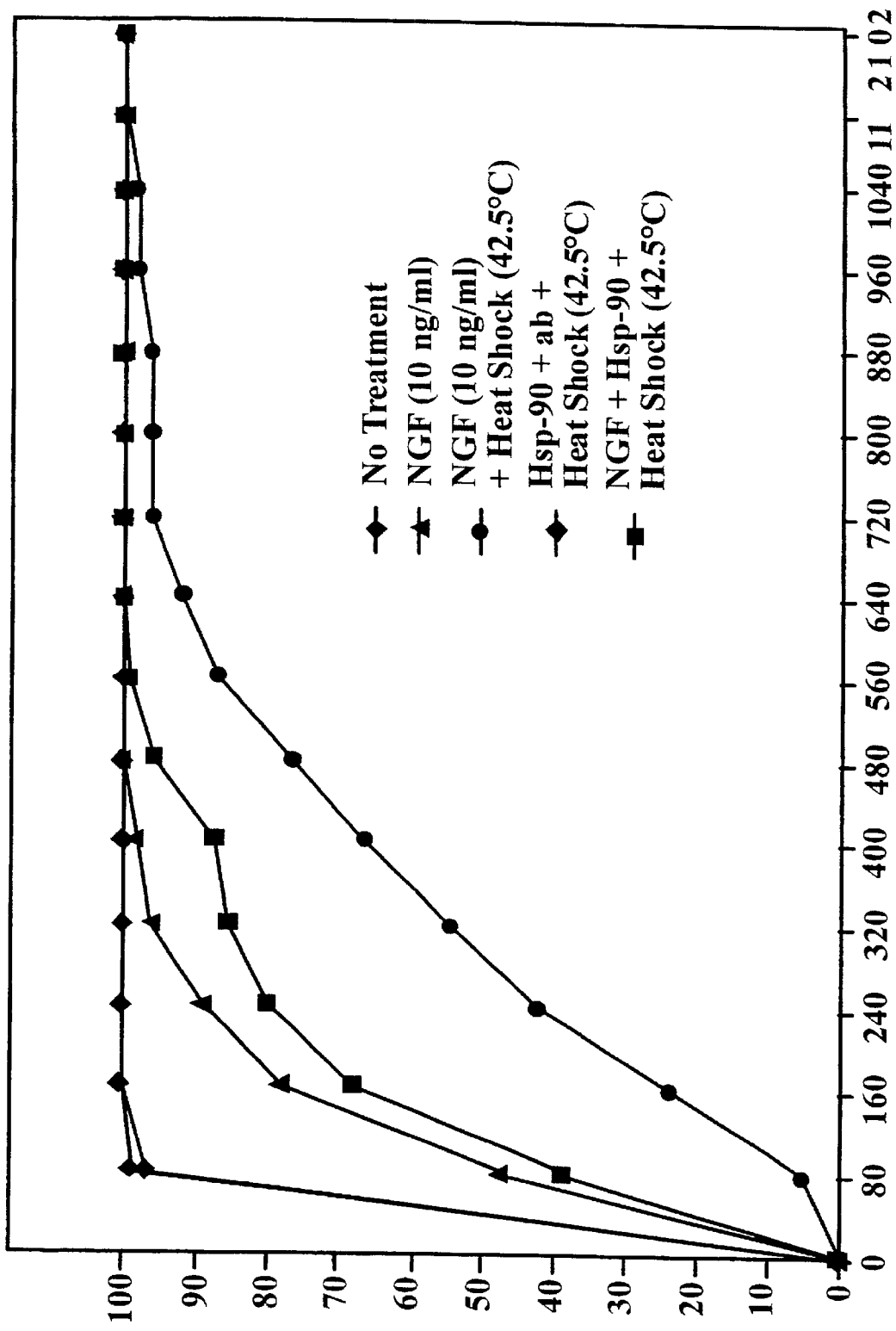
FIG. 5 is a cumulative histogram showing neurite outgrowth lengths after 72 hours for untreated hippocampal cells and for hippocampal cells treated with NGF, a combination of heat and NGF, a combination of heat and Hsp-90 antibodies (Ab), and a combination of heat, NGF, and Hsp-90 antibodies.

Utilizing the in vitro assay described in Example 2, the effect of heat alone or in combination with various compounds on neurite outgrowth was investigated. FIG. 4 shows that heat in combination with NGF treatment is more effective than either heat or NGF treatment alone in stimulating neurite outgrowth for the hippocampal cells tested. FIG. 5 shows that heat treatment is more effective when administered in combination with NGF than when administered in combination with an Hsp-90 Antibodies. FIG. 5 also illustrates that a combination of heat treatment and treatment with both NGF, and Hsp-90 antibodies is not as effective as the combination of heat and NGF treatment. Involvment of Hsp-90 as a mediator of the heat shock effect is demonstrated by the ability of the Hsp-90 antibody to inhibit the increase in neurite outgrowth.

EXAMPLE 18

Role of MAP Kinase/Kinase

Figure 6:
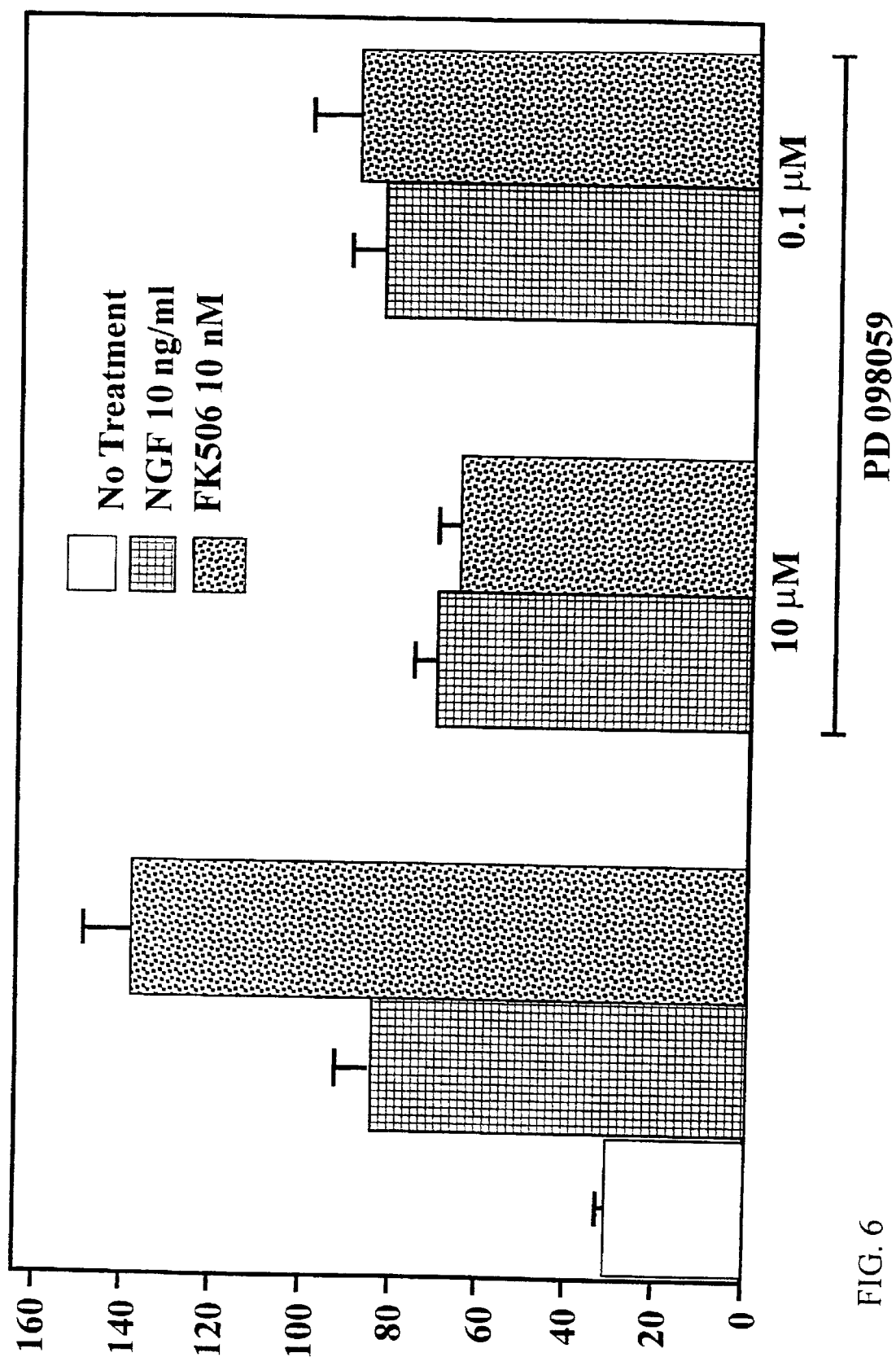
FIG. 6 is a histogram showing the mean neurite length after 72 hours for untreated hippocampal cells and for hippocampal cells treated with NGF, FK506, combinations of NGF and the MAP kinase/kinase inhibitor PD 098059 (2 concentrations), and combinations of FK506 and PD 098059 (2 concentrations).
Figure 7:
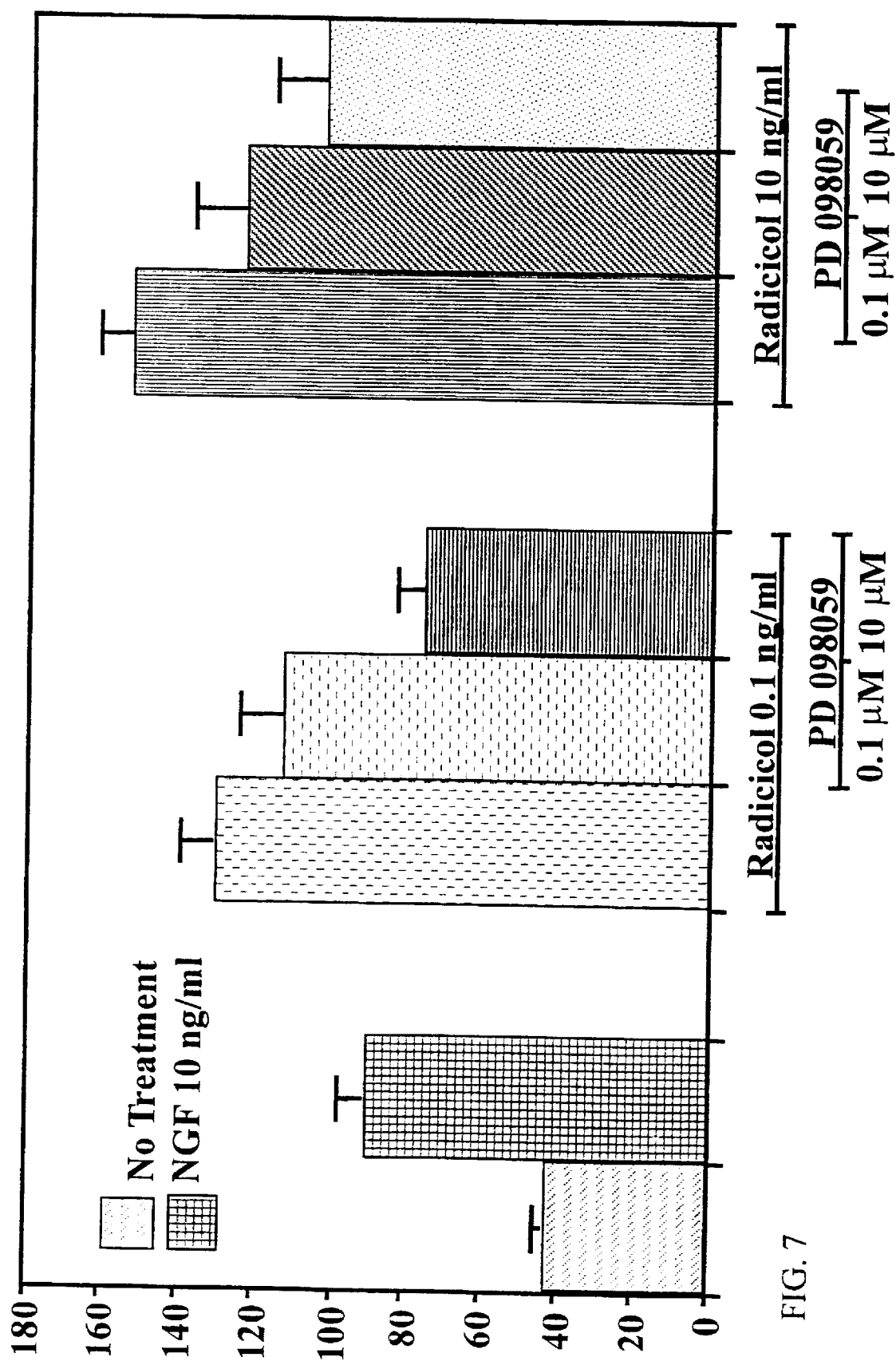
FIG. 7 is a histogram showing the mean neurite length after 72 hours for untreated hippocampal cells and for hippocampal cells treated with NGF and various combinations of radicicol (2 concentrations) and PD 098059 (2 concentrations).
Figure 8:
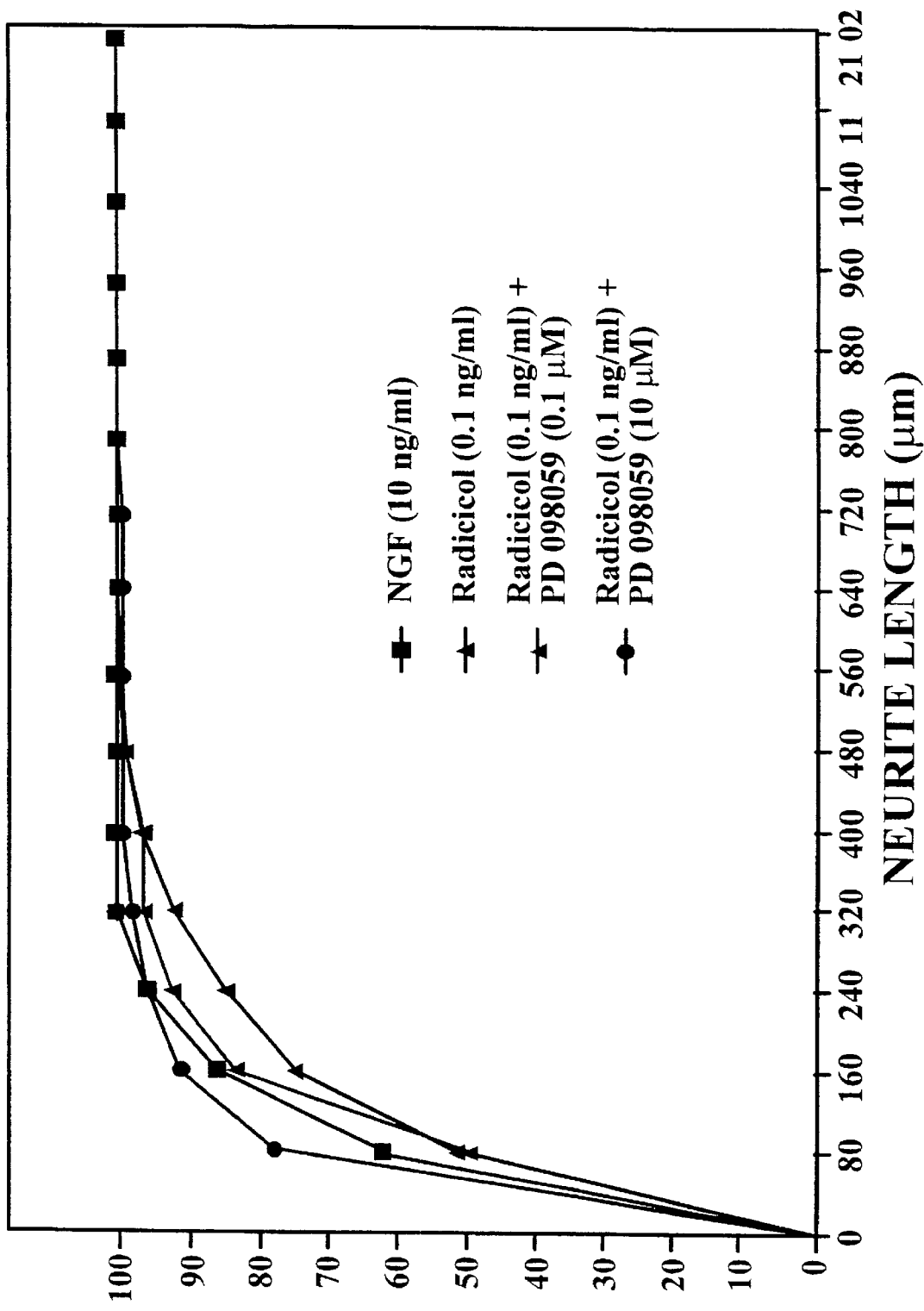
FIG. 8 is a cumulative histogram showing neurite outgrowth lengths after 72 hours for hippocampal cells treated with NGF, radicicol and two combinations of radicicol and the MAP Kinase/Kinase inhibitor PD 098059.

The role of MAP Kinase/Kinase was investigated utilizing the in vitro assay described in Example 2. Hippocampal cells were treated with the MAP kinase/kinase inhibitor PD 098059 in combination with NGF, FK506, and radicicol to determine if there is down-stream involvement of the MAP kinase pathway in the action of each of these compounds. In FIG. 6 it can be seen that the selective MAP kinase/kinase (MEK) inhibitor blocks neurite outgrowth by NGF and FK-506 in a concentration dependent fashion. FIG. 7 illustrates that PD 098059 also blocks the action of radicicol in a concentration dependent fashion and the highest concentration almost completely blocks activity.

EXAMPLE 19

Effect of Bastadin on Neurite Outgrowth

Figure 9A:
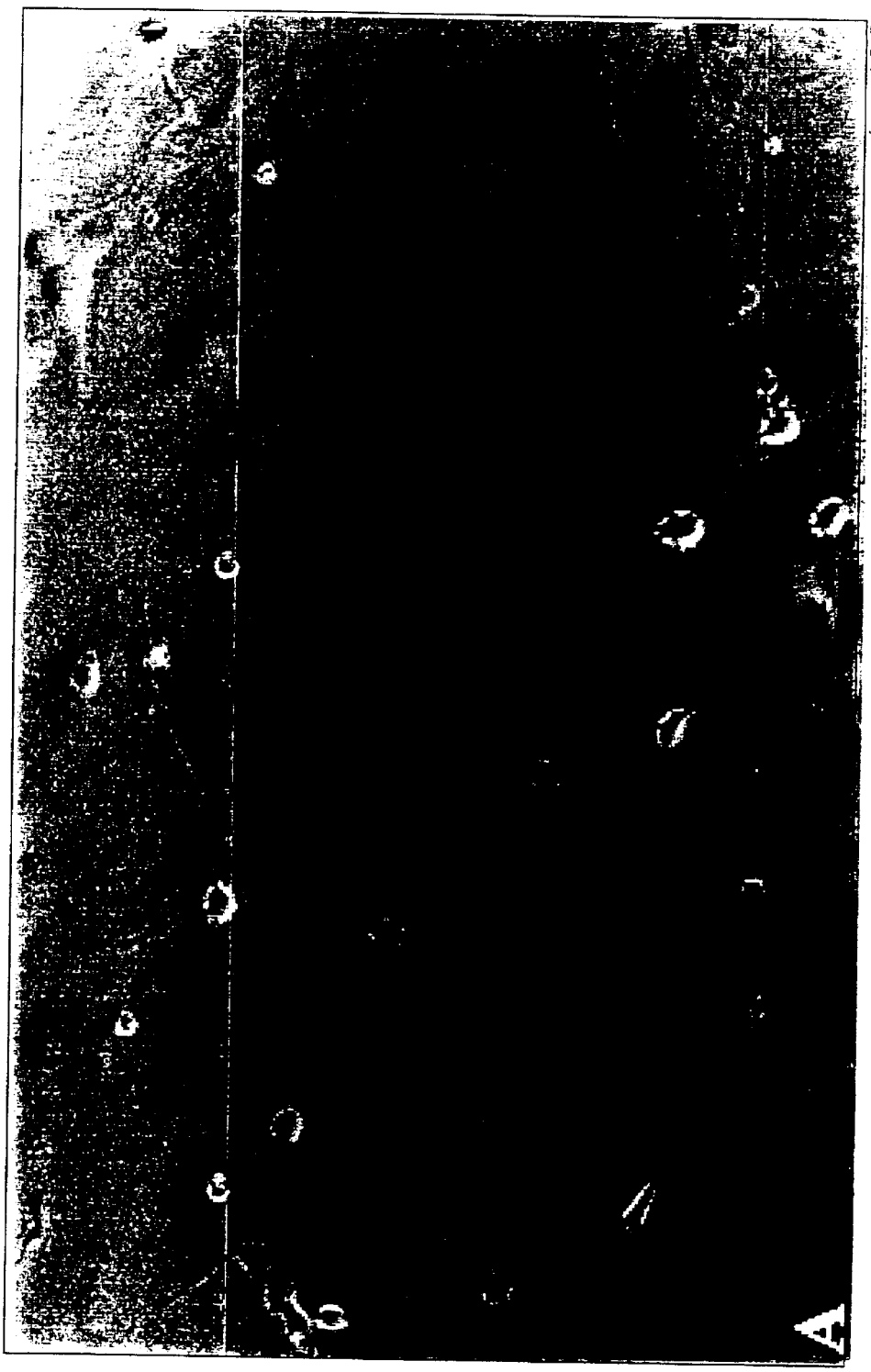
FIGS. 9A, 9B, and 9C are light micrographs showing hippocampal cells after 72 hours for untreated cells, cells treated with radicicol, and cells treated with a bastadin 10 analog, respectively.
Figure 9B:
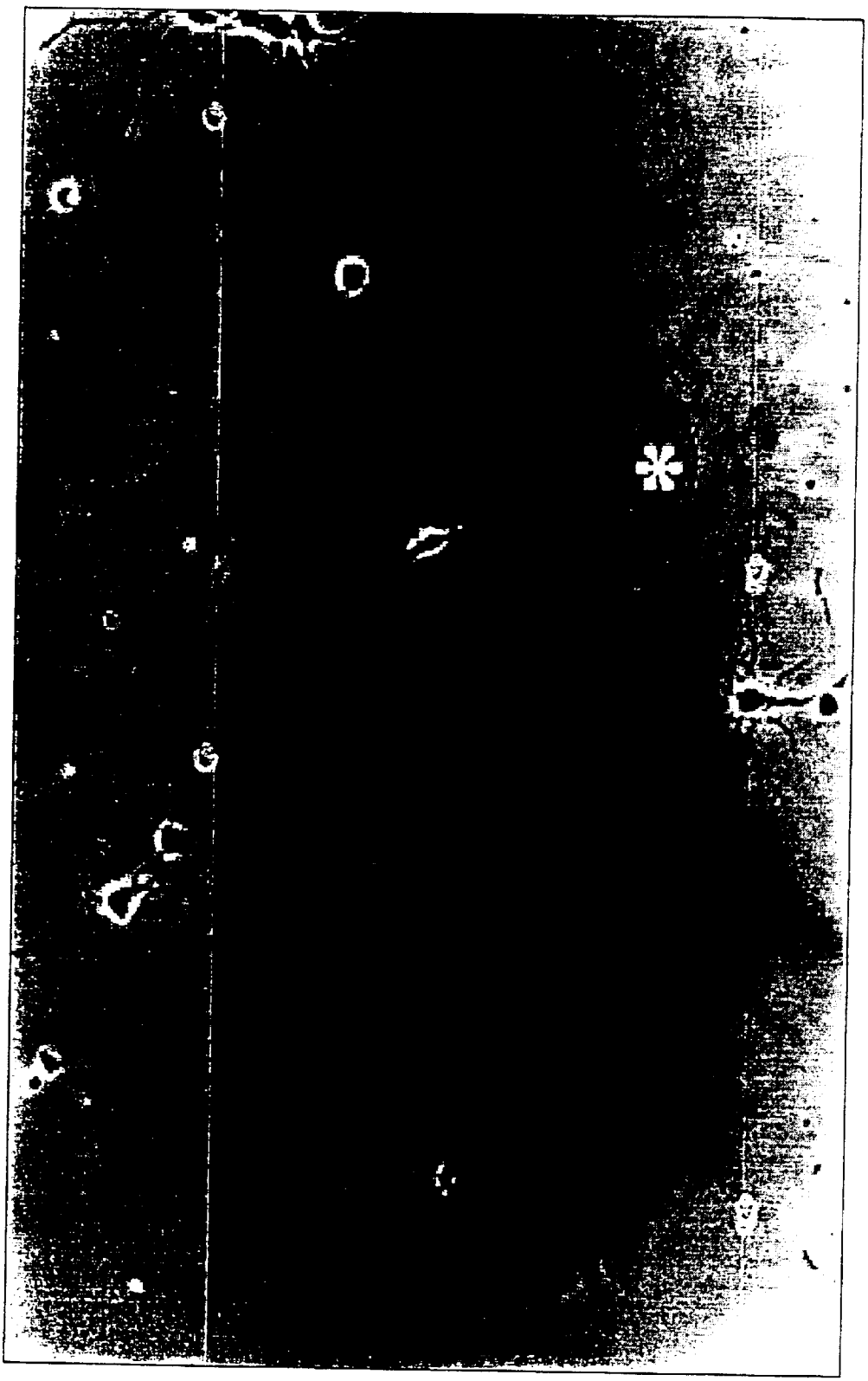
Figure 9C:
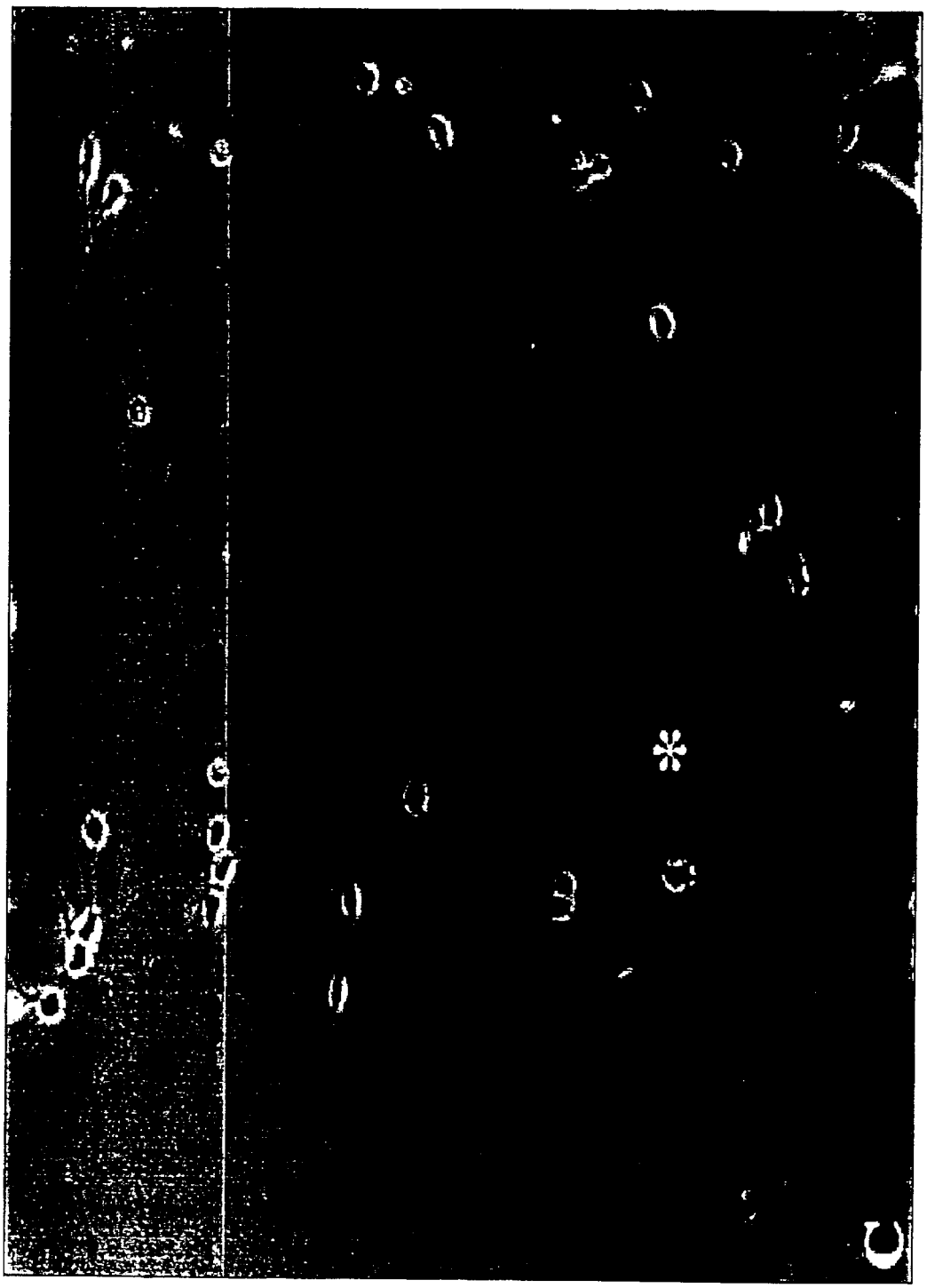

Utilizing the in vitro assay described in Example 2, the effect of treating hippocampal cells with a bastadin 10 analog was compared to the effect of treating hippocampal cells with radicicol. FIG. 9A is a light micrograph of untreated hippocampal cells after 72 hours. FIG. 9B, another light micrograph, illustrates the effect radicicol has on neurite outgrowth and 9C demonstrates the same for a bastadin 10 analog (Davis B-10, bastadin). Quantitative measurements of the lengths of neurite outgrowths for untreated cells, cells treated with radicicol, and cells treated with the bastadin 10 analog are presented in FIG. 10. Taken together, FIGS. 9 and 10 illustrate the ability of bastadin to stimulate neurite outgrowth.

EXAMPLE 20

Methods of Use

The neurotrophic compounds of the invention are administered in an effective amount sufficient to stimulate nerve growth or regeneration compared to a control. Suitable local concentrations for nerve cell growth or nerve regeneration can be readily assessed using an in vitro assay, e.g., the assay described in Example 1. Alternatively, nerve cell growth or regeneration can be determined by an in vivo assay, or by direct or indirect signs of nerve cell growth and regeneration in a subject (for example a restoration of motor and/or sensory function in the hand in the area of innervation of a previously transected median nerve). Preferably, the increase in nerve cell growth or regeneration rate is at least 10%, preferably at least 30%, and most preferably 50% or more compared to a control. Preferred dosage levels are between about 0.1 to about 400 mg/kg per day of the FK506 analog for subcutaneous delivery. For oral administration, dosage level examples are between about 0.01 to about 40 mg/kg/day. Alternatively, the dose can be sufficient to achieve tissue concentrations that have been shown to be neurotrophic in vitro.

Pharmaceutical compositions according to the invention can be periodically administered to a mammalian subject (e.g., a human patient), in need of such treatment, to promote neuronal regeneration and functional recovery and to stimulate neurite outgrowth and thereby to treat various neuropathological states, including damage to peripheral nerves and the central nervous system caused by physical injury (e.g., spinal cord injury and trauma, sciatic or facial nerve lesion or injury, limb transplantation following amputation), disease (e.g., diabetic neuropathy), cancer chemotherapy (e.g., neuropathy induced by acrylamide, taxol, vinca alkaloids and doxorubicin), brain damage associated with stroke and ischemia, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barre syndrome, Alzheimer's disease, Parkinson's disease, and Huntington's chorea.

In addition, pharmaceutical compositions according to the present invention display a wide range of other therapeutic or prophylactic properties, including, treatment of stroke (see, e.g., Sharkey and Butcher, *Nature* 371:336–339, 1994, Vagita et al., *Life Sciences* 59:1643–1650, 1996; Tolcine et al., *Neurosci. Lett.* 206:81–84, 1996; Drake et al., *Acta. Physiol. Scand.* 158:155–159, 1996; and Kuroda et al., *Neurosci. Res. Comm.* 19:83–90, 1996), AIDS dementia (see, e.g., Dawson and Dawson, *Adv. Neuroimmunol.* 4:167–173, 1994; and Sekigawa et al., *J. Clin. Immunol.* 15:312–317, 1995); hair growth (Yamamoto et al., *J. Investig. Dermatol.* 102:160–164, 1994; Jiang et al., *J. Investig. Dermatol.* 104:523–525, 1995); and connective tissue disorders (see e.g., Steinmann et al., *J. Biol. Chem.* 266: 1299–1303, 1991), and as a male contraceptive (see e.g., Hisatomi et al., *Toxicology* 109:75–83, 1996).

A transection of a peripheral nerve or a spinal cord injury can be treated by administering a nerve growth stimulating amount of the agent to the mammal and grafting to the peripheral nerve or spinal cord a nerve graft such as an allograft (Osawa et al., *J. Neurocytol.* 19:833–849, 1990; Buttemeyer et al., *Ann. Plastic Surgery* 35:396401, 1995) or an artificial nerve graft (Madison and Archibald, *Exp. Neurol.* 128:266–275, 1994; Wells et al., *Exp. Neurol.* 146:395–402, 1997). The space between the transected ends of the peripheral nerve or spinal cord is preferably filled with a non-cellular gapfilling material such as collagen, methyl cellulose, etc., or cell suspensions that promote nerve cell growth, such as Schwann cells (Xu et al., *J. Neurocytol.* 26:1–16, 1997), olfactory cells, and sheathing cells (Li et al. *Science* 277:2000–2002, 1997). The nerve growth promoting agent can be included together with such cellular or non-cellular gap-filling materials, or administered systemically before, during or after the nerve graft procedure.

EXAMPLE 21

Pharmaceutical Formulations

Pharmaceutical formulations according to the present invention encompass formulations that include an amount (for example, a unit dosage) of the neurotrophic agent together with one or more non-toxic pharmaceutically acceptable excipients, including carriers, diluents, and/or adjuvants, and optionally other biologically active ingredients. Standard pharmaceutical formulation techniques are used, such as those disclosed in Remington's *Pharmaceutical Sciences*, Mack Publishing Co., Easton, Pa. (19th Edition).

A pharmaceutical formulation according to the invention includes one or more of the neurotrophic agents of the present invention, and can also include, for example, one or more other biologically active ingredients, such as FK506 or an FKBP12-binding FK506 analog, NGF, IGF-1, $\alpha$-FGF, $\beta$-FGF, PDGF, BDNF, CNTF, GDNF, NT-3, and NT 4/5. When the SRC disrupting agents of the present invention are combined with a second neurotrophic agent, the two agents are ideally selected such that they structurally or functionally disrupt the SRC by acting at different SRC components. For example, the first agent may be geldanamycin (which promotes dissociation of p23) and the second agent may be FKBP52-Ab (which interferes with association of FKBP-52 to hsp-90). In particular embodiments, the composition includes NGF, or another agent that stimulates nerve growth in combination with the SRC disrupting complex, or the neurotrophic action of which is augmented by administration in combination with the SRC disrupting agent.

The dosage of the combined biologically active agents is sufficient to achieve tissue concentrations at the site of action that are similar to those that are shown to achieve in vivo nerve regeneration. Pharmaceutical formulations may include, for example, an amount of a NGF, such that the subject receives a dosage of between about 0.01 to 100 $\mu$g/kg body weight/day. The NGF (or other adjuvant) can be administered separately, concurrently, consecutively, or within less than about five hours of each other.

The compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Such pharmaceutical compositions can be administered systemically or locally in any manner appropriate to the treatment of a given condition, including orally, parenterally, rectally, nasally, buccally, vaginaluy, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions preferably readily penetrate the blood-brain barrier when peripherally administered or are administered intraventricularly.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, e.g., buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentrations that has been shown to be neurotrophic in vitro. For example, a dosage of about 0.1 to about 400 mg/kg per day of the active ingredient may be useful in the treatment of the conditions listed above.

The compounds can be used in the form of salts preferably derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fulmarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.).

Basic nitrogen-containing groups can be quaternized, e.g., with such agents as C1–8 alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Pharmaceutical compositions can be included in a kit accompanied by instructions for intended use, for example instructions required by a pharmaceutical regulatory agency, such as the Food and Drug Administration in the United States.

Summary

The foregoing examples illustrate that neurotrophic properties of neuroimmunophilin ligands (FK506) and steroid hormones are mediated by physical or functional disruption of steroid receptor complexes. Some of the components of the complex that can act as targets for disruption include FKBP-52, hsp-90 and p23, which are all present together in mature steroid receptor complexes, which can be disrupted by geldanamycin. Since FKBP-52 can associate with microtubules and dynein, and via its TPR motifs also associate with kinesin, it can also have a direct role in the movement (axonal transport) of cytoskeletal elements and, consequently, axonal elongation.

In view of the many possible embodiments to which the principles of our invention may be applied, it should be recognized that the illustrated embodiments are only examples of the invention and should not be taken as a limitation on the scope of the invention. Rather, the scope of the invention is defined by the following claims, and equivalents thereof. We therefore claim as our invention all that comes within the scope and spirit of these claims, including equivalents thereof.

I claim:

1. A method for stimulating nerve cell growth in a subject comprising administering to the subject a bastadin compound or its analogs, wherein said bastadin is selected from the group consisting of bastadin 1, 2, 3, 4, 5, 6, 7, 8, 9, 10, 11, 12, 13, 14, 15, 16, 17, 18, 19 and 20.

2. The method of claim 1, wherein the agent is bastadin 1, 2, 3, 4, 5, 6, 7, 8, 9, 10, 11, 12, 13, 14, 15, 16, 17, 18, 19, or 20.

3. The method of claim 2, wherein the agent is bastadin 10.

4. The method of claim 2, wherein the agent is an analog of the bastadin.

5. The method of claim 1 further comprising applying a sufficient amount of heat to an area where nerve cell growth is desired.

6. The method of claim 1, further comprising providing a template in an area where nerve growth is desired.

7. The method of claim 6, wherein the template is a tubular member that defines an anatomical pathway along which nerve growth is desired.

8. The method of claim 6, wherein the template is placed between opposing ends of a transected or partially transected nerve.

9. The method of claim 6 further comprising applying to the template a therapeutically sufficient amount of heat, effective to enhance nerve growth.

10. The method of claim 1, wherein the agent is a bastadin or its analog having the structure:

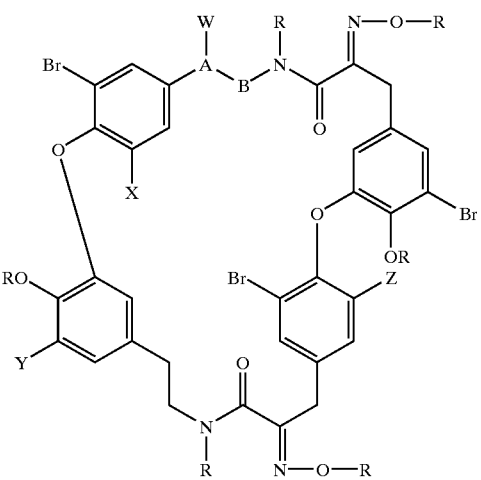

where each R is independently selected from the group consisting of H, C1–8 alkyl, and sulfato, W is selected from the group consisting of H, OH, and C1–8 alkoxy, X, Y, and Z are selected independently from the group consisting of hydrogen, halogen, hydroxyl, and C1–8 alkoxy, and A and B are carbon atoms that are joined by a single or a double bond.

11. The method of claim 1, wherein the agent is a bastadin or its analog having the structure:

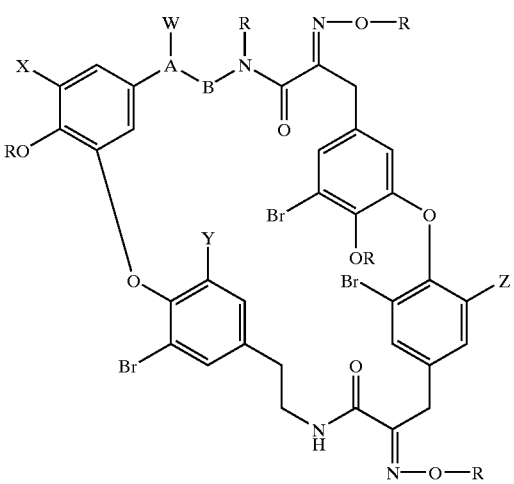

where each R is independently selected from the group consisting of H, C1–8 alkyl, and sulfato, W is selected from the group consisting of H, OH, and C1–8 alkoxy, X, Y, and Z are selected independently from the group consisting of hydrogen, halogen, hydroxyl, and C1–8 alkoxy, and A and B are carbon atoms that are joined by a single or a double bond.

12. The method of claim 1, wherein the agent is a bastadin or its analog having the structure:

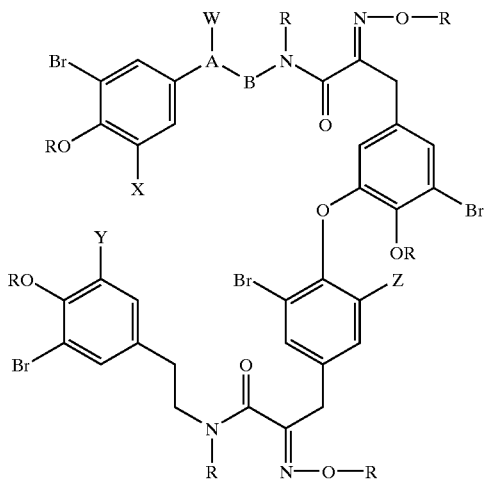

where each R is independently selected from the group consisting of H, C1–8 alkyl, and sulfato, W is selected from the group consisting of H, OH, and C1–8 alkoxy, X, Y, and Z are selected independently from the group consisting of hydrogen, halogen, hydroxyl, and C1–8 alkoxy, and A and B are carbon atoms that are joined by a single or a double bond.

13. The method of claim 1, wherein the agent is a bastadin or its analog having the structure:

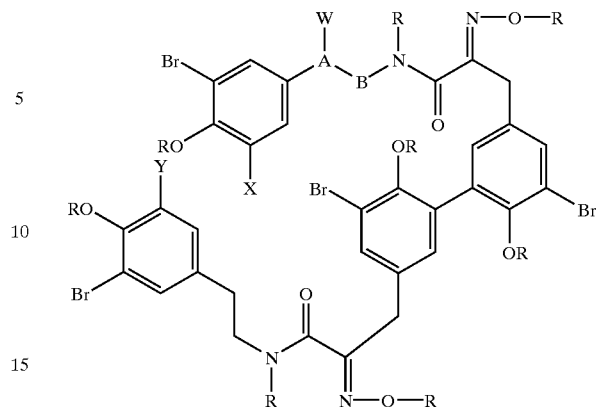

where each R is independently selected from the group consisting of H, C1–8 alkyl, and sulfato, W is selected from the group consisting of H, OH, and C1–8 alkoxy, X and Y are selected independently from the group consisting of hydrogen, halogen, hydroxyl, and C1–8 alkoxy, and A and B are carbon atoms that are joined by a single or a double bond.

* * * * *